US009862969B2

(12) United States Patent
Murakami

(10) Patent No.: US 9,862,969 B2
(45) Date of Patent: Jan. 9, 2018

(54) PROMOTER DERIVED FROM HUMAN GENE

(71) Applicant: Daiichi Sankyo Company, Limited, Chuo-ku, Tokyo (JP)

(72) Inventor: Kenji Murakami, Tokyo (JP)

(73) Assignee: Daiichi Sankyo Company, Limited, Chuo-ku, Tokyo (JP)

( * ) Notice: Subject to any disclaimer, the term of this patent is extended or adjusted under 35 U.S.C. 154(b) by 196 days.

(21) Appl. No.: 14/288,942

(22) Filed: May 28, 2014

(65) Prior Publication Data

US 2014/0342401 A1 Nov. 20, 2014

Related U.S. Application Data

(63) Continuation of application No. PCT/JP2012/080532, filed on Nov. 27, 2012.

(30) Foreign Application Priority Data

Nov. 28, 2011 (JP) ................ 2011-258724

(51) Int. Cl.
| | |
|---|---|
| C12N 15/85 | (2006.01) |
| C12P 21/00 | (2006.01) |
| C12P 21/02 | (2006.01) |
| C07K 16/00 | (2006.01) |
| C07K 16/18 | (2006.01) |
| C07K 14/47 | (2006.01) |
| C12N 15/63 | (2006.01) |

(52) U.S. Cl.
CPC .............. *C12N 15/85* (2013.01); *C07K 14/47* (2013.01); *C07K 16/00* (2013.01); *C07K 16/18* (2013.01); *C12N 15/63* (2013.01); *C12P 21/00* (2013.01); *C12P 21/02* (2013.01); *C07K 2317/24* (2013.01); *C12N 2830/85* (2013.01)

(58) Field of Classification Search
None
See application file for complete search history.

(56) References Cited

U.S. PATENT DOCUMENTS

| 7,423,135 B2 | 9/2008 | Estes | |
|---|---|---|---|
| 8,759,088 B2 | 6/2014 | Steidler | |
| 2003/0232056 A1* | 12/2003 | Fanger et al. ............ | 424/185.1 |

FOREIGN PATENT DOCUMENTS

| JP | 2000-507087 A | 6/2000 |
|---|---|---|
| JP | 2002-320477 A | 11/2002 |
| JP | 2007-525956 A | 9/2007 |
| JP | 2010-515445 A | 5/2010 |
| WO | 97/23633 A1 | 7/1997 |
| WO | 2005/000888 A2 | 1/2005 |
| WO | 2006/123097 A2 | 11/2006 |
| WO | 2009/155950 A1 | 12/2009 |
| WO | 2012/005378 A2 | 1/2012 |
| WO | 2012/030218 A1 | 3/2012 |

OTHER PUBLICATIONS

Sequence Alignment of SEQ ID No. 1 with AC108488. STIC Sequence Search conducted on Jun. 8, 2015, 5 pages.*
International Search Report dated Mar. 12, 2013, issued in corresponding International Application No. PCT/JP2012/080532, filed Nov. 27, 2012, 4 pages.
International Preliminary Report on Patentability and Written Opinion dated Jun. 3, 2014, issued in corresponding International Application No. No. PCT/JP2012/080532, filed Nov. 27, 2012, 10 pages.
Smirnova, E.V., "*Homo sapiens* rpS21 Gene for Ribosomal Protein S21, Exons 1-5," GenBank [online] Accession No. AJ250907.1, uploaded Nov. 14, 2006, <http://www.ncbi.nlm.nih.gov/nuccore/AJ250907> [retrieved Oct. 15, 2014], 3 pages.
Waterston, R.H., "*Homo sapiens* BAC Clone RP13-512J5 from 2, Complete Sequence," GenBank [online] Accession No. AC108488. 4, uploaded Apr. 8, 2005, <http://www.ncbi.nlm.nih.gov/nuccore/AC108488.4> [retrieved Oct. 15, 2014], 14 pages.
Annilo, T., et al., "The Human Ribosomal Protein S7-Encoding Gene: Isolation, Structure and Localization in 2p25," Gene 165(2):297-302, Nov. 1995.
Database EMBL [Online] EBI, Hinxton, UK, Accession No. AC018836, "*Homo sapiens* Chromosome 3 Clone RP11-588P9 Map 3p, Complete Sequence," Human Genomic Center Institute of Genetics, Beijing, Dec. 23, 1999, 3 pages.
Database EMBL [Online] EBI, Hinxton, UK, Accession No. AC084209, "*Homo sapiens* BAC Clone RP11-462C24 From 4, Complete Sequence," Genome Sequencing Center, St. Louis, Oct. 17, 2000, 3 pages.
Extended European Search Report dated Jul. 31, 2015, issued in corresponding Application No. EP 12 853 220.7, filed Nov. 27, 2012, 16 pages.
Hoeksema, F., et al., "Placing the RPL32 Promoter Upstream of a Second Promoter Results in a Strongly Increased Number of Stably Transfected Mammalian Cell Lines That Display High Protein Expression Levels," Biotechnology Research International, vol. 2011, Article ID 492875, 11 pages, 2011.
Perry, R.P., "The Architecture of Mammalian Ribosomal Protein Promoters," BMC Evolutionary Biology 5:15, Feb. 2005, 16 pages.
Roepcke, S., et al., "Identification of Highly Specific Localized Sequence Motifs in Human Ribosomal Protein Gene Promoters," Gene 365:48-56, Jan. 2006.
Roepcke, S., et al., "A Tandem Sequence Motif Acts as a Distance-Dependent Enhancer in a Set of Genes Involved in Translation by Binding the Proteins NonO and SFPQ," BMC Genomics 12:624, Dec. 2011, 16 pages.
Waterston, R.H., Database EMBL [Online] EBI, Hinxton, UK, Accession No. AC108488, "*Homo sapiens* BAC Clone RP13-512J5 From 2, Complete Sequence," Genome Sequencing Center, St. Louis, Jan. 31, 2002, 9 pages.

(Continued)

*Primary Examiner* — Channing S Mahatan
(74) *Attorney, Agent, or Firm* — Christensen O'Connor Johnson Kindness PLLC

(57) ABSTRACT

The present invention relates to a transfected mammalian host cell whose ability to secrete a foreign protein has been enhanced by using a foreign gene expression vector having a promoter derived from a human gene, and a method for producing the foreign protein using the host cell. A method for enhancing the production of a foreign protein to be used in a pharmaceutical protein product in a host cell such as a cultured mammalian cell is provided. A promoter derived from a human gene having a promoter activity higher than that of a cytomegalovirus (CMV) promoter in a host cell such as a cultured mammalian cell is provided.

11 Claims, 21 Drawing Sheets

(56) References Cited

OTHER PUBLICATIONS

Dong, Z.-Y., et al., "A Functional Analysis of Short Stature Homeobox (SHOX) Gene Promoter Mutation in Idiopathic Short Stature," Chinese Journal of Endocrinology and Metabolism 25(2):147-149, Apr. 2009.

Gong, Y., "Analysis of the Cellobiohydrolase I Promoter Mutation as Well as Functional Study on the Gene ppo Encoding psi Factor Producing Oxygenase in Trichoderma reesei," Master's Thesis, Shandong University, Shandong, China, Oct. 2014, 90 pages.

Kulozik, A.E., et al., "Thalassemia Intermedia: Moderate Reduction of β Globin Gene Transcriptional Activity by a Novel Mutation of the Proximal CACCC Promoter Element," Blood 77(9):2054-2058, May 1991.

Second Office Action dated Mar. 3, 2016, issued in corresponding Chinese Application No. 2012800682368, filed Nov. 27, 2012, 11 pages.

\* cited by examiner

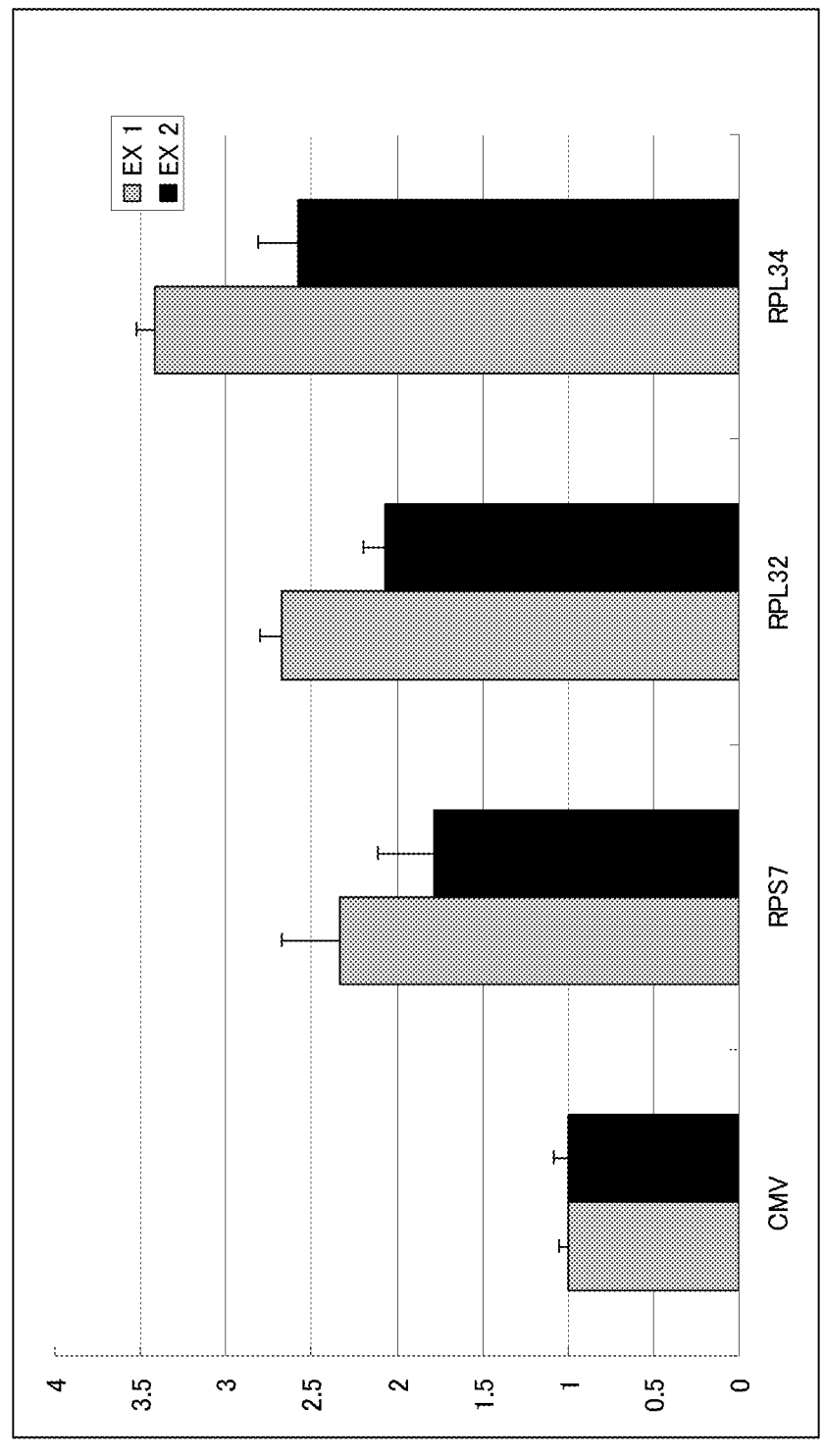
[FIG. 1]

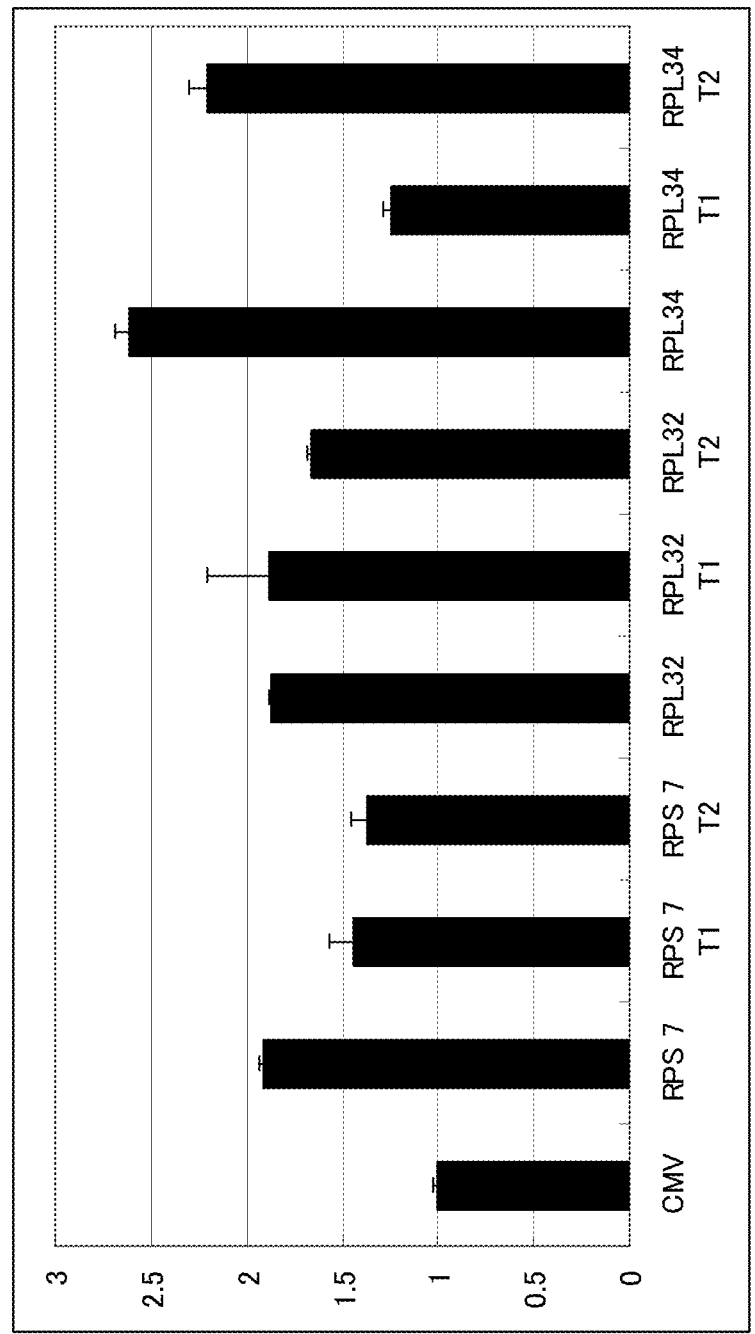
[FIG. 2]

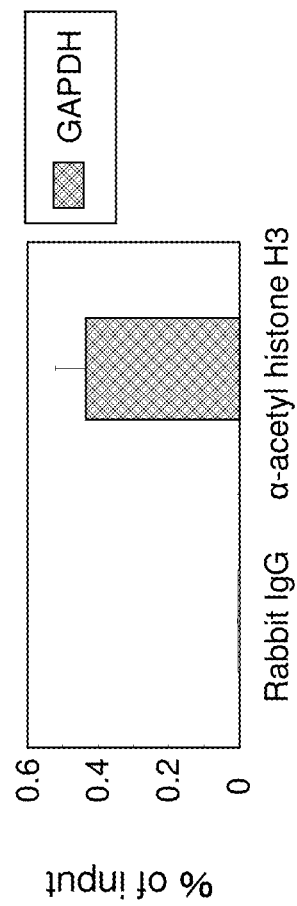
[FIG. 3]

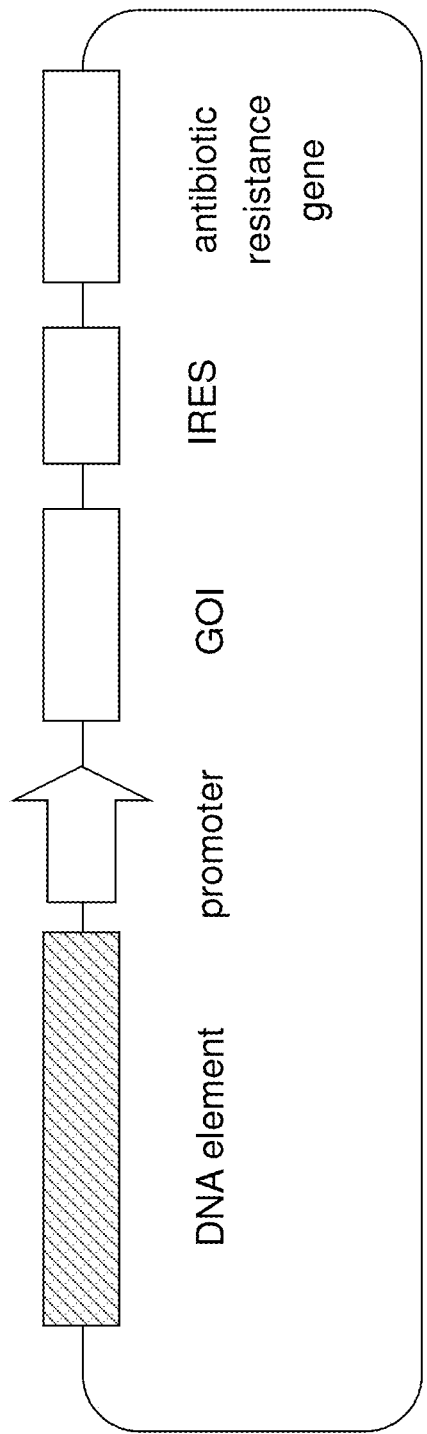
[FIG. 4]
GOI : Gene of Interest (SEAP)

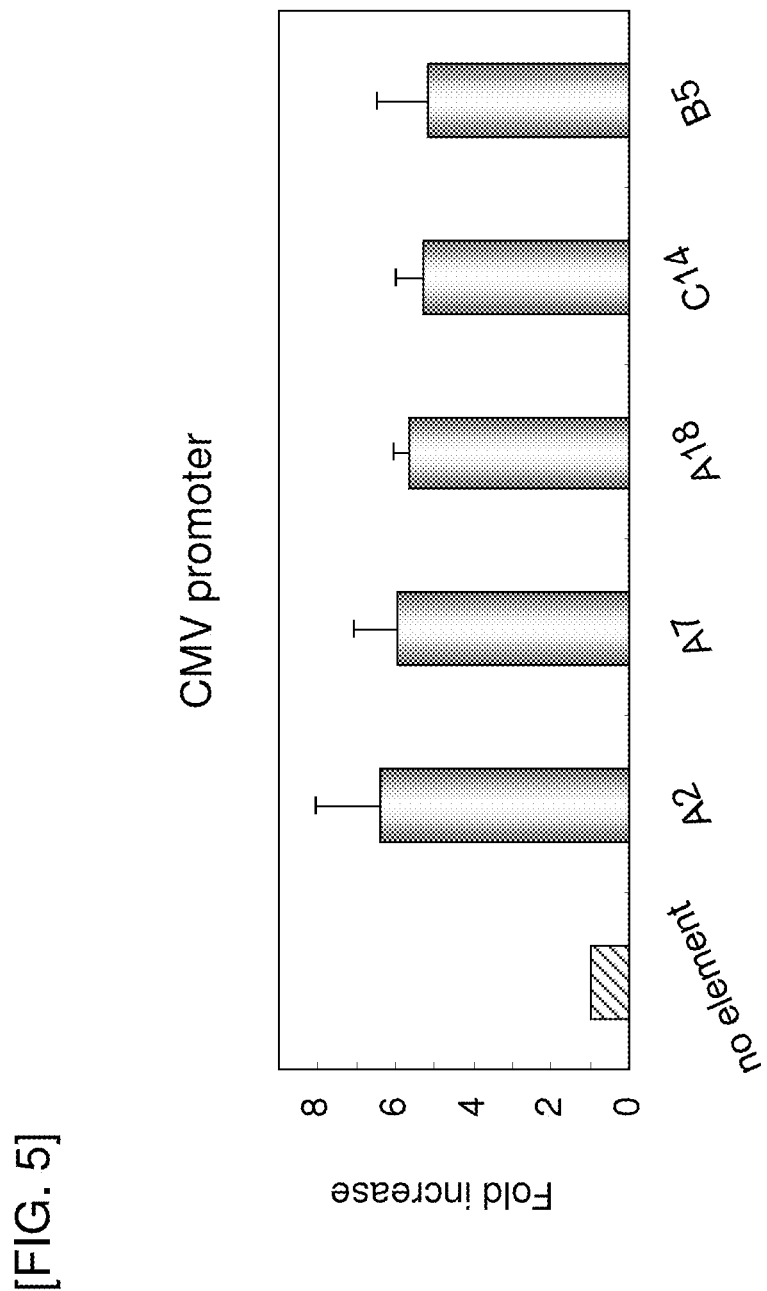
[FIG. 5]

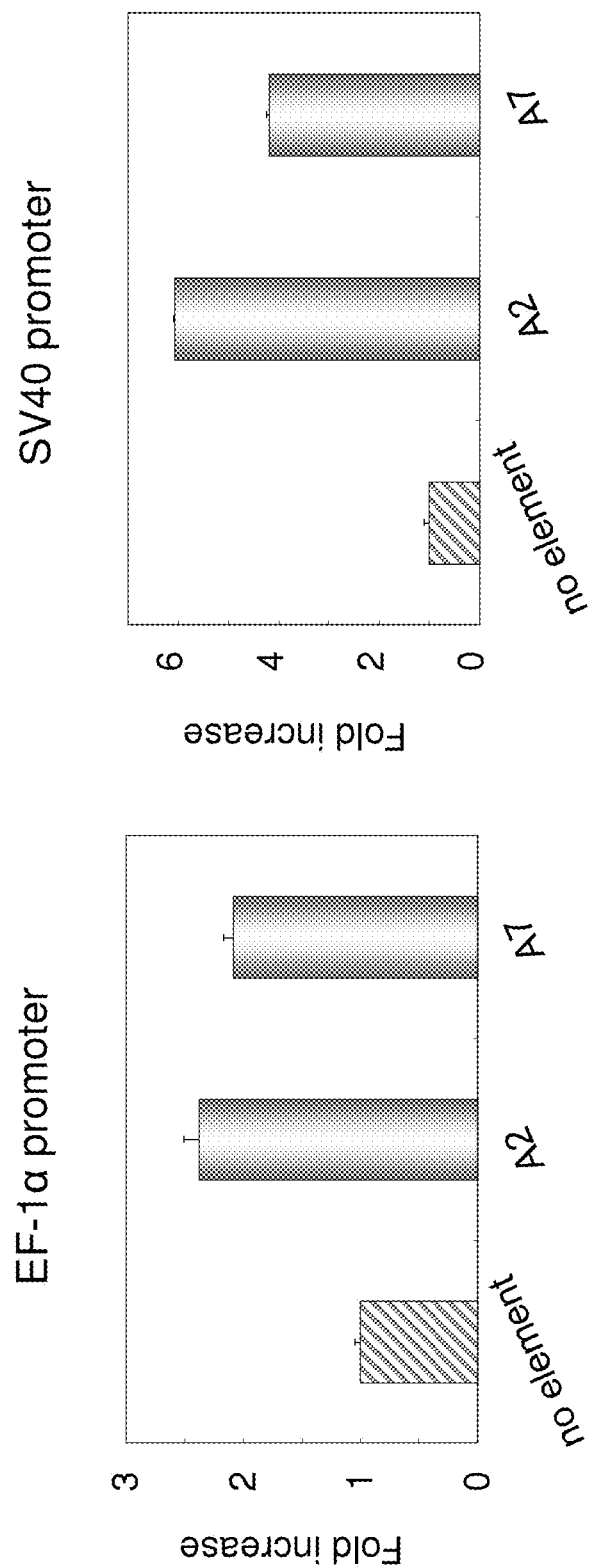
[FIG. 6]

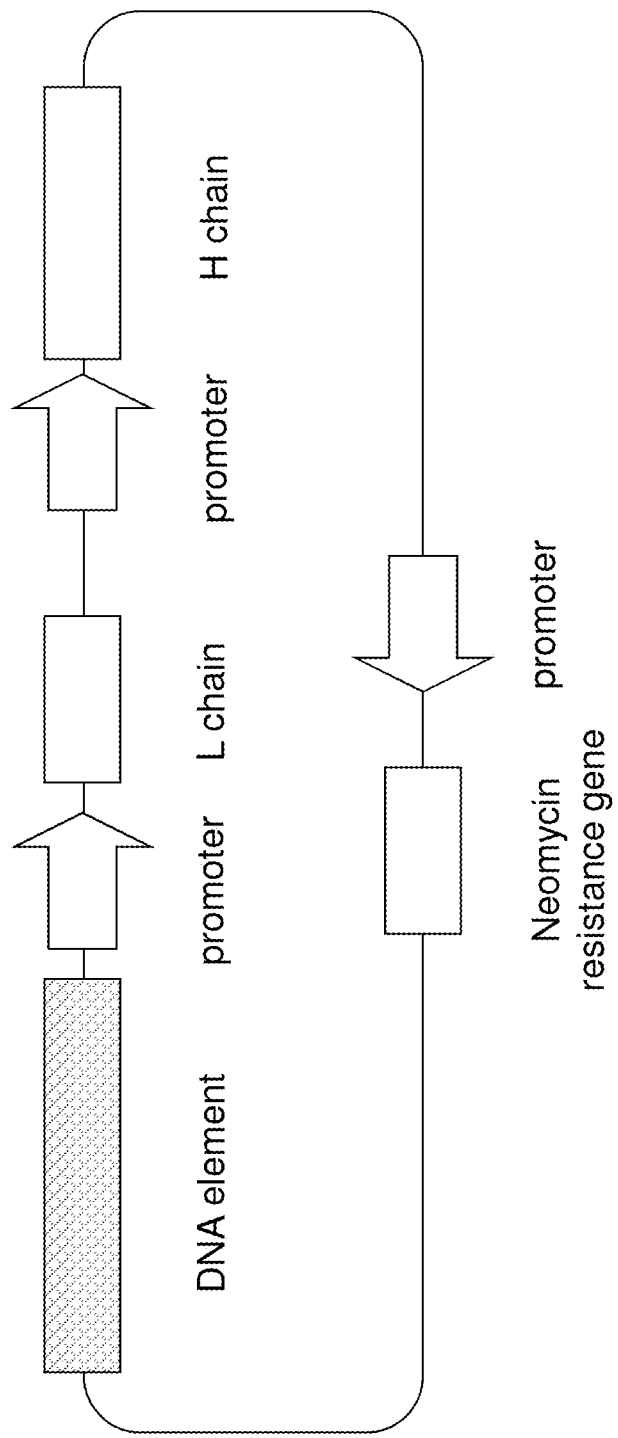
[FIG. 7]

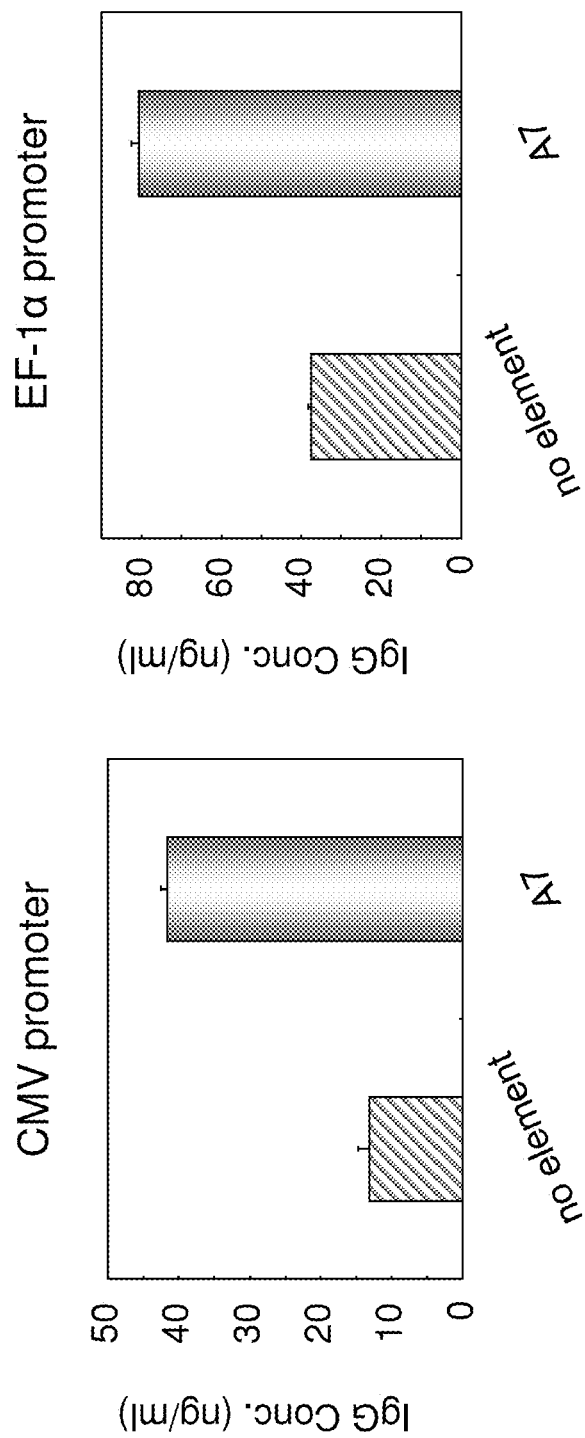
[FIG. 8]

[FIG. 9]

| ID | Location | Location | Length(bp) |
|---|---|---|---|
| A2 | 80966429 | 80974878 | 8450 |
| A2-1 | 80966429 | 80969428 | 3000 |
| A2-2 | 80969229 | 80972228 | 3000 |
| A2-3 | 80971829 | 80974878 | 3050 |
| A2-4 | 80967129 | 80969128 | 2000 |
| A2-5 | 80967129 | 80968628 | 1500 |
| A2-6 | 80967129 | 80970128 | 3000 |
| A2-7 | 80968429 | 80971428 | 3000 |
| A2-8 | 80970429 | 80973428 | 3000 |
| A2-9 | 80966429 | 80970128 | 3700 |
| A2-10 | 80968429 | 80972228 | 3800 |
| A2-11 | 80969229 | 80973428 | 4200 |
| A2-12 | 80967129 | 80972228 | 5100 |
| A2-13 | 80968429 | 80973428 | 5000 |
| A2-14 | 80969229 | 80974878 | 5650 |
| A2-15 | 80966429 | 80972228 | 5800 |
| A2-16 | 80967129 | 80973428 | 6300 |
| A2-17 | 80968429 | 80974878 | 6450 |

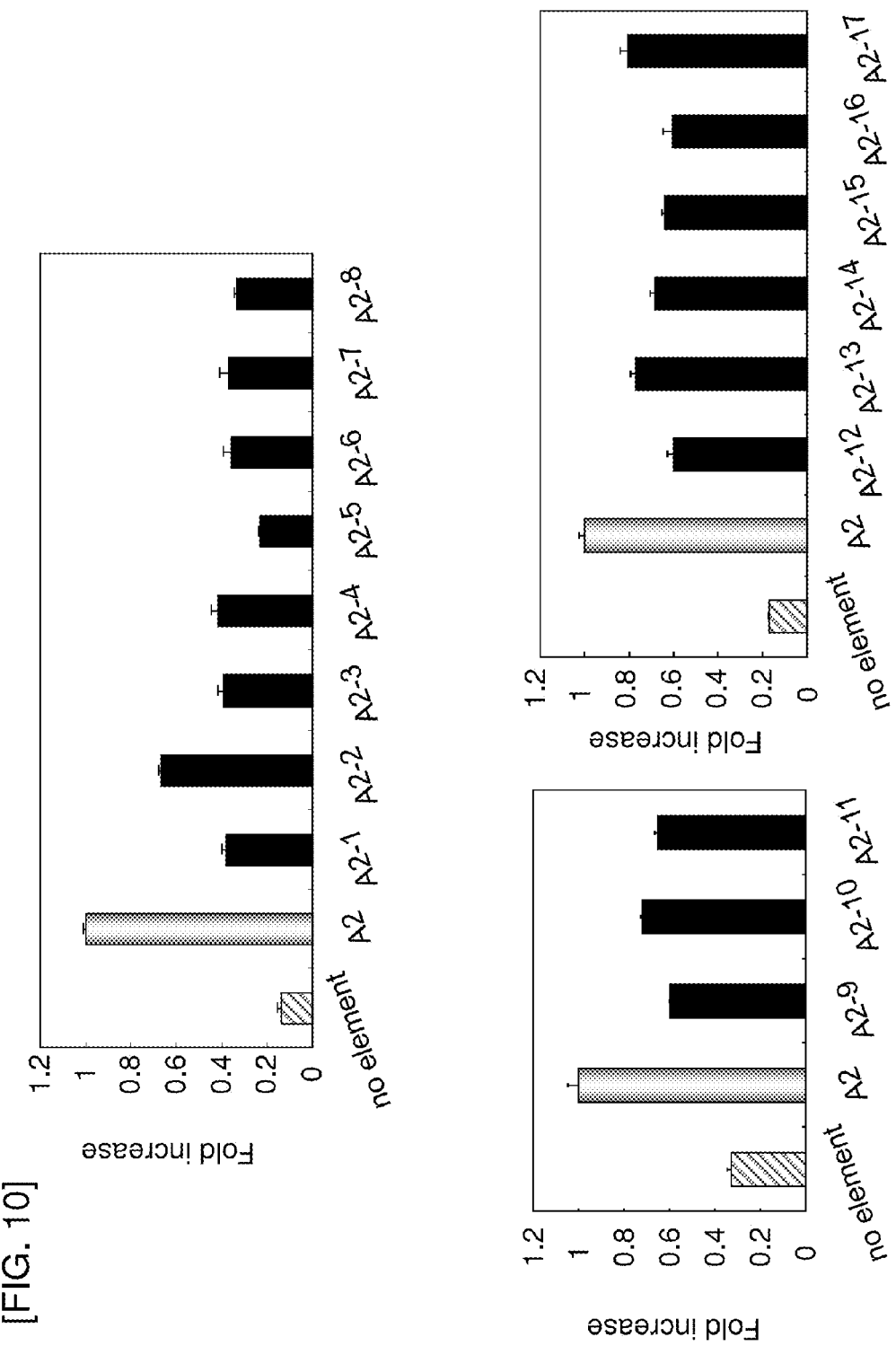
[FIG. 10]

[FIG. 11]

| ID | Location | Location | Length(bp) |
|---|---|---|---|
| A7 | 88992123 | 89000542 | 8420 |
| A7-1 | 88992723 | 88995722 | 3000 |
| A7-2 | 88995723 | 89000542 | 4820 |
| A7-3 | 88997523 | 89000542 | 3020 |
| A7-4 | 88995523 | 88998522 | 3000 |
| A7-5 | 88993623 | 88996622 | 3000 |
| A7-6 | 88996523 | 88999522 | 3000 |
| A7-7 | 88994523 | 88997522 | 3000 |
| A7-8 | 88992123 | 88995722 | 3600 |
| A7-9 | 88993623 | 88997522 | 3900 |
| A7-10 | 88994523 | 88998522 | 4000 |
| A7-11 | 88995523 | 88999522 | 4000 |
| A7-12 | 88996523 | 89000542 | 4020 |
| A7-13 | 88992123 | 88997522 | 5400 |
| A7-14 | 88993623 | 88998522 | 4900 |
| A7-15 | 88994523 | 88999522 | 5000 |
| A7-16 | 88995523 | 89000542 | 5020 |
| A7-17 | 88992123 | 88998522 | 6400 |
| A7-18 | 88993623 | 88999522 | 5900 |

[FIG. 12]
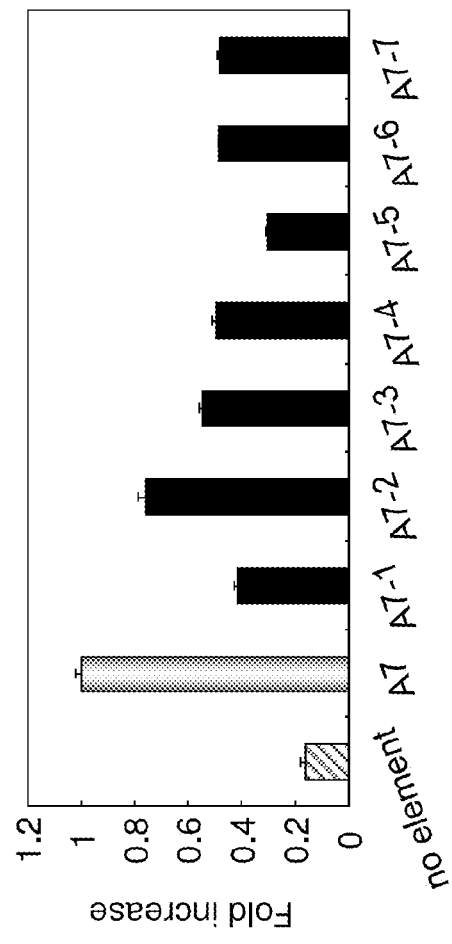
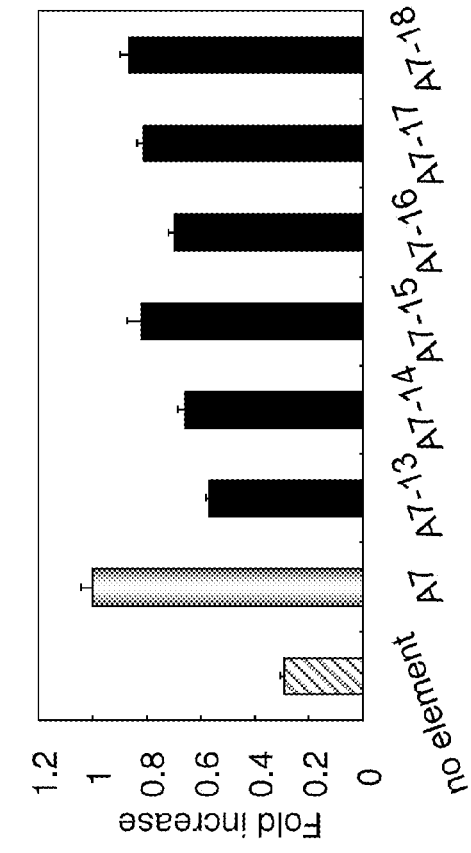
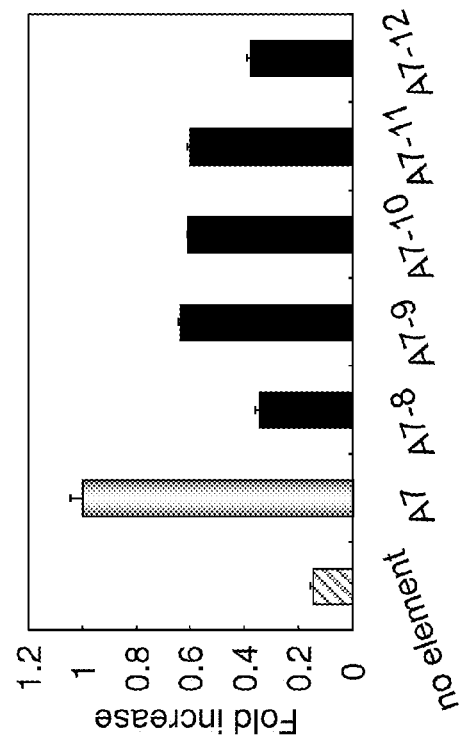

[FIG. 13]

| ID | Location | Location | Length(bp) |
|---|---|---|---|
| A18 | 111275976 | 111284450 | 8475 |
| A18-1 | 111275976 | 111281015 | 5040 |
| A18-2 | 111276976 | 111281977 | 5002 |
| A18-3 | 111277976 | 111282975 | 5000 |
| A18-4 | 111278975 | 111282975 | 4001 |

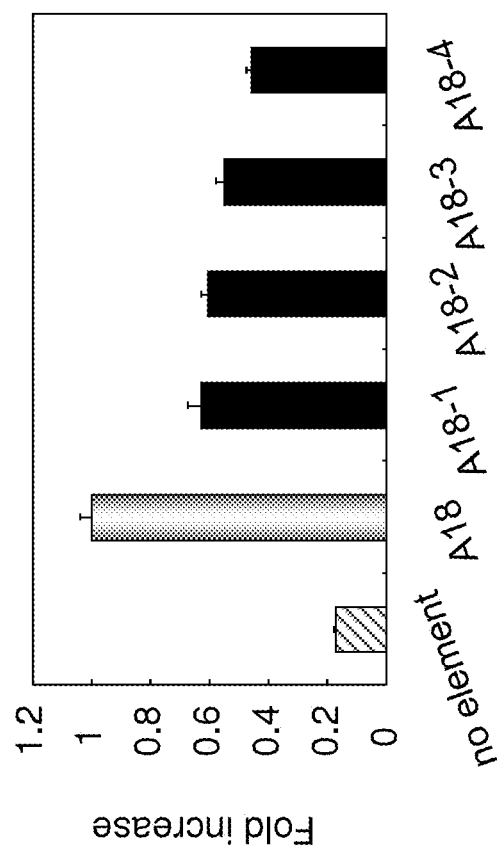
[FIG. 14]

[FIG. 15]

| ID | Location | Location | Length(bp) |
|---|---|---|---|
| B5 | 143034684 | 143043084 | 8401 |
| B5-1 | 143034684 | 143038684 | 4001 |
| B5-2 | 143034684 | 143037883 | 3200 |
| B5-3 | 143037174 | 143040284 | 3111 |
| B5-4 | 143040056 | 143043084 | 3029 |
| B5-5 | 143035584 | 143038684 | 3101 |
| B5-6 | 143038684 | 143041683 | 3000 |

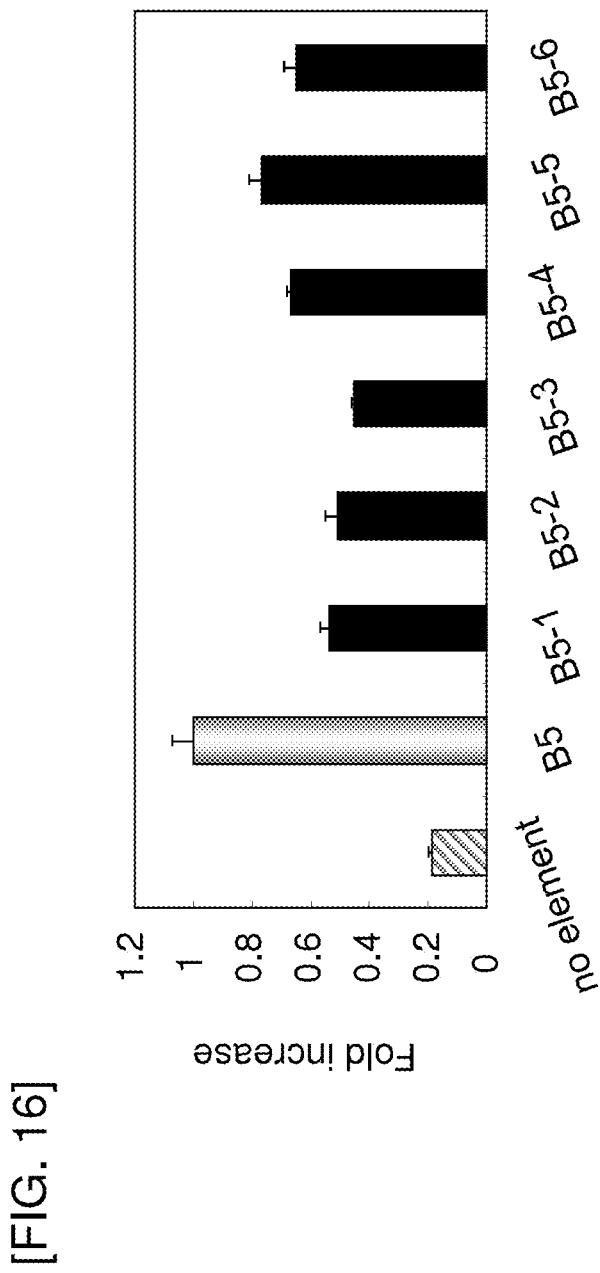
[FIG. 16]

[FIG. 17]

| ID | Location | Location | Length(bp) |
|---|---|---|---|
| C14 | 46089056 | 46097482 | 8427 |
| C14-1 | 46090015 | 46093070 | 3056 |
| C14-2 | 46091042 | 46094069 | 3028 |
| C14-3 | 46093075 | 46096174 | 3100 |
| C14-4 | 46090015 | 46097196 | 7182 |
| C14-5 | 46090015 | 46095066 | 5052 |
| C14-6 | 46093994 | 46097196 | 3203 |
| C14-7 | 46090015 | 46094069 | 4055 |
| C14-8 | 46092049 | 46096174 | 4126 |
| C14-9 | 46093075 | 46097196 | 4122 |
| C14-10 | 46089056 | 46094069 | 5014 |
| C14-11 | 46091042 | 46096174 | 5133 |
| C14-12 | 46092049 | 46097196 | 5148 |
| C14-13 | 46090015 | 46096174 | 6160 |
| C14-14 | 46091042 | 46097196 | 6155 |

[FIG. 18]
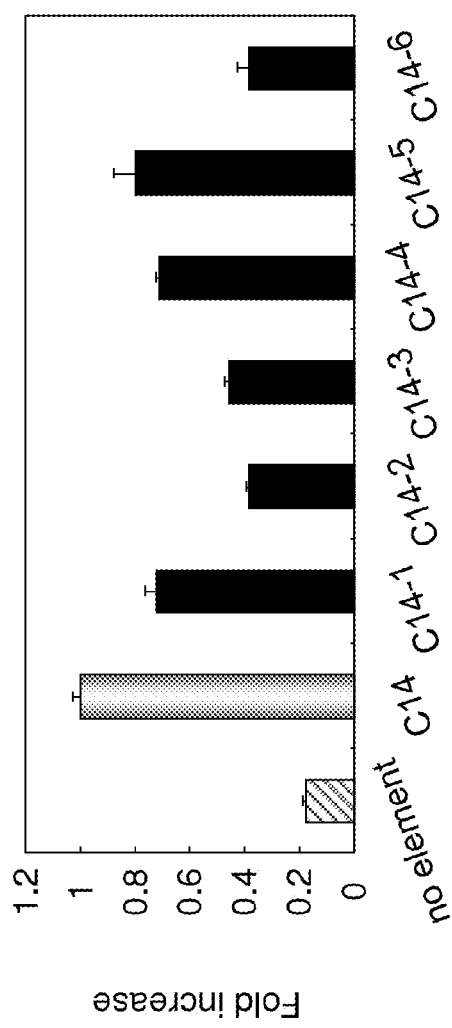
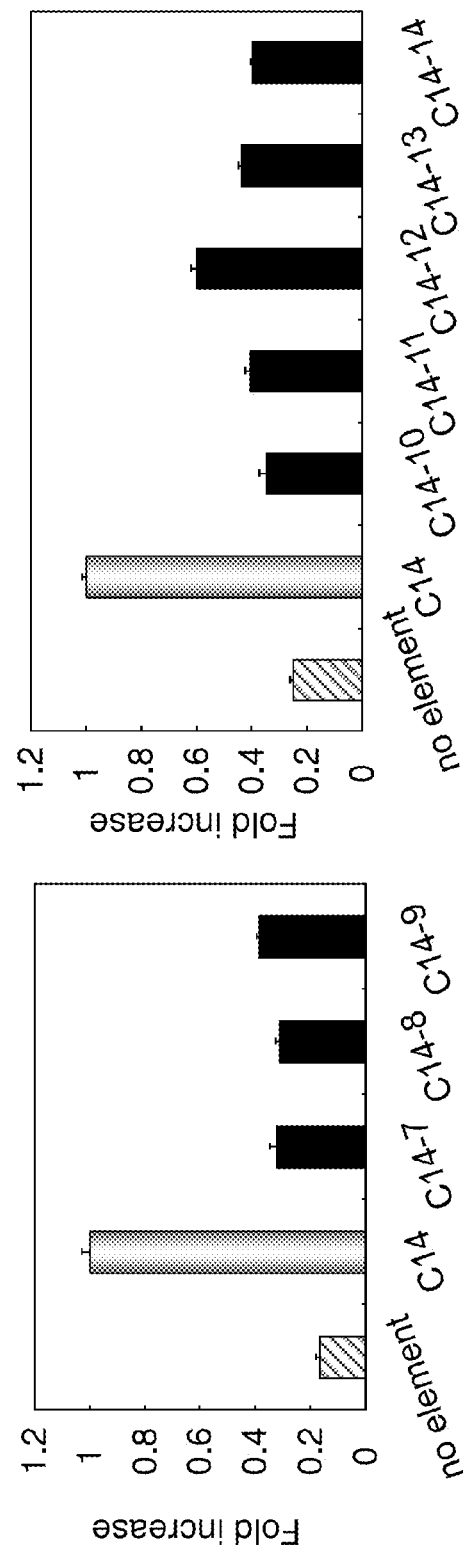

[FIG. 19]
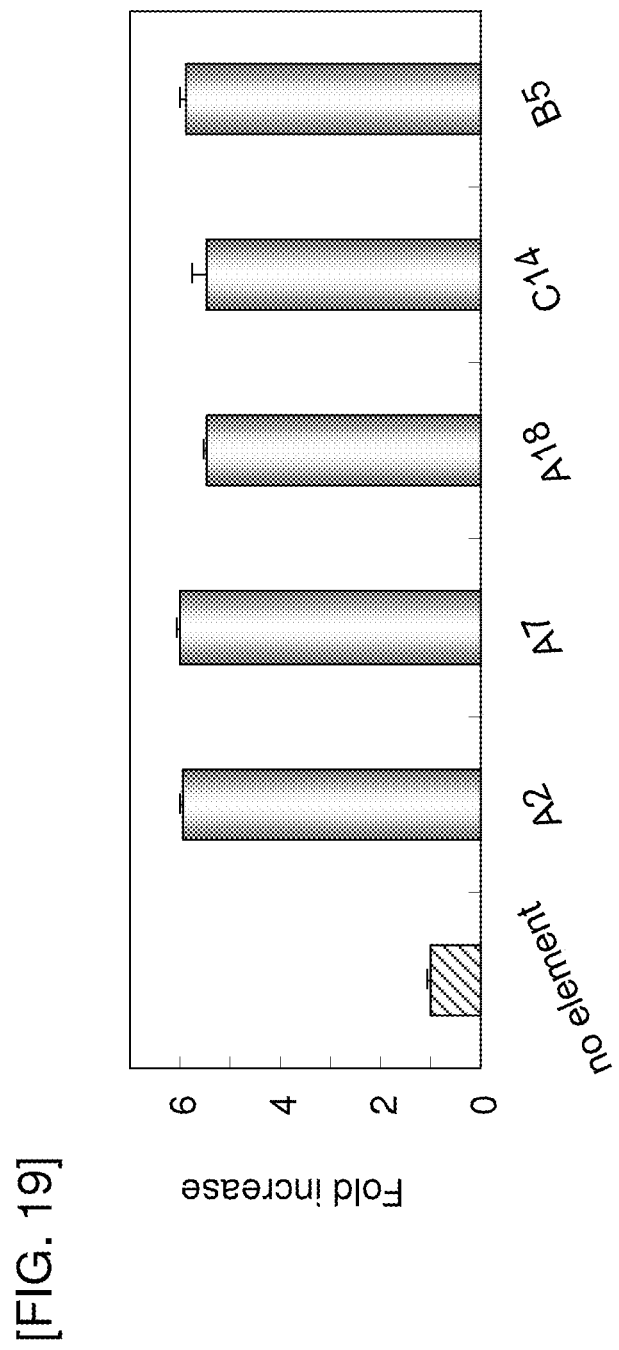

[FIG. 20]

| A2 | Start and end points on the basis of A2 | |
|---|---|---|
| | Start point | End point |
| A2 | 1 | 8450 |
| A2-1 | 1 | 3000 |
| A2-2 | 2801 | 5800 |
| A2-3 | 5401 | 8450 |
| A2-4 | 701 | 2700 |
| A2-5 | 701 | 2200 |
| A2-6 | 701 | 3700 |
| A2-7 | 2001 | 5000 |
| A2-8 | 4001 | 7000 |
| A2-9 | 1 | 3700 |
| A2-10 | 2001 | 5800 |
| A2-11 | 2801 | 7000 |
| A2-12 | 701 | 5800 |
| A2-13 | 2001 | 7000 |
| A2-14 | 2801 | 8450 |
| A2-15 | 1 | 5800 |
| A2-16 | 701 | 7000 |
| A2-17 | 2001 | 8450 |

| A7 | Start and end points on the basis of A7 | |
|---|---|---|
| | Start point | End point |
| A7 | 1 | 8420 |
| A7-1 | 601 | 3600 |
| A7-2 | 3601 | 8420 |
| A7-3 | 5401 | 8420 |
| A7-4 | 3401 | 6400 |
| A7-5 | 1501 | 4500 |
| A7-6 | 4401 | 7400 |
| A7-7 | 2401 | 5400 |
| A7-8 | 1 | 3600 |
| A7-9 | 1501 | 5400 |
| A7-10 | 2401 | 6400 |
| A7-11 | 3401 | 7400 |
| A7-12 | 4401 | 8420 |
| A7-13 | 1 | 5400 |
| A7-14 | 1501 | 6400 |
| A7-15 | 2401 | 7400 |
| A7-16 | 3401 | 8420 |
| A7-17 | 1 | 6400 |
| A7-18 | 1501 | 7400 |

| A18 | Start and end points on the basis of A18 | |
|---|---|---|
| | Start point | End point |
| A18 | 1 | 8475 |
| A18-1 | 1 | 5040 |
| A18-2 | 1001 | 6002 |
| A18-3 | 2001 | 7000 |
| A18-4 | 3000 | 7000 |

[FIG. 21]

Start and end points on the basis of B5

| B5 | Start point | End point |
|---|---|---|
| | 1 | 8401 |
| B5-1 | 1 | 4001 |
| B5-2 | 1 | 3200 |
| B5-3 | 2491 | 5601 |
| B5-4 | 5373 | 8401 |
| B5-5 | 901 | 4001 |
| B5-6 | 4001 | 7000 |

Start and end points on the basis of C14

| C14 | Start point | End point |
|---|---|---|
| | 1 | 8427 |
| C14-1 | 960 | 4015 |
| C14-2 | 1987 | 5014 |
| C14-3 | 4020 | 7119 |
| C14-4 | 960 | 8141 |
| C14-5 | 960 | 6011 |
| C14-6 | 4939 | 8141 |
| C14-7 | 960 | 5014 |
| C14-8 | 2994 | 7119 |
| C14-9 | 4020 | 8141 |
| C14-10 | 1 | 5014 |
| C14-11 | 1987 | 7119 |
| C14-12 | 2994 | 8141 |
| C14-13 | 960 | 7119 |
| C14-14 | 1987 | 8141 |

US 9,862,969 B2

PROMOTER DERIVED FROM HUMAN GENE

CROSS-REFERENCE TO RELATED APPLICATION

This application is a continuation of International Application No. PCT/JP2012/080532, filed Nov. 27, 2012, the disclosure of which is incorporated by reference herein.

STATEMENT REGARDING SEQUENCE LISTING

The sequence listing associated with this application is provided in text format in lieu of a paper copy and is hereby incorporated by reference into the specification. The name of the text file containing the sequence listing is 43753_Sequence_Substitute_2014-08-06.txt. The text file is 109 KB; was created on Aug. 6, 2014; and is being submitted via EFS-Web with the filing of the specification.

TECHNICAL FIELD

The present invention relates to a transfected mammalian host cell whose foreign protein transcriptional activity has been enhanced by using a foreign gene expression vector having a promoter derived from a human gene and a method for producing the foreign protein using the host cell.

BACKGROUND ART

Due to the development of genetic recombination techniques, the market for protein pharmaceutical products such as therapeutic proteins and antibody drugs has rapidly expanded. In particular, antibody drugs can have high specificity without causing an adverse immunoreaction when administered to the human body, and therefore, the development thereof has been actively pursued.

As a host by which a pharmaceutical protein product typified by an antibody drug is produced, a microorganism, a yeast, an insect, an animal or plant cell, a transgenic animal or plant cell, or the like can be used. In order for the pharmaceutical protein product to have biological activity or immunogenicity, post-translational modification such as folding or glycosylation is essential. Therefore, a microorganism with which complicated post-translational modification cannot be performed, or a plant having a different glycan structure, is not suitable as the host. The use of a cultured mammalian cell such as a CHO (Chinese hamster ovary) cell, which is from a species closely related to humans, is the current standard considering that such a cell has a glycan structure similar to that of humans and is safe, and post-translational modification can be performed using such a cell.

In cases where a cultured mammalian cell is used as the host, there are problems that the growth rate is low, the productivity is low, the cost is high, etc., as compared with a microorganism or the like (NPL 1). In addition, in order to use a pharmaceutical protein product clinically, it is necessary to administer a large amount of the product. Therefore, the lack of production ability thereof is another worldwide problem. When a pharmaceutical protein product is produced in a cultured mammalian cell expression system, the production cost is high as compared with a low molecular weight synthetic pharmaceutical product. Accordingly attempts have been made to reduce the production cost by improving the respective production steps. Improvement of the production amount in the cultured mammalian cell expression system is an effective method for reducing the production cost (NPL 2 and NPL 3). Accordingly, in order to improve the productivity of a foreign gene in a cultured mammalian cell, various approaches based on promoters, enhancers, antibiotic selection markers, gene amplification, culturing engineering techniques, and the like have been investigated. In cases where a CHO cell is used as a host cell to express a foreign gene, i.e., to produce a pharmaceutical protein product, a virus-derived, human cytomegalovirus major immediate early promoter (hereinafter referred to as "CMV promoter") is generally used (NPL 4, NPL 5, and NPL 6). Further, it is known that a polynucleotide upstream of the transcription start site of a human ribosomal protein gene such as RPL32 or RPS11 can be used as a DNA element for the protein expression in a CHO cell, in combination with another heterologous promoter (NPL 7 and PLT 1).

CITATION LIST

Patent Literature

PTL 1: WO 2006/123097

Non Patent Literature

NPL 1: Florian M. Wurm., Nat. Biotechnol. 22(11):1393-1398, 2004
NPL 2: Farid S S., J Chromatogr B Analyt Technol Biomed Life Sci. 848(1):8-18, 2007
NPL 3: Werner R G. Economic aspects of commercial manufacture of biopharmaceuticals. J Biotechnol. 113(1-3):171-182, 2004
NPL 4: Durocher Y et al., Curr Opin Biotechnol. 20(6):700-707, 2009
NPL 5: Boshart M et al., Cell. 41(2):521-530, 1985
NPL 6: Foecking M K et al., Gene. 45(1):101-105, 1986
NPL 7: Hoeksema F. et al., Biotechnology Research International, Volume 2011, Article ID 492875, 11 pages

SUMMARY OF THE INVENTION

Technical Problem

An object of the invention is to provide a method for increasing the production of a foreign protein to be used in a pharmaceutical protein product, using a promoter having a high activity to enhance foreign gene expression in a host cell such as a cultured mammalian cell. By identifying a promoter having a promoter activity equivalent to or higher than that of a CMV promoter in a CHO cell or the like, a method for stably achieving high foreign gene expression in a mammalian cell is provided, and a method for contributing to the improvement of production levels, in other words, reduction in the production costs of a pharmaceutical protein product in a cultured mammalian cell expression system, can be provided.

Solution to Problem

The present inventors made intensive studies in order to solve the above problems, and found that a polynucleotide starting at a nucleotide located about 2 kbp upstream of the transcription start site and ending at a nucleotide immediately upstream of a nucleotide sequence corresponding to the start codon of a human ribosomal protein gene has a high promoter activity. They found that the promoter activity can significantly improve the production of a foreign protein which is to be expressed in a cultured mammalian cell, and thus completed the invention. The invention includes the following aspects.

(1) A polynucleotide comprising a nucleotide sequence represented by SEQ ID NO: 1 in the Sequence Listing.

(2) A polynucleotide comprising a nucleotide sequence represented by SEQ ID NO: 2 in the Sequence Listing.

(3) A polynucleotide comprising a nucleotide sequence represented by SEQ ID NO: 3 in the Sequence Listing.

(4) A polynucleotide comprising a nucleotide sequence having an identity of 95% or more to the nucleotide sequence of the polynucleotide according to any one of the above (1) to (3) and having a promoter activity.

(5) A polynucleotide comprising a nucleotide sequence having an identity of 99% or more to the nucleotide sequence of the polynucleotide according to any one of the above (1) to (3) and having a promoter activity.

(6) A polynucleotide which hybridizes to a polynucleotide comprising a nucleotide sequence complementary to the nucleotide sequence of the polynucleotide according to any one of the above (1) to (3) under stringent conditions and has a promoter activity.

(7) A foreign gene expression unit comprising the polynucleotide according to any one of the above (1) to (6).

(8) The foreign gene expression unit according to the above (7), wherein the foreign gene is a gene encoding a multimeric protein.

(9) The foreign gene expression unit according to the above (7), wherein the foreign gene is a gene encoding a heteromultimeric protein.

(10) The foreign gene expression unit according to the above (7), wherein the foreign gene is a gene encoding an antibody or a functional fragment thereof.

(11) A foreign gene expression vector comprising the foreign gene expression unit according to any one of the above (7) to (10).

(12) A foreign gene expression vector comprising the foreign gene expression unit according to any one of the above (7) to (10), and one or more polynucleotides selected from polynucleotides described in (a) to (i) in the following Group A:

Group A (a) a polynucleotide comprising a nucleotide sequence represented by SEQ ID NO: 10 in the Sequence Listing;

(b) a polynucleotide comprising a nucleotide sequence represented by SEQ ID NO: 11 in the Sequence Listing;

(c) a polynucleotide comprising a nucleotide sequence represented by SEQ ID NO: 12 in the Sequence Listing;

(d) a polynucleotide comprising a nucleotide sequence represented by SEQ ID NO: 13 in the Sequence Listing;

(e) a polynucleotide comprising a nucleotide sequence represented by SEQ ID NO: 14 in the Sequence Listing;

(f) a polynucleotide comprising at least 3000 consecutive nucleotides of a nucleotide sequence represented by any one of SEQ ID NOS: 10 to 14 in the Sequence Listing;

(g) a polynucleotide comprising at least 2000 consecutive nucleotides of a nucleotide sequence represented by any one of SEQ ID NOS: 10 to 14 in the Sequence Listing;

(h) a polynucleotide comprising a polynucleotide sequence having an identity of 95% or more to the nucleotide sequence of the polynucleotide according to any one of the above (a) to (g), and having the activity of enhancing foreign gene expression; and (i) a polynucleotide comprising a nucleotide sequence having an identity of 99% or more to the nucleotide sequence of the polynucleotide according to any one of the above (a) to (g), and having the activity of enhancing foreign gene expression.

(13) A transformed cell into which the foreign gene expression vector according to the above (11) or (12) has been introduced.

(14) A transformed cell into which the foreign gene expression vector according to the above (11) or (12) and an element vector have been introduced.

(15) The transformed cell according to the above (13) or (14), wherein the cell is a cultured cell derived from a mammal.

(16) The transformed cell according to the above (15), wherein the cultured cell derived from a mammal is a COS-1 cell, a 293 cell, or a CHO cell.

(17) A method for producing a protein characterized by culturing the transformed cell according to any one of the above (13) to (16) and obtaining a protein derived from a foreign gene from the resulting culture product.

(18) Use of the polynucleotide sequence according to any one of the above (1) to (6) for expressing a foreign gene in a transformed cell.

(19) Use of the foreign gene expression vector according to the above (11) or (12) for expressing a foreign gene in a transformed cell.

Advantageous Effects of the Invention

By introducing a foreign gene expression vector using a promoter derived from a human gene of the invention into a mammalian host cell, the expression of a foreign gene of a therapeutic protein, an antibody, or the like can be significantly enhanced. Further, by using the promoter of the invention in combination with a DNA element, the expression of a foreign gene of a therapeutic protein, an antibody, or the like can be further enhanced.

BRIEF DESCRIPTION OF THE DRAWINGS

FIG. 1 shows a graph in which the activity of promoters was evaluated by using the activity of SEAP as an index in transfected CHO-K1 polyclonal cells. The graph shows the activity of SEAP for each promoter, with the value for a CMV promoter normalized to 1. The results of two independent experiments are shown (n=3, mean±SD).

FIG. 2 shows a graph in which the activity of truncated promoters was evaluated by using the activity of SEAP as an index in transfected CHO-K1 polyclonal cells. The graph shows the activity of each promoter, with the value for a CMV promoter normalized to 1 (n=3, mean±SD).

FIG. 3 shows a graph in which it was confirmed by the amplification of a GAPDH region that a sample subjected to ChIP-on-chip was chromatin-immunoprecipitated specifically with an anti-acetylated histone H3 antibody.

FIG. 4 is a schematic view of an SEAP expression vector into which a DNA element has been inserted.

FIG. 5 shows a graph in which the expression-enhancing effects of DNA elements A2, A7, A18, B5, and C14 were confirmed by using the activity of SEAP expressed by a CMV promoter as an index in a transfected CHO cell line.

FIG. 6 shows graphs in which the expression-enhancing effects of DNA elements A2 and A7 were confirmed by using the activity of SEAP expressed by an EF-1α or an SV40 promoter as an index in a transfected CHO cell line.

FIG. 7 is a schematic view of an antibody expression (antibody gene X heavy chain and light chain co-expression) vector into which a DNA element has been inserted.

FIG. 8 shows graphs in which the expression-enhancing effect of DNA element A7 was confirmed by using the level of production (measured by an ELISA method) of an antibody expressed by a CMV or an EF-1α promoter as an index in a transfected CHO cell line.

FIG. 9 is a table showing the sequence lengths of DNA element A2 and related sequences.

FIG. 10 shows graphs in which the expression-enhancing effects of DNA element A2 and related sequences were confirmed by using the activity of SEAP as an index in a transfected CHO cell line.

FIG. 11 is a table showing the sequence lengths of DNA element A7 and related sequences.

FIG. 12 shows graphs in which the expression-enhancing effects of DNA element A7 and related sequences were confirmed by using the activity of SEAP as an index in a transfected CHO cell line.

FIG. 13 is a table showing the sequence lengths of DNA element A18 and related sequences.

FIG. 14 shows a graph in which the expression-enhancing effects of DNA element A18 and related sequences were confirmed by using the activity of SEAP as an index in a transfected CHO cell line.

FIG. 15 is a table showing the sequence lengths of DNA element B5 and related sequences.

FIG. 16 shows a graph in which the expression-enhancing effects of DNA element B5 and related sequences were confirmed by using the activity of SEAP as an index in a transfected CHO cell line.

FIG. 17 is a table showing the sequence lengths of DNA element C14 and related sequences.

FIG. 18 shows graphs in which the expression-enhancing effects of DNA element C14 and related sequences were confirmed by using the activity of SEAP as an index in a transfected CHO cell line.

FIG. 19 shows a graph in which the expression-enhancing effects of DNA elements A2, A7, A18, B5, and C14 were confirmed by using the activity of SEAP as an index in a transfected HEK293 cell line.

FIG. 20 is a table showing nucleotides at the start and end points on the basis of the full-length sequence of DNA element A2, A7, or A18.

FIG. 21 is a table showing nucleotides at the start and end points on the basis of the full-length sequence of DNA element B5 or C14.

DESCRIPTION OF EMBODIMENTS

Hereinafter, the invention will be specifically described.

The term "gene" as used herein refers to a segment which is transcribed into an mRNA and then translated into a protein, and includes not only a DNA, but also an mRNA thereof, cDNA thereof, and an RNA thereof.

The term "polynucleotide" as used herein is used in the same meaning as nucleic acid and also includes DNA, RNA, probe, oligonucleotide, and primer.

The terms "polypeptide" and "protein" as used herein are used without distinction.

The term "gene expression" as used herein refers to a phenomenon in which an mRNA is transcribed from a gene and/or a phenomenon in which a protein is translated from the mRNA.

The term "foreign gene" as used herein refers to a gene which is artificially introduced into a host cell.

The term "foreign protein" as used herein refers to a protein encoded by a foreign gene.

The term "gene expression unit" as used herein refers to a polynucleotide having, in the direction of the reading frame of transcription, at least a promoter region, a foreign gene, and a transcription terminator region (poly(A) addition signal).

The term "activity to enhance foreign gene expression" as used herein refers to the activity to enhance the production of a foreign protein in a host cell by creating an environment advantageous to transcription in any DNA around the gene expression unit containing a foreign gene and significantly improving the transcription efficiency.

The term "promoter" as used herein refers to a region to which a transcription factor involved in the initiation of transcription from DNA into RNA can bind, and is sometimes referred to as "promoter region" in this description. Examples of the promoter include a polynucleotide starting at a nucleotide located about 2 kbp upstream of a transcription start site and ending at a nucleotide immediately upstream of a nucleotide sequence corresponding to the start codon, and the promoter may contain a 5'-UTR and an intron.

The term "promoter activity" as used herein refers to an activity in which a transcription factor binds to a promoter and initiates transcription to produce a protein encoded by a gene. It can be assayed by using the activity of a protein encoded by a reporter gene such as secretory alkaline phosphatase (SEAP) as an index.

The phrase "having a promoter activity" as used herein refers to having the activity of expressing SEAP equivalent to or higher than that of a CMV promoter under the same conditions as those described below (Example 3) for evaluating a promoter activity by using the expression level of SEAP as an index.

The term "DNA element" as used herein refers to a polynucleotide having the activity of enhancing foreign gene expression in cases where the polynucleotide is located in the vicinity of a gene expression unit or in a foreign gene expression vector containing a gene expression unit.

The term "functional fragment of an antibody" as used herein refers to a partial fragment of an antibody having an antigen-binding activity and includes Fab, F(ab')$_2$, and the like. However, the term is not limited to these molecules as long as the fragment has a binding affinity for an antigen.

The term "identity" as used herein refers to a relationship between the sequences of two or more nucleotide sequences or amino acid sequences determined by comparing the sequences, as known in the art. In the art, the term "identity" may also refer to the degree of sequence relatedness between nucleic acid molecules or between polypeptides as determined by the match between strings of two or more nucleotide sequences or two or more amino acid sequences. The "identity" can be evaluated by calculating the percentage of identical matches between the smallest of the two or more sequences with gapped alignments (if any) addressed by a specific mathematical model or computer program (i.e., "algorithms"). Specifically, the identity can be evaluated by using software such as Clustal W2 provided by European Molecular Biology Laboratory-European Bioinformatics Institute (EMBL-EBI), but the software is not limited thereto and any can be used as long as it is used by those skilled in the art.

The phrase "hybridized under stringent conditions" as used herein refers to hybridization under conditions in which a so-called specific hybrid is formed but a non-specific hybrid is not formed. Examples of the conditions include conditions in which a complementary strand of a nucleic acid comprising a nucleotide sequence having an identity of 80% or more, preferably 90% or more, more preferably 95% or more, most preferably 99% or more to another nucleic acid hybridizes, and a complementary strand of a nucleic acid comprising a nucleotide sequence having a lower identity does not hybridize. More specifically, it means that hybridization is effected at 68° C. in a commercially available hybridization solution ExpressHyb Hybridization Solution (manufactured by Clontech, Inc.) or hybridization is effected under conditions such that hybridization is performed at 68° C. in the presence of 0.7 to 1.0 M NaCl using a filter having DNA immobilized thereon, followed by washing at 68° C. using 0.1 to 2×SSC solution (1×SSC solution is composed of 150 mM NaCl and 15 mM sodium citrate) or under conditions equivalent thereto.

1. PROMOTER TO BE USED FOR ENHANCING FOREIGN GENE EXPRESSION

As a promoter derived from a human gene of the invention (hereinafter sometimes also referred to as a "promoter of the invention"), a polynucleotide starting at a nucleotide located about 2 kbp upstream of the transcription start site and ending at a nucleotide immediately upstream of a nucleotide sequence corresponding to the start codon of a human ribosomal protein gene is preferred. The promoter derived from a human gene may be a polynucleotide starting at a nucleotide located about 1 kbp or about 0.5 kbp upstream of the transcription start site and ending at a nucleotide immediately upstream of a nucleotide sequence corresponding to the start codon sequence of a human ribosomal protein gene.

The human ribosomal protein gene is preferably a human ribosomal protein S7 gene (hereinafter referred to as "RPS7"), a human ribosomal protein L32 gene (hereinafter referred to as "RPL32"), or a human ribosomal protein L34 gene (hereinafter referred to as "RPL34").

The promoter of the invention is preferably a promoter of RPS7, RPL32, or RPL34, more preferably a polynucleotide represented by any of SEQ ID NOS: 1 to 9 in the Sequence Listing, and particularly preferably a polynucleotide represented by any of SEQ ID NOS: 1 to 3.

The nucleotide sequences of SEQ ID NOS: 1, 2, and 3 are sequences starting at a nucleotide located about 2 kbp upstream of the transcription start site and ending at a nucleotide immediately upstream of a nucleotide sequence corresponding to the start codon of RPS7, RPL32, and RPL34, respectively. The nucleotide sequences of SEQ ID NOS: 4, 6, and 8 are sequences starting at a nucleotide located about 1 kbp upstream of the transcription start site and ending at a nucleotide immediately upstream of a nucleotide sequence corresponding to the start codon of RPS7, RPL32, and RPL34, respectively. The nucleotide sequences of SEQ ID NOS: 5, 7, and 9 are sequences starting at a nucleotide located about 0.5 kbp upstream of the transcription start site and ending at a nucleotide immediately upstream of a nucleotide sequence corresponding to the start codon of RPS7, RPL32, and RPL34, respectively.

Further, the promoter of the invention may be a polynucleotide which comprises a nucleotide sequence having an identity of 80% or more, preferably 90% or more, more preferably 95% or more, most preferably 99% or more to any one of the nucleotide sequences represented by SEQ ID NOS: 1 to 9, and has a promoter activity.

The promoter of the invention may be a polynucleotide which hybridizes to a polynucleotide, comprising a nucleotide sequence complementary to a polynucleotide comprising any one nucleotide sequence, selected from the group consisting of the nucleotide sequences represented by SEQ ID NOS: 1 to 9, under stringent conditions and has a promoter activity.

The promoter of the invention may be a polynucleotide which is a mutated polynucleotide comprising a nucleotide sequence in which one or more, preferably 1 to 300, more preferably 1 to 30 nucleotides have been deleted, substituted, and/or added in any one nucleotide sequence selected from the group consisting of the nucleotide sequences represented by SEQ ID NOS: 1 to 9, and has a promoter activity.

Introduction of a mutation (deletion, substitution, and/or addition) into the above-mentioned nucleotide sequence can be performed by a method known in the art such as a Kunkel method or a gapped duplex method, or an equivalent method. For example, a mutation introduction kit utilizing a site-directed mutagenesis method such as Mutant-K (manufactured by TaKaRa Bio, Inc.) or Mutant-G (manufactured by TaKaRa Bio, Inc.), an LA PCR in vitro Mutagenesis series kit (manufactured by TaKaRa Bio, Inc.) can be used. Such a mutated polynucleotide can also be used as the promoter of the invention.

The activity of the promoter of the invention to enhance foreign gene expression can be assayed by using the activity of a protein encoded by a reporter gene, such as SEAP, as an index. In cases where the activity of a reporter protein when using the promoter of the invention is equivalent to or higher than when using a CMV promoter, preferably, the activity being increased by 1.2 times or more, more preferably by 1.5 times or more, the promoter can be judged to have the activity of enhancing foreign gene expression. Even in cases where the activity is increased by about 1.2 times or more, it is expected that this will reduce the cell culture scale, the cell culture time, and the purification step, making it possible to increase the yield and reduce the cell culture cost. If the yield is increased, then it is possible to supply stably a foreign protein to be used as a pharmaceutical product. In addition, if the cell culture cost is reduced, the cost for the foreign protein to be used as a pharmaceutical product is reduced.

Further, the promoter of the invention can also be used for enhancing the expression of an endogenous gene of a host cell by introducing the promoter into the host cell using a method well known to those skilled in the art.

2. FOREIGN GENE EXPRESSION UNIT

The foreign gene expression unit of the invention (hereinafter sometimes also referred to as "gene expression unit of the invention") has, in the direction of the reading frame of transcription, at least the promoter of the invention described in the above item "1", a foreign gene, and a transcription terminator region (poly(A) addition signal).

Further, the poly(A) addition sequence may be a sequence having the activity to cause transcription termination for the transcription from the promoter, and may be a sequence from a gene identical to or different from that of the promoter.

3. DNA ELEMENT TO BE USED FOR ENHANCING FOREIGN GENE EXPRESSION

By using the gene expression unit of the invention described in the above item "2" and a DNA element in combination, the expression of a foreign gene can be further enhanced. The DNA element to be used in combination can be obtained by using the interaction between acetylated histone H3 and the element as an index as described in Example 6. In general, it is said that the acetylation of histones (H3 and H4) is associated with the activation of transcription, and two major theories have been advocated. One theory is that the acetylation of histones is associated with a change in nucleosome conformation in such a manner that histone tails are acetylated so as to be electrically neutralized, weakening DNA-histone interactions (Mellor J. (2006) Dynamic nucleosomes and gene transcription. Trends Genet. 22(6): 320-329). The other theory is that the acetylation of histones is associated with the recruitment of various transcription factors (Nakatani Y. (2001) Histone acetylases-versatile players. Genes Cells. 6(2): 79-86). According to either theory, there is a high possibility that the acetylation of histones is associated with the activation of transcription, and by performing chromatin immunoprecipitation (ChIP) using an anti-acetylated histone H3 antibody, it is possible to concentrate a DNA element that interacts with acetylated histone H3.

A2 is an example of the DNA element to be used in combination with the promoter of the invention for enhancing foreign gene expression. A2 is located in the region from 80966429 to 80974878 of human chromosome 15 and is an 8450 bp polynucleotide having an AT content of 62.2%. The nucleotide sequence of A2 is represented by SEQ ID NO: 10 in the Sequence Listing.

A7, A18, B5, and C14 are examples of similar DNA elements. A7 is located in the region from 88992123 to 89000542 of human chromosome 11 and is an 8420 bp polynucleotide having an AT content of 64.52%. The nucleotide sequence of A7 is represented by SEQ ID NO: 11 in the Sequence Listing.

A18 is located in the region from 111275976 to 111284450 of human chromosome 4 and is an 8475 bp polynucleotide having an AT content of 62.54%. The nucleotide sequence of A18 is represented by SEQ ID NO: 12 in the Sequence Listing.

B5 is located in the region from 143034684 to 143043084 of human chromosome 1 and is an 8401 bp polynucleotide having an AT content of 66.37%. The nucleotide sequence of B5 is represented by SEQ ID NO: 13 in the Sequence Listing.

Finally, C14 is located in the region from 46089056 to 46097482 of human chromosome 11 and is an 8427 bp polynucleotide having an AT content of 63.81%. The nucleotide sequence of C14 is represented by SEQ ID NO: 14 in the Sequence Listing.

The activity of enhancing foreign gene expression of the DNA element to be used in combination with the promoter of the invention can be assayed by using the activity of a protein encoded by a reporter gene such as SEAP as an index.

In cases where the DNA element is used in combination with the promoter of the invention, any one of the above DNA elements may be used alone, or two or more copies of one type of the DNA element may be used. Alternatively, two or more different types of the above DNA elements may be used in combination.

A2, A7, A18, B5, and C14 are preferred examples of the DNA element to be used in combination with the promoter of the invention.

The DNA element to be used in the invention may be a nucleotide sequence which comprises a nucleotide sequence having an identity of 80% or more, preferably 90% or more, more preferably 95% or more, most preferably 99% or more to any of the nucleotide sequences represented by SEQ ID NOS: 10 to 14 and has the activity of enhancing foreign gene expression. The nucleotide sequence homology search can be performed against, for example, the DNA Databank of Japan or the like using a program such as FASTA or BLAST.

The DNA element to be used in combination with the promoter of the invention may be a DNA element which hybridizes to a polynucleotide comprising a nucleotide sequence complementary to a polynucleotide comprising a nucleotide sequence selected from the group consisting of the nucleotide sequences represented by SEQ ID NOS: 10 to 14 under stringent conditions and has the activity of enhancing foreign gene expression.

A person skilled in the art can easily obtain such a homologue gene with reference to Molecular Cloning (Sambrook, J. et al., Molecular Cloning: a Laboratory Manual 2nd ed., Cold Spring Harbor Laboratory Press, 10 Skyline Drive Plainview, N.Y. (1989)), or the like. Further, the identity of the above-mentioned nucleotide sequence can be determined by a FASTA search or BLAST search in the same manner.

Introduction of a mutation (deletion, substitution, and/or addition) into the above-mentioned polynucleotide can be performed by a method known in the art such as a Kunkel method or a gapped duplex method, or an equivalent method. For example, a mutation introduction kit utilizing a site-directed mutagenesis method such as Mutant-K (manufactured by TaKaRa Bio, Inc.), Mutant-G (manufactured by TaKaRa Bio, Inc.), or an LA PCR in vitro Mutagenesis series kit (manufactured by TaKaRa Bio, Inc.), or the like can be used. Such a mutated polynucleotide can also be used as the DNA element of the invention.

As the DNA element to be used in combination with the promoter of the invention, a partial fragment comprising at least 3000 or at least 2000 consecutive nucleotides of a nucleotide sequence represented by any one of SEQ ID NOS: 10 to 14 in the Sequence Listing can be used. Examples of such a partial fragment include: A2-1 to A2-17 which are partial fragments of A2; A7-1 to A7-18 which are partial fragments of A7; A18-1 to A18-4 which are partial fragments of A18; B5-1 to B5-6 which are partial fragments of B5; and C14-1 to C14-14 which are partial fragments of C14. However, the DNA element is not limited to these partial fragments as long as it has the activity of enhancing foreign gene expression.

In the invention, any one of the above partial fragments may be used alone, and also two or more copies of one type of the partial fragment may be used. Alternatively, two or more different types of the partial fragments may be used in combination. Further, a full-length sequence and a partial fragment of any of the above-mentioned DNA elements may be used in combination. In the above combination, the full-length sequence and the partial fragment may be derived from the same DNA element or from different DNA elements.

As for the polynucleotide sequences of the respective fragments of A2, A2-1 corresponds to the polynucleotide sequence of nucleotides 1 to 3000 of SEQ ID NO: 10 in the Sequence Listing; A2-2 corresponds to the polynucleotide sequence of nucleotides 2801 to 5800 of SEQ ID NO: 10 in the Sequence Listing; A2-3 corresponds to the polynucleotide sequence of nucleotides 5401 to 8450 of SEQ ID NO: 10 in the Sequence Listing; A2-4 corresponds to the polynucleotide sequence of nucleotides 701 to 2700 of SEQ ID NO: 10 in the Sequence Listing; A2-5 corresponds to the polynucleotide sequence of nucleotides 701 to 2200 of SEQ ID NO: 10 in the Sequence Listing; A2-6 corresponds to the polynucleotide sequence of nucleotides 701 to 3700 of SEQ ID NO: 10 in the Sequence Listing; A2-7 corresponds to the polynucleotide sequence of nucleotides 2001 to 5000 of SEQ ID NO: 10 in the Sequence Listing; A2-8 corresponds to the polynucleotide sequence of nucleotides 4001 to 7000 of SEQ ID NO: 10 in the Sequence Listing; A2-9 corresponds to the polynucleotide sequence of nucleotides 1 to 3700 of SEQ ID NO: 10 in the Sequence Listing; A2-10 corresponds to the polynucleotide sequence of nucleotides 2001 to 5800 of SEQ ID NO: 10 in the Sequence Listing; A2-11 corresponds to the polynucleotide sequence of nucleotides 2801 to 7000 of SEQ ID NO: 10 in the Sequence Listing; A2-12 corresponds to the polynucleotide sequence of nucleotides 701 to 5800 of SEQ ID NO: 10 in the Sequence Listing; A2-13 corresponds to the polynucleotide sequence of nucleotides 2001 to 7000 of SEQ ID NO: 10 in the Sequence Listing; A2-14 corresponds to the polynucleotide sequence of nucleotides 2801 to 8450 of SEQ ID NO: 10 in the Sequence Listing; A2-15 corresponds to the polynucleotide sequence of nucleotides 1 to 5800 of SEQ ID NO: 10 in the Sequence Listing; A2-16 corresponds to the polynucleotide sequence of nucleotides 701 to 7000 of SEQ ID NO: 10 in the Sequence Listing; and A2-17 corresponds to the polynucleotide sequence of nucleotides 2001 to 8450 of SEQ ID NO: 10 in the Sequence Listing.

As for the polynucleotide sequences of the respective fragments of A7, A7-1 corresponds to the polynucleotide sequence of nucleotides 601 to 3600 of SEQ ID NO: 11 in the Sequence Listing; A7-2 corresponds to the polynucleotide sequence of nucleotides 3601 to 8420 of SEQ ID NO: 11 in the Sequence Listing; A7-3 corresponds to the polynucleotide sequence of nucleotides 5401 to 8420 of SEQ ID NO: 11 in the Sequence Listing; A7-4 corresponds to the polynucleotide sequence of nucleotides 3401 to 6400 of SEQ ID NO: 11 in the Sequence Listing; A7-5 corresponds to the polynucleotide sequence of nucleotides 1501 to 4500 of SEQ ID NO: 11 in the Sequence Listing; A7-6 corresponds to the polynucleotide sequence of nucleotides 4401 to 7400 of SEQ ID NO: 11 in the Sequence Listing; A7-7 corresponds to the polynucleotide sequence of nucleotides 2401 to 5400 of SEQ ID NO: 11 in the Sequence Listing; A7-8 corresponds to the polynucleotide sequence of nucleotides 1 to 3600 of SEQ ID NO: 11 in the Sequence Listing; A7-9 corresponds to the polynucleotide sequence of nucleotides 1501 to 5400 of SEQ ID NO: 11 in the Sequence Listing; A7-10 corresponds to the polynucleotide sequence of nucleotides 2401 to 6400 of SEQ ID NO: 11 in the Sequence Listing; A7-11 corresponds to the polynucleotide sequence of nucleotides 3401 to 7400 of SEQ ID NO: 11 in the Sequence Listing; A7-12 corresponds to the polynucleotide sequence of nucleotides 4401 to 8420 of SEQ ID NO: 11 in the Sequence Listing; A7-13 corresponds to the polynucleotide sequence of nucleotides 1 to 5400 of SEQ ID NO: 11 in the Sequence Listing; A7-14 corresponds to the polynucleotide sequence of nucleotides 1501 to 6400 of SEQ ID NO: 11 in the Sequence Listing; A7-15 corresponds to the polynucleotide sequence of nucleotides 2401 to 7400 of SEQ ID NO: 11 in the Sequence Listing; A7-16 corresponds to the polynucleotide sequence of nucleotides 3401 to 8420 of SEQ ID NO: 11 in the Sequence Listing; A7-17 corresponds to the polynucleotide sequence of nucleotides 1 to 6400 of SEQ ID NO: 11 in the Sequence Listing; and A7-18 corresponds to the polynucleotide sequence of nucleotides 1501 to 7400 of SEQ ID NO: 11 in the Sequence Listing.

As for the polynucleotide sequences of the respective fragments of A18, A18-1 corresponds to the polynucleotide sequence of nucleotides 1 to 5040 of SEQ ID NO: 12 in the Sequence Listing; A18-2 corresponds to the polynucleotide sequence of nucleotides 1001 to 6002 of SEQ ID NO: 12 in the Sequence Listing; A18-3 corresponds to the polynucleotide sequence of nucleotides 2001 to 7000 of SEQ ID NO: 12 in the Sequence Listing; and A18-4 corresponds to the polynucleotide sequence of nucleotides 3000 to 7000 of SEQ ID NO: 12 in the Sequence Listing.

As for the polynucleotide sequences of the respective fragments of B5, B5-1 corresponds to the polynucleotide sequence of nucleotides 1 to 4001 of SEQ ID NO: 13 in the Sequence Listing; B5-2 corresponds to the polynucleotide sequence of nucleotides 1 to 3200 of SEQ ID NO: 13 in the Sequence Listing; B5-3 corresponds to the polynucleotide sequence of nucleotides 2491 to 5601 of SEQ ID NO: 13 in the Sequence Listing; B5-4 corresponds to the polynucleotide sequence of nucleotides 5373 to 8401 of SEQ ID NO: 13 in the Sequence Listing; B5-5 corresponds to the polynucleotide sequence of nucleotides 901 to 4001 of SEQ ID NO: 13 in the Sequence Listing; and B5-6 corresponds to the polynucleotide sequence of nucleotides 4001 to 7000 of SEQ ID NO: 13 in the Sequence Listing.

As for the polynucleotide sequences of the respective fragments of C14, C14-1 corresponds to the polynucleotide sequence of nucleotides 960 to 4015 of SEQ ID NO: 14 in the Sequence Listing; C14-2 corresponds to the polynucleotide sequence of nucleotides 1987 to 5014 of SEQ ID NO: 14 in the Sequence Listing; C14-3 corresponds to the polynucleotide sequence of nucleotides 4020 to 7119 of SEQ ID NO: 14 in the Sequence Listing; C14-4 corresponds to the polynucleotide sequence of nucleotides 960 to 8141 of SEQ ID NO: 14 in the Sequence Listing; C14-5 corresponds to the polynucleotide sequence of nucleotides 960 to 6011 of SEQ ID NO: 14 in the Sequence Listing; C14-6 corresponds to the polynucleotide sequence of nucleotides 4939 to 8141 of SEQ ID NO: 14 in the Sequence Listing; C14-7 corresponds to the polynucleotide sequence of nucleotides 960 to 5014 of SEQ ID NO: 14 in the Sequence Listing; C14-8 corresponds to the polynucleotide sequence of nucleotides 2994 to 7119 of SEQ ID NO: 14 in the Sequence Listing; C14-9 corresponds to the polynucleotide sequence of nucleotides 4020 to 8141 of SEQ ID NO: 14 in the Sequence Listing; C14-10 corresponds to the polynucleotide sequence of nucleotides 1 to 5014 of SEQ ID NO: 14 in the Sequence Listing; C14-11 corresponds to the polynucleotide sequence of nucleotides 1987 to 7119 of SEQ ID NO: 14 in the Sequence Listing; C14-12 corresponds to the polynucleotide sequence of nucleotides 2994 to 8141 of SEQ ID NO: 14 in the Sequence Listing; C14-13 corresponds to the polynucleotide sequence of nucleotides 960 to 7119 of SEQ ID NO: 14 in the Sequence Listing; and C14-14 corresponds to the polynucleotide sequence of nucleotides 1987 to 8141 of SEQ ID NO: 14 in the Sequence Listing.

4. ACQUISITION OF POLYNUCLEOTIDE

In the invention, a polynucleotide containing a foreign gene encoding a foreign protein, the production of which is to be increased, which will be described later, can be obtained by common procedures as described below. For example, such a polynucleotide can be isolated by screening a cDNA library derived from cells or tissues expressing the foreign gene using a DNA probe synthesized from a fragment of the foreign gene. mRNA therefore can be prepared by methods commonly used in the art. For example, the cells or tissues are treated with a guanidine reagent, a phenol reagent, etc., thereby obtaining total RNA, and thereafter, poly(A)+RNA (mRNA) is obtained by an affinity column method using an oligo(dT) cellulose column or a poly U-Sepharose column containing Sepharose 2B, or the like, as a carrier or by a batch method. Also, the poly(A)+RNA may further be fractionated by sucrose density-gradient centrifugation or the like. Then, single-stranded cDNA is synthesized using the thus obtained mRNA as a template, oligo dT primers, and a reverse transcriptase. From the thus obtained single-stranded cDNA, double-stranded cDNA is synthesized using DNA polymerase I, DNA ligase, RNase H, and the like. The thus synthesized double-stranded cDNA is blunted using T4 DNA polymerase, followed by ligation to an adapter (such as EcoRI adapter), phosphorylation, and the like, and the resulting DNA is incorporated into a lambda phage such as λgt11 to achieve in vivo packaging, whereby a cDNA library is prepared. It is also possible to prepare a cDNA library using a plasmid vector instead of lambda phages. Thereafter, a clone containing the target DNA (a positive clone) may be selected from the cDNA library.

In cases where the above-mentioned promoter, a polynucleotide containing a terminator region, the above-mentioned DNA element, or a polynucleotide containing a foreign gene to be used for producing a protein is isolated from genomic DNA, according to a common procedure (Molecular Cloning (1989), Methods in Enzymology 194 (1991)), genomic DNA is extracted from a cell line of an organism to be used as a collection source, and the polynucleotide is selected and isolated. The extraction of genomic DNA can be performed according to, for example, the method of Cryer et al. (Methods in Cell Biology, 12, 39-44 (1975)) or the method of P. Philippsen et al. (Methods Enzymol., 194, 169-182 (1991)).

The target promoter, DNA element, or polynucleotide containing a foreign gene can also be obtained by, for example, the PCR method (PCR Technology. Henry A. Erlich, Stockton press (1989)). In the amplification of a polynucleotide using the PCR method, 20- to 30-mer synthetic single-stranded DNAs are used as primers and genomic DNA is used as a template. The amplified gene is used after the polynucleotide sequence of the gene is confirmed. As the template for PCR, a genomic DNA library such as a bacterial artificial chromosome (BAC)-library can be used.

On the other hand, the polynucleotide containing a foreign gene whose sequence is not known can be obtained by (a) preparing a gene library according to a common procedure, and (b) selecting a desired polynucleotide from the prepared gene library and amplifying the polynucleotide. The gene library can be prepared by partially digesting chromosomal DNA obtained by a common procedure from a cell line of an organism to be used as a collection source using an appropriate restriction enzyme to fragment the chromosomal DNA, ligating the obtained fragments to an appropriate vector, and introducing the vector into an appropriate host. The gene library can also be prepared by extracting mRNA from the cells, synthesizing cDNA from the mRNA, ligating the cDNA to an appropriate vector, and introducing the vector into an appropriate host. As the vector to be used in such preparation, a plasmid generally known as a vector for gene library preparation can be used, and also a phage vector, a cosmid, or the like can be used. As the host to be transformed or transfected, a host suitable for the type of the above-mentioned vector may be used. The polynucleotide containing the foreign gene is selected from the above-mentioned gene library by a colony hybridization method, a plaque hybridization method, or the like using a labeled probe containing a sequence specific for the foreign gene.

Further, the polynucleotide containing the foreign gene can also be produced by total chemical synthesis. For example, the gene can be synthesized by a method in which two pairs of complementary oligonucleotides are prepared and annealed, a method in which several annealed DNA strands are ligated by a DNA ligase, a method in which several partially complementary oligonucleotides are prepared and gaps are filled by PCR, or the like.

The determination of a polynucleotide sequence can be performed by a conventional technique, for example, a dideoxy method (Sanger et al., Proc. Natl. Acad. Sci., USA, 74, 5463-5467 (1977)), or the like. Further, the above determination of a polynucleotide sequence can also be easily performed using a commercially available sequencing kit or the like.

5. FOREIGN GENE EXPRESSION VECTOR, ELEMENT VECTOR

As a foreign gene expression vector of the invention, a vector containing the foreign gene expression unit described in the above item "2" containing the promoter of the invention described in the above item "1" is provided. The foreign gene expression vector of the invention may contain one type of the DNA elements described in the above item "3", two or more copies of one type of the above-mentioned DNA elements, or two or more different types of the above-mentioned DNA elements in combination. When a foreign gene is expressed in a host cell using the above-mentioned foreign gene expression vector, the DNA element may be located immediately upstream or downstream of the gene expression unit, or may be located at a position away from the gene expression unit. Further, one foreign gene expression vector containing a plurality of such DNA elements may be used. Incidentally, the DNA element may be inserted in either forward or reverse orientation with respect to the gene expression unit.

Further, as the vector to be used in the invention, a vector containing one type of the above-mentioned DNA elements, two or more copies of one type of the above-mentioned DNA elements, or two or more different types of the above-mentioned DNA elements in combination, and containing no gene expression unit (hereinafter referred to as an "element vector") is also included. Such an element vector can be used in combination with the above-mentioned foreign gene expression vector containing the DNA element or a foreign gene expression vector containing no DNA element and containing only the foreign gene expression unit. By allowing the element vector to coexist with the foreign gene expression vector, the expression of the foreign gene is enhanced as compared with cases where the foreign gene expression vector is used alone and, therefore, the combination of the above-mentioned vectors is also included within the foreign gene expression vector of the invention.

The foreign gene is not particularly limited, but examples thereof include reporter genes such as the genes of secretory alkaline phosphatase (SEAP), a green fluorescent protein (GFP), and luciferase; various enzyme genes such as an α-amylase gene and an α-galactosidase gene; genes of various interferons which are pharmaceutically useful and physiologically active proteins such as interferon α and interferon γ; genes of various interleukins such as IL-1 and IL-2; various cytokine genes such as an erythropoietin (EPO) gene and a granulocyte colony-stimulating factor (G-CSF) gene; a growth factor gene; and a gene encoding a multimeric protein such as a gene encoding a heteromultimer which is an antibody or a functional fragment thereof.

These genes may be obtained by any method.

The "functional fragment of an antibody" refers to a partial fragment of an antibody having an antigen-binding activity and includes Fab, F(ab')2, Fv, scFv, diabodies, linear antibodies, polyspecific antibodies formed from antibody fragments, and the like. The functional fragment of an antibody also includes Fab' which is a monovalent fragment of a variable region of an antibody obtained by treating F(ab')2 under reducing conditions. However, the functional fragment is not limited to these molecules as long as the fragment has a binding affinity for an antigen. Further, these functional fragments include not only a fragment obtained by treating a full-length molecule of an antibody protein with an appropriate enzyme, but also a protein produced in an appropriate host cell using a genetically modified antibody gene.

Further, the foreign gene expression vector and the element vector of the invention can each contain a selection marker for selecting a transformant. By using, for example, an antibiotic resistant marker which imparts resistance to an antibiotic such as cerulenin, aureobasidin, Zeocin, canavanine, cycloheximide, hygromycin, puromycin, blasticidin, tetracycline, kanamycin, ampicillin, or neomycin, a transformant can be selected. Further, where a gene which imparts resistance to a solvent such as ethanol, resistance to the osmotic pressure of glycerol, a salt, or the like, resistance to a metal ion such as a copper ion, or the like is used as a marker, a transformant can also be selected.

The foreign gene expression vector and the element vector of the invention may each be a vector which is not incorporated into the chromosomal DNA. In general, the foreign gene expression vector is transfected into a host cell, and thereafter randomly incorporated into the chromosome. However, by using a constituent component derived from a mammalian virus such as simian virus 40 (SV40), a papillomavirus (BPV, HPV), or EBV, the vector can be used as an episomal vector which is self-replicable in the transfected host cell. For example, a vector containing an SV40-derived replication origin and a sequence encoding an SV40 large T antigen which is a trans-acting factor, a vector containing an EBV-derived oriP and a sequence encoding EBNA-1, and the like are widely used. The DNA element can effectively exhibit the activity of enhancing foreign gene expression regardless of the type of vector or the presence or absence of incorporation thereof into the chromosome.

6. TRANSFORMED CELL

The transformed cell of the invention is a transformed cell into which the foreign gene expression vector described in the above item "5" has been introduced. As the foreign gene expression vector, (A) only a foreign gene expression vector containing no DNA element may be introduced, or (B) a foreign gene expression vector containing no DNA element and an element vector may be introduced in combination. Alternatively, (C) a foreign gene expression vector containing a DNA element may be introduced, or (D) a foreign gene expression vector containing a DNA element and an element vector may be introduced in combination.

The expression of a foreign gene in a host cell by the combination described in the above (B) or (D) can be performed according to, for example, the method of Girod et al. (Biotechnology and Bioengineering, 91: 2-11 (2005)) and the method of Otte et al. (Biotechnol. Prog., 23: 801-807 (2007)).

Examples of the host cell to be transformed include a eukaryotic cell, preferred examples thereof include a mammalian cell, and more preferred examples include a cell derived from humans, mice, rats, hamsters, monkeys, or cattle. Examples of such a mammalian cell include a COS-1 cell, a 293 cell, and a CHO cell (CHO-K1, DG44, CHO dhfr-, CHO-S), but the host cell is not limited thereto.

In the invention, any method may be used for introducing the expression vector into the host cell as long as the method allows the introduced gene to be stably present in the host cell and to be adequately expressed therein. Examples of the method which is generally used include a calcium phosphate method (Ito et al., (1984) Agric. Biol. Chem., 48: 341), an electroporation method (Becker, D. M. et al., 1990, Methods. Enzymol., 194: 182-187), a spheroplast method (Creggh et al., Mol. Cell. Biol., 5: 3376 (1985)), a lithium acetate method (Ito, H. (1983) J. Bacteriol. 153: 163-168), and a lipofection method.

7. METHOD FOR PRODUCING FOREIGN PROTEIN

In the invention, a foreign protein can be produced by culturing the transformed cell described in the above item "6", into which a gene encoding the foreign protein has been introduced, by a known method, collecting the protein from the resulting culture product, followed by purification of the protein. The term "culture product" as used herein refers to cultured cells or a cell homogenate in addition to a culture supernatant. Incidentally, as the foreign protein which can be produced using the transformed cell described in the above item "6", not only a monomeric protein, but also a multimeric protein can be selected. In cases where a heteromultimeric protein formed of a plurality of different subunits is produced, it is necessary to introduce a plurality of genes encoding these subunits into the host cell described in the above item "6", respectively.

The method for culturing the transformed cell can be performed according to conventional methods for culturing host cells.

In cases where the transformed cell is a mammalian cell, the cell is cultured under conditions of, for example, 37° C. and 5% or 8% $CO_2$ for a culture time of about 24 to 1000 hours. The culturing can be performed through batch culture, fed-batch culture, continuous culture, or the like under static, shaking, stirring, or aeration conditions.

The confirmation of the expression product of the gene encoding the foreign protein from the above-mentioned culture product (culture solution) can be performed by SDS-PAGE, a Western analysis, ELISA, or the like. In order to isolate and purify the produced protein, a conventional protein isolation and purification method may be used. After completion of the culturing, in cases where the target protein is produced in the cells, the cells are homogenized using an ultrasonic homogenizer, a French press, a Manton-Gaulin homogenizer, DYNO-MILL, or the like, thereby obtaining the target protein. Further, in cases where the target protein is produced outside the cells, the culture solution is used as such, or the cells are removed by centrifugation or the like. Thereafter, the target protein is collected by extraction or the like using an organic solvent, and then the collected target protein may be isolated and purified by using techniques such as various chromatography techniques (hydrophobic chromatography, reverse-phase chromatography, affinity chromatography, ion exchange chromatography, etc.), gel filtration using a molecular sieve, or electrophoresis using a polyacrylamide gel or the like, alone or in combination according to need.

The above-mentioned culturing methods and purification methods are only examples, and the methods are not limited thereto. The amino acid sequence of the purified gene product can be confirmed by a known amino acid analysis technique such as automated amino acid sequencing using the Edman degradation method.

8. METHOD FOR PRODUCING ANTIBODY PROTEIN

As the heteromultimeric protein to be produced using the production method described in the above item "7", an antibody protein can be exemplified. The antibody protein is a tetrameric protein comprising two molecules of heavy chain polypeptides and two molecules of light chain polypeptides. Accordingly, in order to obtain such an antibody protein in a state of maintaining an antigen-binding affinity, it is necessary to introduce both heavy and light chain genes into the transformed cell described in the above item "6". In this case, the heavy and light chain gene expression units may be present on the same expression vector or different expression vectors.

As the antibody to be produced in the invention, an antibody prepared by immunizing an experimental animal such as a rabbit, a mouse, or a rat with a desired antigen can be exemplified. Further, a chimeric antibody and a humanized antibody obtained by using the above-mentioned antibody as a starting material can be also exemplified as the antibody to be produced in the invention. Further, a human antibody obtained using a genetically modified animal or a phage display method is also included in the antibody to be produced in the invention.

The antibody gene to be used for the production of the antibody is not limited to an antibody gene having a specific polynucleotide sequence as long as the combination of the heavy chain polypeptide and the light chain polypeptide to be transcribed and translated from the antibody gene has the activity of binding to a given antigen protein.

Further, it is not necessary that the antibody gene encodes the full-length molecule of the antibody, and a gene encoding a functional fragment of the antibody can be used. Such a gene encoding a functional fragment thereof can be obtained by genetically modifying a gene encoding the full-length molecule of an antibody protein.

9. PRODUCTION METHOD FOR OTHER FOREIGN PROTEINS

Examples of the foreign protein to be produced using the production method of the invention include, in addition to the above-mentioned antibodies, various proteins derived from humans or non-humans, functional fragments thereof, and modified products thereof. Examples of such proteins and the like include peptide hormones such as atrial natriuretic peptide (ANP), brain natriuretic peptide (BNP), C-type natriuretic peptide (CNP), vasopressin, somatostatin, growth hormone (GH), insulin, oxytocin, ghrelin, leptin, adiponectin, renin, calcitonin, osteoprotegerin, and insulin-like growth factor (IGF); cytokines such as interleukin, chemokine, interferon, tumor necrosis factors (such as TNF-α, TNF-β, and TNF super family), nerve growth factors (such as NGF), cell growth factors (such as EGF, FGF, PDGF, HGF, and TGF), hematopoietic growth factors (such as CSF, G-CSF, and erythropoietin), and adipokine; receptors such as TNF receptors; enzymes such as lysozyme, protease, proteinase, and peptidase; functional fragments thereof (fragments having part or all of the biological activity of the original protein), and fusion proteins comprising any of these proteins. However, the proteins are not limited thereto.

10. EXAMPLES

Hereinafter, the invention will be specifically described with reference to the Examples. However, these Examples do not limit the technical scope of the invention. The plasmids, restriction enzymes, DNA modification enzymes, and the like to be used in the Examples of the invention are commercially available products and can be used according to common procedures. Further, procedures used for DNA cloning, polynucleotide sequencing, transformation of a host cell, culturing of a transformed host cell, collection of a protein from the resulting culture product, purification of a protein, and the like are also well known to those skilled in the art or can be found in the literature.

Example 1

Construction of Vector CMV/pSeapIRESpuro for Use in Evaluation of Promoter Activity The evaluation of promoter activity was performed by using the expression of SEAP as an index, and a vector for use in the evaluation was constructed.
1-1) Amplification of cDNA of SEAP by PCR and Addition of Restriction Enzyme Site The cDNA of SEAP was amplified by PCR using primers in which an NheI site was added immediately upstream of the start codon ATG, and a BglII site was added immediately downstream of the stop codon and KOD-Plus-(TOYOBO). As a template, pSEAP2-control (Clontech) was used. The obtained fragment was digested with NheI and BglII, and then purified using a MinElute Reaction Kit (Qiagen).

```
The used primers:
                                        (SEQ ID NO: 17)
SEAPF: AAAGCTAGCATGCTGCTGCTGCTGCTGCTGGGCC (SEQ ID NO: 18)
SEAPR: AAAAGATCTTCATGTCTGCTCGAAGCGGCCGGCCGC
```

1-2) Construction of CMV/pSeapIRESpuro
After a pIRESpuro3 (Clontech) vector was digested with NheI and BamHI, the SEAP fragment prepared in 1-1) was integrated thereinto by a ligation reaction. The obtained plasmid was named "CMV/pSeapIRESpuro".

Example 2

Cloning of Promoter Regions of RPS7, RPL32, and RPL34

As human genes considered to contain a promoter having a high transcriptional activity, EEF2, YBX1, PPIA, PSAP, RAN, RPL32, RPL34, RPLP1, RPS7, RPS24, TMSB4X, UBC, YWHAE, ARPC2, and SERBP1 were selected by using mRNA level as an index, and cloning of the promoter region of each gene was performed. The obtained plasmids were used for the evaluation of promoter activity in Example 3.

2-1) Cloning of Promoter Region of RPS7

As the promoter region of RPS7, with reference to the mRNA sequence registered under accession number NM_001011.3 in GenBank, a sequence starting at a nucleotide located about 2 kbp upstream of the transcription start site and ending at a nucleotide immediately upstream of the nucleotide sequence corresponding to the start codon sequence of RPS7 was used.

The promoter region of RPS7 was amplified by PCR using *E. coli* artificial chromosome clone RP11-644P19 (GenoTechs) as a template, and also using the following primer set and KOD-Plus-(TOYOBO), and then purified using MinElute Reaction Kit (Qiagen). After CMV/pSeapIRESpuro was digested with SpeI and NheI and the CMV promoter was removed, the promoter region of RPS7 was integrated at the SpeI-NheI site using an In-Fusion Advantage PCR Cloning Kit (Clontech), whereby RPS7/pSeapIRESpuro was constructed. The nucleotide sequence of the cloned promoter region of RPS7 is represented by SEQ ID NO: 1 in the Sequence Listing.

```
Primer Set for RPS7:
RPS7-F:
                                        (SEQ ID NO: 19)
TTGATTATTGACTAGTATTTATGTATATTAACAGCACATTAACAGC RPS7-R:
                                        (SEQ ID NO: 20)
GCAGCAGCATGCTAGCGGCTTTCTCCTGGGAGAACTGAAGGCACAGCGG
```

2-2) Cloning of Promoter Region of RPL32

As the promoter region of RPL32, with reference to the mRNA sequence registered under accession number NM_000994.3 in GenBank, a sequence starting at a nucleotide located about 2 kbp upstream of the transcription start site and ending at the nucleotide immediately upstream of the nucleotide sequence corresponding to the start codon sequence of RPL32 was used.

The promoter region of RPL32 was amplified by PCR using *E. coli* artificial chromosome clone RP11-767C1 (GenoTechs) as a template, and also using the following primer set and KOD-Plus-(TOYOBO), and then purified using a MinElute Reaction Kit (Qiagen). After CMV/pSeapIRESpuro was digested with SpeI and NheI and the CMV promoter was removed, the promoter region of RPL32 was integrated at the SpeI-NheI site using an In-Fusion Advantage PCR Cloning Kit (Clontech), whereby RPL32/pSeapIRESpuro was constructed. The nucleotide sequence of the cloned promoter region of RPL32 is represented by SEQ ID NO: 2 in the Sequence Listing.

```
Primer Set for RPL32:
RPL32-F:
                                        (SEQ ID NO: 21)
TTGATTATTGACTAGTCTAAAGTGATTCCTAAAGAATTCTTCCC RPL32-R:
                                        (SEQ ID NO: 22)
GCAGCAGCATGCTAGCGATGCCTTTTGGGGAAGAAGCGGCCCC
```

2-3) Cloning of Promoter Region of RPL34

As the promoter region of RPL34, with reference to the mRNA sequence registered under accession number NM_033625.2 in GenBank, a sequence starting at a nucleotide located about 2 kbp upstream of the transcription start site and ending at the nucleotide immediately upstream of the nucleotide sequence corresponding to the start codon sequence of RPL34 was used.

The promoter region of RPL34 was amplified by PCR using *E. coli* artificial chromosome clone RP11-462C24 (GenoTechs) as a template, and also using the following primer set and KOD-Plus-(TOYOBO), and then purified using a MinElute Reaction Kit (Qiagen). After CMV/pSeapIRESpuro was digested with SpeI and NheI and the CMV promoter was removed, the promoter region of RPL34 was integrated at the SpeI-NheI site using an In-Fusion Advantage PCR Cloning Kit (Clontech), whereby RPL34/pSeapIRESpuro was constructed. The nucleotide sequence of the cloned promoter region of RPL34 is represented by SEQ ID NO: 3 in the Sequence Listing.

```
Primer Set for RPL34:
RPL34-F:
                                        (SEQ ID NO: 23)
TTGATTATTGACTAGTATGGTGGCACAATCATGGTTCACTGCAGCC RPL34-R:
                                        (SEQ ID NO: 24)
GCAGCAGCATGCTAGCTCTGAGTGCCTAAATTAAGAATAGAGTAACATC
```

2-4) Cloning of Promoter Regions of Other Human Genes

Cloning of each of the promoter regions of EEF2, YBX1, PPIA, PSAP, RAN, RPLP1, RPS24, TMSB4X, UBC, YWHA, ARPC2, and SERBP1 was performed according to the method described in the above 2-1), whereby pSeapIRE-Spuro containing the cloned polynucleotide was constructed.

Example 3

Evaluation of Promoter Activity Using Expression Level of SEAP in Transfected CHO-K1 Polyclonal Cells as Index 3-1) Transfection CHO-K1 cells (ATCC) were subcultured in 5% $CO_2$ at 37° C. using F-12 nutrient mixture medium (GIBCO) containing 10% Ultra-Low IgG FBS (GIBCO).

The CHO-K1 cells were seeded onto a 6-well plate (IWAKI) at $5 \times 10^5$ cells/well. On the subsequent day, 2 µg of each of CMV/pSeapIRESpuro, RPS7/pSeapIRESpuro, RPL32/pSeapIRESpuro, RPL34/pSeapIRESpuro, or the like constructed in Examples 1) and 2) was transfected using Lipofectamine 2000 (Invitrogen).

3-2) Antibiotic Selection with Puromycin

Two days after transfection, the cells were collected from the 6-well plate by a trypsin treatment, the total amount of the collected cells was seeded into a 6-cm dish (Nunc), and also puromycin (Clontech) was added to the medium at a final concentration of 8 µg/ml to start antibiotic selection.

3-3) Evaluation Using Transfected Polyclonal Cell Line

After 11 days from the start of antibiotic selection, the transfected polyclonal cell line was collected with trypsin, and the number of cells was counted. Then, the cells were seeded onto a 24-well plate (IWAKI) at $1 \times 10^5$ cells/mL/well. After 24 hours, the culture supernatant was collected, and the activity of SEAP in the culture supernatant was measured using SensoLyte™ pNPP Secreted Alkaline Phosphatase Reporter Assay (ANASPEC). The activity of SEAP was higher under the control of each of the promoter regions of RPS7, RPL32, and RPL34 than under the control of the CMV promoter (CMV/pSeapIRESpuro) serving as the control, and the activity of SEAP was 1.7 times or more, 2.0 times or more, and 2.5 times or more higher than that of the control, respectively (FIG. 1). Meanwhile, the activity of SEAP was lower under the control of each of the promoter regions of EEF2, YBX1, PPIA, PSAP, RAN, RPLP1, RPS24, TMSB4X, UBC, YWHA, ARPC2, and SERBP1 than under the control of the CMV promoter.

Example 4

Cloning of Truncated Promoter

By using as the truncated promoters of RPS7, RPL32, and RPL34, a nucleotide sequence (T1) starting at a nucleotide located about 1 kb upstream of the transcription start site and ending at the nucleotide immediately upstream of the nucleotide sequence corresponding to the start codon of each gene, and a nucleotide sequence (T2) starting at a nucleotide located about 0.5 kb upstream of the transcription start site and ending at the nucleotide immediately upstream of the nucleotide sequence corresponding to the start codon of each gene, cloning of the truncated promoters was performed.

4-1) Cloning of RPS7T1 and RPS7T2

RPS7T1 and RPS7T2 were amplified by PCR using RPS7/pSeapIRESpuro constructed in 2-1) as a template, and also using the following primer set and KOD-Plus- (TOYOBO), and then purified using a MinElute Reaction Kit (Qiagen). After CMV/pSeapIRESpuro was digested with SpeI and NheI and the CMV promoter was removed, each of the promoter regions of RPS7T1 and RPS7T2 was integrated at the SpeI-NheI site using an In-Fusion Advantage PCR Cloning Kit (Clontech), whereby RPS7T1/pSeapIRE-Spuro and RPS7T2/pSeapIRESpuro were constructed. The nucleotide sequences of the cloned promoter regions of RPS7T1 and RPS7T2 are represented by SEQ ID NOS: 4 and 5 in the Sequence Listing, respectively.

```
Primer set for RPS7T1
RPS7-T1:
                                          (SEQ ID NO: 25)
TTGATTATTGACTAGTCCTAGTGTGGCTTCTGCATTTTTC

ACAGTGC

RPS7-R:
                                          (SEQ ID NO: 20)
GCAGCAGCATGCTAGCGGCTTTCTCCTGGGAGAACTGAAG

GCACAGCGG

Primer set for RPS7T2
RPS7-T2:
                                          (SEQ ID NO: 26)
TTGATTATTGACTAGTCCTCGGCTCACGGCAGCCTCGACCT

TTCGGC

RPS7-R:
                                          (SEQ ID NO: 20)
GCAGCAGCATGCTAGCGGCTTTCTCCTGGGAGAACTGAAG

GCACAGCGG
```

4-2) Cloning of RPL32T1 and RPL32T2

RPL32T1 and RPL32T2 were amplified by PCR using RPL32/pSeapIRESpuro constructed in 2-2) as a template, and also using the following primer set and KOD-Plus- (TOYOBO), and then purified using a MinElute Reaction Kit (Qiagen). After CMV/pSeapIRESpuro was digested with SpeI and NheI and the CMV promoter was removed, each of the promoter regions of RPL32T1 and RPL32T2 was integrated at the SpeI-NheI site using an In-Fusion Advantage PCR Cloning Kit (Clontech), whereby RPL32T1/pSeapIRE-Spuro and RPL32T2/pSeapIRESpuro were constructed. The nucleotide sequences of the cloned promoter regions of RPL32T1 and RPL32T2 are represented by SEQ ID NOS: 6 and 7 in the Sequence Listing, respectively.

```
Primer set for RPL32T1
RPL32T1:
                                          (SEQ ID NO: 27)
TTGATTATTGACTAGTCCTCTCGAGTAACTGGGACTACA

GGCATGC

RPL32-R:
                                          (SEQ ID NO: 22)
GCAGCAGCATGCTAGCGATGCCTTTTGGGGAAGAAGC

GGCCCC

Primer set for RPL32T2
RPL32T2:
                                          (SEQ ID NO: 28)
TTGATTATTGACTAGTGCAGTTTCGCCCAGTGGTTAGAA

GCGTGG

RPL32-R:
                                          (SEQ ID NO: 22)
GCAGCAGCATGCTAGCGATGCCTTTTGGGGAAGAAGCG

GCCCC
```

4-3) Cloning of RPL34T1 and RPL34T2

RPL34T1 and RPL34T2 were amplified by PCR using RPL34/pSeapIRESpuro constructed in 2-3) as a template, and also using the following primer set and KOD-Plus- (TOYOBO), and then purified using a MinElute Reaction Kit (Qiagen). After CMV/pSeapIRESpuro was digested with SpeI and NheI and the CMV promoter was removed, each of the promoter regions of RPL34T1 and RPL34T2 was integrated at the SpeI-NheI site using an In-Fusion Advantage PCR Cloning Kit (Clontech), whereby RPL34T1/pSeapIRE-Spuro and RPL34T2/pSeapIRESpuro were constructed. The nucleotide sequences of the cloned promoter regions of RPL34T1 and RPL34T2 are represented by SEQ ID NOS: 8 and 9 in the Sequence Listing, respectively.

```
Primer set for RPL34T1
RPL34T1:
                                          (SEQ ID NO: 29)
TTGATTATTGACTAGTGCTTCCTGGAGGTGCATTCTAAGAGCGCTCCCC RPL34-R:
                                          (SEQ ID NO: 24)
GCAGCAGCATGCTAGCTCTGAGTGCCTAAATTAAGAATAGAGTAACATC Primer set for RPL34T2
RPL34T2:
                                          (SEQ ID NO: 30)
TTGATTATTGACTAGTGTAAAGCTTGTGCTCTGAATAAATGACAAGG RPL34-R:
                                          (SEQ ID NO: 24)
GCAGCAGCATGCTAGCTCTGAGTGCCTAAATTAAGAATAGAGTAACATC
```

Example 5

Evaluation of Activity of Truncated Promoter Using Expression Level of SEAP in Transfected CHO-K1 Polyclonal Cells as Index 5-1) Transfection CHO-K1 cells (ATCC) were subcultured in 5% $CO_2$ at 37° C. using F-12 nutrient mixture medium (GIBCO) containing 10% Ultra-Low IgG FBS (GIBCO).

The CHO-K1 cells were seeded onto a 6-well plate (IWAKI) at $2\times10^5$ cells/well. On the subsequent day, 2 μg of each of CMV/pSeapIRESpuro, RPS7/pSeapIRESpuro, RPS7T1/pSeapIRESpuro, RPS7T2/pSeapIRESpuro, RPL32/pSeapIRESpuro, RPL32T1/pSeapIRESpuro, RPL32T2/pSeapIRESpuro, RPL34/pSeapIRESpuro, RPL34T1/pSeapIRESpuro, and RPL34T2/pSeapIRESpuro constructed in Examples 1), 2), and 4) was transfected using Fugene 6 (Roche Applied Science).

5-2) Antibiotic Selection with Puromycin

Two days after transfection, the cells were collected from the 6-well plate by a trypsin treatment, and the total amount of the collected cells was seeded into a 6-cm dish (Nunc), and also puromycin (Clontech) was added to the medium at a final concentration of 8 μg/ml to start antibiotic selection.

5-3) Evaluation Using Transfected Polyclonal Cell Line

After 11 days from the start of antibiotic selection, each transfected polyclonal cell line was collected with trypsin, and the number of cells was counted. Then, the cells were seeded onto a 24-well plate (IWAKI) at $1 \times 10^5$ cells/mL/well. After 24 hours, the culture supernatant was collected, and the activity of SEAP in the culture supernatant was measured using the SensoLyte (registered trademark) pNPP Secreted Alkaline Phosphatase Reporter Assay (ANASPEC). The measurement results are shown in FIG. 2. The activity of SEAP was higher under the control of each of the truncated promoters than under the control of the CMV promoter (CMV/pSeapIRESpuro) serving as the control, and thus, it was shown that these promoters have a higher promoter activity than the CMV promoter.

Example 6

Extraction of DNA Element 6-1) Chromatin Immunoprecipitation Using Anti-Acetylated Histone H3 Antibody ChIP using an anti-acetylated histone antibody was performed using EZ ChIP (Upstate) according to the following procedure. Incidentally, unless otherwise stated, Upstate's products were used as the antibodies, buffers, and the like in the following procedure.

First, 293F cells (Invitrogen) were cultured using GIBCO (registered trademark) FreeStyle™ 293 Medium (Invitrogen) under conditions of 37° C. and 8% $CO_2$, followed by centrifugation (1000 rpm, 5 min, room temperature), whereby cells in the growth phase were collected. After $2 \times 10^7$ cells were stirred in a medium containing 1% formaldehyde for 10 minutes, 10× glycine was added thereto, followed by stirring at room temperature for 5 minutes. After centrifugation (3000 rpm, 5 min, 4° C.), the supernatant was removed, and PBS was added to the cell pellet to suspend the cells. Then, the cell suspension was centrifuged again to remove PBS, and thereafter an SDS lysis buffer was added to the cell pellet to suspend and lyse the cells. Each sample obtained by cell lysis was subjected to DNA fragmentation using an ultrasonic homogenizer (BRANSON) while cooling the sample with ice water, and a dilution buffer containing a protease inhibitor cocktail and Protein G-immobilized agarose were added thereto. The resulting mixture was stirred at 4° C. for 1 hour, followed by centrifugation, and then the supernatant was collected. Subsequently, 10 μg of normal rabbit IgG or an α-acetyl histone H3 antibody was added thereto, followed by stirring overnight at 4° C. To the resulting solution, Protein G-immobilized agarose was added, and the resulting mixture was stirred at 4° C. for 1 hour, followed by centrifugation, and then the pellet was collected. The thus obtained pellet was washed twice with Low Salt Immune Complex Wash Buffer, twice with High Salt Immune Complex Wash Buffer, twice with LiCl Immune Complex Wash Buffer, and finally four times with TE Buffer. Then an elution buffer (containing 20 μl of 1 M sodium hydrogen carbonate, 10 μl of SDS, and 170 μl of sterile water) was added thereto. After 30 minutes, the mixture was centrifuged, and the supernatant was collected.

Subsequently, 5 M sodium chloride was added to the supernatant, and the resulting mixture was heated overnight at 65° C. Then RNase A was added thereto, and the resulting mixture was incubated at 37° C. for 30 minutes. Then 0.5 M EDTA, 1 M Tris-HCl, and Proteinase K were added thereto, and the resulting mixture was incubated at 45° C. for 2 hours.

Finally, Reagents A, B, and C were added thereto in an amount 5 times greater than that of the solution obtained by the treatment with Proteinase K, followed by centrifugation (10000 rpm, 30 sec, room temperature) using a spin filter, whereby chromatin-immunoprecipitated DNA was purified.

6-2) Microarray Analysis

By using a GenomePlex Complete Whole Genome Amplification (WGA) Kit (Sigma), each ChIP sample obtained in 6-1) was amplified. The procedure was in accordance with Sigma's protocol accompanying the Kit.

In order to confirm ChIP, by using 320 ng of each DNA amplified by WGA as a template, and also using the following primers and SYBR (registered trademark) Premix Ex Taq™ (Perfect Real Time) (TAKARA), a glycelaldehyde-3-phosphate dehydrogenase (GAPDH) gene was internally amplified by the PCR method (95° C. for 5 sec and 60° C. for 20 sec×45 cycles). Incidentally, GAPDH is a house keeping gene to be used as a positive control for confirming whether a DNA element is enriched by ChIP, and the PCR method was performed using primers attached to an EZ ChIP (Upstate).

(SEQ ID NO: 31)
5'-TACTAGCGGTTTTACGGGCG-3'

(SEQ ID NO: 32)
5'-TCGAACAGGAGGAGCAGAGAGCGA-3'

As a result, it was confirmed that GAPDH was amplified specifically in the sample subjected to immunoprecipitation with an anti-acetylated histone H3 antibody (FIG. 3). Each of the DNA samples amplified by WGA was subjected to microarray analysis (NimbleGen) to perform Chromatin Immunoprecipitation-on-chip (ChIP-on-chip). "ChIP-on-chip" is a technique for identifying each DNA element by subjecting DNA enriched in 6-1) to microarray analysis.

6-3) Extraction of DNA Element

Based on the results of the ChIP-on-chip analysis obtained in 6-2), 5 sequences having an AT content of 62% or more were extracted.

A2: chromosome 15 (80966429 to 80974878)
A7: chromosome 11 (88992123 to 89000542)
A18: chromosome 4 (111275976 to 111284450)
B5: chromosome 1 (143034684 to 143043084)
C14: chromosome 11 (46089056 to 46097482)

Example 7

Effect of DNA Element Using Expression of Secretory Alkaline Phosphatase (SEAP) as Index 7-1) Construction of SEAP Expression Vector By using pSEAP2-control (Clontech) as a template, the SEAP gene was amplified by the PCR method (94° C. for 30 sec and 68° C. for 2 min×40 cycles) using the following primers and KOD-Plus-(TOYOBO).

```
                                        (SEQ ID NO: 33)
5'-AAAGCTAGCATGCTGCTGCTGCTGCTGCTGGGCC-3'

(SEQ ID NO: 34)
5'-AAAAGATCTTCATGTCTGCTCGAAGCGGCCGGCCGC-3'
```

Subsequently, the amplified SEAP fragment was separated by agarose gel electrophoresis and cut out from the gel, followed by purification using a QIAquick Gel Extraction Kit (Qiagen). The thus obtained DNA fragment was used as an insert. The insert was digested with the restriction enzymes NheI and BglII, and a vector pIRES hyg3 (Clontech) was digested with the restriction enzymes NheI and BamHI. The resulting DNA fragments were subjected to agarose gel electrophoresis to separate the target fragments, respectively, and the target fragments were cut out from the gel, followed by purification. Then, a ligation reaction and transformation were performed. The ligation reaction was performed using the LigaFast Rapid DNA Ligation System (Promega). The transformation was performed as follows. First, frozen competent cells JM109 (TAKARA) were thawed, 10 µl of a solution obtained after the ligation reaction was added to a solution of the thawed cells, and the resulting mixture was left to stand on ice for 30 minutes. Thereafter, a heat shock (42° C., 45 sec) was applied to the mixture, and the mixture was cooled on ice for 5 minutes. To this cell suspension, 1 ml of LB medium was added, and the resulting mixture was shaken at 37° C. for 1 hour. Then, the mixture was plated on an LB plate containing 0.1 mg/ml ampicillin, and the plate was incubated at 37° C. for 14 to 16 hours. Thereafter, by alkaline lysis, a target plasmid was collected from colonies cultured on the LB plate. Finally, the polynucleotide sequence of SEAP in the plasmid obtained by alkaline lysis was determined, whereby pCMV/SEAP ires Hygro was constructed.

7-2) Cloning of DNA Element

Subsequently, each of the DNA elements extracted in Example 6 was cloned from a bacterial artificial chromosome (BAC) containing a polynucleotide sequence corresponding to the DNA element into the SEAP expression vector obtained in 7-1) using a BAC SUBCLONING Kit (Gene Bridges).

First, pCMV/SEAP ires Hygro obtained in 7-1) was digested with the restriction enzyme SpeI for several hours, followed by ethanol precipitation, and the precipitate was dissolved in sterile water. By using the vector digested with SpeI as a template, the PCR method (94° C. for 15 sec, 55° C. for 30 sec, and 68° C. for 10 min×30 cycles) was performed using the following primers and KOD-Plus-(TOYOBO).

```
A2D:
                                        (SEQ ID NO: 35)
5'-GGAAATTGAGAAGTATCATTCACAACAGTACCACAAACA

TGAAATAAATGTGGATCCTATTAATAGTAATCAATTACG-3'

A2R:
                                        (SEQ ID NO: 36)
5'-CTCATTCTGTGGGTTGTCATTTCACTTCCTTGATGCTATCC

TTTCAAGCAAAATCCTAGTCAATAATCAATGTCAACG-3'

A7D:
                                        (SEQ ID NO: 37)
5'-CTTATTTTCTAAGTAGTATAGACTTAATTGTGAGAACAA

AATAAAAACTTGGATCCTATTAATAGTAATCAATTACG-3'

A7R:
                                        (SEQ ID NO: 38)
5'-CTCTTCCCATTCTCATTTGAATCTACTTCAAAAGGTTTAC

CATACTAAGACCTAGTCAATAATCAATGTCAACG-3'

A18D:
                                        (SEQ ID NO: 39)
5'-CGCCTGTAATCCCAGCACTTTGGGAGGCTGAGGCGGGTG

GATCACCTGAGGTCGATCCTATTAATAGTAATCAATTACG-3'

A18R:
                                        (SEQ ID NO: 40)
5'-CATACAGAAGCCAGTTTGAACTGAGACCTCACTCCATTTC

TTACAAGTTATGCCCTAGTCAATAATCAATGTCAACG-3'

B5D:
                                        (SEQ ID NO: 41)
5'-ACCGTTTTATATTGTTTAAGCATTTCCTAGACATATTTGGC

TACAAATCTAGATCCTATTAATAGTAATCAATTACG-3'

B5R:
                                        (SEQ ID NO: 42)
5'-GATCTTAGGGGGGCTGATTATATAAAACAATAGAAATGT

AGTCTTAGATGAAACCTAGTCAATAATCAATGTCAACG-3'

C14D:
                                        (SEQ ID NO: 43)
5'-CACAAAGTTCACTGTCAAGGCCAGGTGATGAGGCCCACA

CATGCCCGGACCTTGATCCTATTAATAGTAATCAATTACG-3'

C14R:
                                        (SEQ ID NO: 44)
5'-CAAAACCTCATCTCTACTGAAAATAGAAAATTAGCTGGG

CGTGGTGGCAGGTGCCCTAGTCAATAATCAATGTCAACG-3'
```

After the amplification was confirmed by agarose gel electrophoresis using a portion of the reaction solution, the rest of the reaction solution was subjected to ethanol precipitation. The precipitate was dissolved in sterile water, and the resulting solution was used as DNA for transformation.

Subsequently, preparation of *Escherichia coli* for transformation was performed.

BAC clones corresponding to the 5 sequences extracted in Example 6 are as follows.

TABLE 1

| Extracted sequence | Corresponding BAC clone |
| --- | --- |
| A2 | RP11-152F13 |
| A7 | RP11-643G5 |
| A18 | RP11-115A14 |
| B5 | RP11-640M9 |
| C14 | RP11-702F3 |

10 µl of the above-mentioned BAC clone (Advanced GenoTechs Co.), which had been thawed, was inoculated into 1 ml of a medium (containing chloramphenicol at a final concentration of 15 µg/ml) and incubated overnight at 37° C. 30 µl of the culture solution was transferred to 1.4 ml of a medium (containing chloramphenicol at a final concentration of 15 µg/ml) and incubated at 37° C. for 2 hours.

Centrifugation and washing with sterile water were repeated twice, and the cells were suspended in 20 μl of sterile water. To a cooled cuvette (0.1 cm), 1 μl of pRED/ET (Gene Bridges) and *Escherichia coli* were added, followed by electroporation (1350 V, 10 μF). Then, 1 ml of SOC medium was added thereto, and the resulting mixture was incubated at 30° C. for 70 minutes. 100 μl of the culture solution was plated on an LB plate (containing tetracycline and chloramphenicol at final concentrations of 3 μg/ml and 15 μg/ml, respectively), and incubated overnight at 30° C. On the subsequent day, each colony thus obtained was inoculated into 1 ml of a medium (containing tetracycline and chloramphenicol at final concentrations of 3 μg/ml and 15 μg/ml, respectively), and incubated overnight at 30° C. 30 μl of the culture solution was transferred to 1.4 ml of a medium (containing tetracycline and chloramphenicol at final concentrations of 3 μg/ml and 15 μg/ml, respectively), and incubated at 30° C. for 2 hours. Then, 50 μl of 10% L-arabinose was added thereto, and incubation was further performed at 37° C. for 1 hour. Thereafter, washing with sterile water was repeated twice, and *Escherichia coli*, which was suspended in 30 μl of sterile water, and 1 μl of the DNA for transfection were added to a cooled cuvette (0.1 cm), followed by electroporation (1350 V, 10 g). Then, 1 ml of SOC medium was added thereto, and the resulting mixture was incubated at 37° C. for 90 minutes. The total amount of the culture solution was plated on an LB plate (containing 100 μg/ml ampicillin), and the plate was incubated. Thereafter, a target plasmid was obtained by alkaline lysis. Finally, the sequence of the obtained plasmid and the restriction enzyme sites thereof were confirmed, whereby a target plasmid was constructed (FIG. 4).

7-3) Evaluation Using SEAP Expression as Index

Each plasmid constructed in 7-2) was evaluated using the host cell CHO-K1 (ATCC) and the transfection reagent Lipofectamine 2000 (Invitrogen).

Antibiotic selection with hygromycin at 800 μg/ml was performed for about 2 weeks starting 2 days after transfection, whereby a stably expressing polyclonal cell line was established. The thus established cell line was subjected to medium replacement on the day before measurement, and a given number of the cells were seeded onto a 24-well plate (IWAKI). At 24 hours after plating the cells, the culture supernatant was collected, and the activity of SEAP was measured. The activity of SEAP in the culture supernatant was measured by SensoLyte™ pNPP Secreted Alkaline Phosphatase Reporter Assay (ANASPEC).

The measured results are shown in FIG. 5. When the activity of SEAP in the control with no element was normalized to 1, the activity of SEAP in the culture supernatant of the stably expressing CHO cell line having the DNA element A2, A7, A18, B5, or C14 showed a numerical value five times or more higher than that of the control. Based on the results, it was confirmed that all the 5 types of DNA elements dramatically enhance SEAP expression. Incidentally, the polynucleotide sequences of the above 5 types of DNA elements are represented by SEQ ID NOS: 10 to 14 in the Sequence Listing, respectively.

Example 8

Generality of Promoter to be Used in Combination

The promoter of the vector used in the evaluation of the DNA elements in Example 7 was a CMV promoter, and thus the use of DNA elements in combination with other general promoters was studied.

8-1) Construction of SEAP Expression Vector Using EF-1α and SV40 Promoters

By using pSEAP2-control (Clontech) as a template, the SEAP gene was amplified by the PCR method (94° C. for 30 sec and 68° C. for 2 min×40 cycles) using the primers described in 7-1) and KOD-Plus-. The amplified SEAP gene was prepared as an insert in the same manner as in 7-1). The insert was digested with the restriction enzymes NheI and BglII, and a pIRES puro3 vector (Clontech) was digested with the restriction enzymes NheI and BamHI, and pCMV/SEAP ires Puro was constructed in the same manner as in 7-1).

Subsequently, by using pEF1/V5-His A (Invitrogen) as a template, an EF-1α promoter was amplified by the PCR method (94° C. for 15 sec, 60° C. for 30 sec, and 68° C. for 2 min×30 cycles) using the following primers and KOD-Plus-.

```
                                        (SEQ ID NO: 45)
5'-AAAACTAGTCAGAGAGGAATCTTTGCAGCTAATGGACC-3'

(SEQ ID NO: 46)
5'-AAAGATATCCCTAGCCAGCTTGGGTGGTACCAAGC-3'
```

By using the above-constructed pCMV/SEAP ires Puro as a vector, digestion with the restriction enzymes SpeI and EcoRV was performed for the vector and the promoter, and pEF/SEAP ires Puro was constructed according to the method described in 7-1).

Similarly, by using pcDNA3.1+(Invitrogen) as a template, an SV40 promoter was amplified by the PCR method (94° C. for 15 sec, 60° C. for 30 sec, and 68° C. for 1 min×30 cycles) using the following primers and KOD-Plus-.

```
                                        (SEQ ID NO: 47)
5'-AAAACTAGTCTGTGGAATGTGTGTCAGTTAGGGTG-3'

(SEQ ID NO: 48)
5'-AAAGATATCAGCTTTTTGCAAAAGCCTAGGCCTC-3'
```

By using the above-constructed pCMV/SEAP ires Puro as a vector, digestion with the restriction enzymes SpeI and EcoRV was performed for the vector and the promoter, and pSV40/SEAP ires Puro was constructed according to the method described in 7-1).

8-2) Cloning of DNA Element A2 or A7

Subsequently, cloning of the DNA element A2 or A7 was performed using the pEF/SEAP ires Puro and pSV40/SEAP ires Puro constructed in 8-1) as basic structures.

First, pEF/SEAP ires Puro and pSV40/SEAP ires Puro were digested with the restriction enzyme SpeI for several hours, followed by ethanol precipitation, and the precipitate was dissolved in sterile water. By using the respective vectors digested with SpeI as templates, DNA for transfection was prepared by the PCR method (94° C. for 15 sec, 55° C. for 30 sec, and 68° C. for 10 min×30 cycles) using the following primers and KOD-Plus-.

```
A2 (EF/D):
                                        (SEQ ID NO: 49)
5'-GGAAATTGAGAAGTATCATTCACAACAGTACCACAA

ACATGAAATAAATGTGCTAGTCAGAGAGGAATCTTTGCAGC-3'
```

-continued

A2 (SV40/D):
(SEQ ID NO: 50)
5'-GGAAATTGAGAAGTATCATTCACAACAGTACCACA

AACATGAAATAAATGTGCTAGTCTGTGGAATGTGTGTCAGTTAG-3'

A2 (EF and SV40/R):
(SEQ ID NO: 51)
5'-CTCATTCTGTGGGTTGTCATTTCACTTCCTTG

ATGCTATCCTTTCAAGCAAAATTTTAAAACTTTATCCATCTTTGCA-3'

A7 (EF/D):
(SEQ ID NO: 52)
5'-CTTATTTTCTAAGTAGTATAGACTTAATTGTGAGAAC

AAAATAAAAACTTGCTAGTCAGAGAGGAATCTTTGCAGC-3'

A7 (SV40/D):
(SEQ ID NO: 53)
5'-CTTATTTTCTAAGTAGTATAGACTTAATTGTGAGA

ACAAAATAAAAACTTGCTAGTCTGTGGAATGTGTGTCAGTTAG-3'

A7 (EF and SV40/R):
(SEQ ID NO: 54)
5'-CTCTTCCCATTCTCATTTGAATCTACTTCAAA

AGGTTTACCATACTAAGAACTAGTTTTAAAACTTTATCCATCTTTGCA-3'

By using the thus prepared DNA for transfection and a BAC transfected with pRed/ET, the DNA element A2 or A7 was cloned into the vector described in 8-1). Incidentally, the procedure was performed according to the method described in 7-2).

8-3) Evaluation Using SEAP Expression as Index

Each plasmid constructed in 8-2) was evaluated using the host cell CHO-K1 (ATCC) and the transfection reagent Lipofectamine 2000 (Invitrogen).

Antibiotic selection with puromycin at 8 μg/ml was performed for about 2 weeks starting 2 days after transfection, whereby a stably expressing polyclonal cell line was established. The thus established cell line was subjected to medium replacement on the day before measurement, and a given number of the cells were seeded onto a 24-well plate. At 24 hours after plating the cells, the culture supernatant was collected, and the activity of SEAP was measured. The activity of SEAP in the culture supernatant was measured using SensoLyte™ pNPP Secreted Alkaline Phosphatase Reporter Assay (ANASPEC).

The measurement results are shown in FIG. 6. When the activity of SEAP in the control with no element was normalized to 1, the DNA element A2 or A7 exhibited an expression-enhancing effect such that the activity of SEAP was two times or more higher in the case of use with the EF-1α promoter, and four times or more higher in the case of use with the SV40 promoter than that of the control. Based on these results, it was confirmed that these DNA elements exhibit the effect of enhancing foreign gene expression when used in combination with a general promoter.

Example 9

Evaluation Using Antibody Expression as Index 9-1) Construction of Human Light Chain Expression Vector pEF6KCL By using the plasmid pEF6/V5-HisB (Invitrogen) as a template, a DNA fragment between position 2174 (immediately downstream of BGHpA) and position 2958 (SmaI) (a DNA fragment containing an f1 origin of replication and an SV40 promoter and origin of replication, hereinafter referred to as "fragment A", the polynucleotide sequence of fragment A being represented by SEQ ID NO: 15 in the Sequence Listing) was obtained by the PCR method using the following primers and KOD-Plus-.

(SEQ ID NO: 55)
5'-CCACGCGCCCTGTAGCGGCGCATTAAGC-3'

(SEQ ID NO: 56)
5'-AAACCCGGGAGCTTTTTGCAAAAGCCTAGG-3'

The obtained fragment A and a DNA fragment containing a DNA sequence encoding a human κ chain secretory signal, a human κ chain constant region, and a human poly(A) addition signal (hereinafter referred to as "fragment B") were ligated by overlapping PCR. The thus obtained DNA fragment in which fragment A and fragment B were ligated was digested with the restriction enzymes KpnI and SmaI, and the resulting fragment was ligated to plasmid pEF6/V5-HisB (Invitrogen) which was digested with the restriction enzymes KpnI and SmaI, whereby a human light chain expression vector pEF6KCL having a signal sequence, a cloning site, a human κ chain constant region, and a human poly(A) addition signal sequence downstream of the EF-1α promoter was constructed.

A DNA fragment obtained by digesting the pEF6KCL prepared by the above-mentioned method with the restriction enzymes KpnI and SmaI was ligated to pEF1/myc-HisB (Invitrogen) which was digested with KpnI and SmaI, followed by transformation, alkaline lysis, and sequencing, whereby a plasmid pEF1KCL was constructed.

9-2) Construction of Human Heavy Chain Expression Vector pEF1FCCU

A DNA fragment (the polynucleotide sequence of this DNA fragment is represented by SEQ ID NO: 16 in the Sequence Listing) containing a DNA sequence encoding a human IgG1 signal sequence and a constant region amino acid sequence was digested with the restriction enzymes NheI and PmeI, and the resulting fragment was ligated to a plasmid pEF1 KCL which was digested with NheI and PmeI, whereby a human heavy chain expression vector pEF1FCCU having a signal sequence, a cloning site, a human heavy chain constant region, and a human poly(A) addition signal sequence downstream of the EF-1α promoter was constructed.

9-3) Construction of Single Humanized Antibody Gene X Expression Vector (Humanized Antibody Gene X/pEF_LHN#)

By ligating the L-chain or H-chain expression vector constructed in 9-1) or 9-2), a single antibody expression vector (pEF_LHN (lacking a variable region)) was constructed.

A restriction enzyme SalI site was added by the PCR method to both ends of the gene expression unit: one upstream of the promoter and the other downstream of the poly(A) of pEF1KCL. Agarose gel electrophoresis, cutting out of a desired DNA fragment from the gel, and purification of the DNA fragment were then performed, whereby an insert was prepared. By digesting the vector pEF1FCCU constructed in 9-2) with the restriction enzyme SalI, the vector was linearized at the SalI site located upstream of the gene expression unit. Then, the linearized vector was ligated to the above insert, followed by transformation, alkaline lysis, and sequencing, whereby a single humanized antibody expression vector (pEF_LHN (lacking a variable region)) was constructed.

Subsequently, the following oligonucleotides were introduced into an AatII site of the vector pEF_LHN (lacking a variable region).

```
                                         (SEQ ID NO: 57)
5'-CGCGGCCGCACTAGTGACGT-3'

(SEQ ID NO: 58)
5'-CACTAGTGCGGCCGCGACGT-3'
```

The respective oligonucleotides were diluted to 5 pmol, and by using T4 Polynucleotide Kinase (TAKARA), a reaction was allowed to proceed at 37° C. for 1 hour. Then, 10×H buffer (TAKARA) was added thereto, and annealing was performed by a reaction at 96° C. for 1 minute and then at room temperature for 30 minutes. These oligonucleotides and the vector pEF_LHN which was digested with the restriction enzyme AatII were ligated, followed by transformation, alkaline lysis, and sequencing, whereby pEF_LHN# (lacking a variable region) was constructed.

By integrating a variable region of the humanized antibody gene X into the above-constructed universal vector (pEF_LHN# (lacking a variable region)), the construction of a single humanized antibody gene X expression vector (humanized antibody gene X/pEF_LHN#) was completed.

First, by using the following primers and KOD-Plus-, an L-chain variable region of the humanized antibody gene X was amplified by the PCR method (94° C. for 15 sec, 55° C. for 30 sec, and 68° C. for 1 min×30 cycles).

```
L-chain variable region:
                                         (SEQ ID NO: 59)
5'-AAACATATGGCGACATCCAGATGAC-3'

(SEQ ID NO: 60)
5'-AAACGTACGCTTGATCTCCACCTTGG-3'
```

The amplified L-chain variable region fragment and the universal vector (pEF_LHN# (lacking a variable region)) were digested with the restriction enzymes NdeI and BsiWI, followed by agarose gel electrophoresis, cutting out of a desired fragment from the gel, purification, ligation reaction, transformation, alkaline lysis, and sequencing, whereby the L-chain variable region was integrated into the vector. In the same manner, by using the following primers and KOD-Plus-, an H-chain variable region of the humanized antibody gene X was amplified by the PCR method (94° C. for 15 sec, 55° C. for 30 sec, and 68° C. for 1 min×30 cycles).

```
H-chain variable region:
                                         (SEQ ID NO: 61)
5'-AAAGCTGAGCCAGGTGCAGCTGCAGG-3'

(SEQ ID NO: 62)
5'-AAAGCTGAGCTCACGGTCACCAGGGTTC-3'
```

The amplified H-chain variable region fragment and the vector having the L-chain variable region inserted therein were digested with the restriction enzyme BlpI, followed by agarose gel electrophoresis, cutting out of a desired fragment from the gel, purification, ligation reaction, transformation, alkaline lysis, and sequencing, whereby the H-chain variable region was integrated into the vector and a single humanized antibody gene X expression vector (humanized antibody gene X/pEF_LHN#) was constructed.

9-4) Construction of Single Humanized Antibody Gene X Expression Vector (Humanized Antibody Gene X/pCMV_LHN#)

By using the single humanized antibody gene X expression vector (humanized antibody gene X/pEF_LHN#) constructed in 9-3) as a basic vector structure, another single humanized antibody gene X expression vector (humanized antibody gene X/pCMV_LHN#) was constructed by replacing the promoter according to the following procedure.

By using pIRES puro3 as a template, a CMV promoter fragment was amplified by the PCR method (94° C. for 30 sec and 68° C. for 3 min×40 cycles) using the following primers and KOD-Plus-.

```
Upstream of H-chain:
                                         (SEQ ID NO: 63)
5'-CTTTTGCAAAAAGCTTCGCGTTACATAACTTACGGTAAATGGCC-3'

(SEQ ID NO: 64)
5'-TTCATGGTGGCGCTAGCCCGCAGATATCGATCCGAGCTCGGTA-3'

Upstream of L-chain:
                                         (SEQ ID NO: 65):
5'-TGACGTCGACAAGCTTCGCGTTACATAACTTACGGTAAATGGCC-3'

(SEQ ID NO: 66)
5'-CTGGATGTCGCCATATGCGCCGGAGATCCACAGCAGCAGGGAGA

TGAACACCTGGGTCTGCAGCACCATGGTGGCGCTAGCCCGCAGATATCGA

TCCGAGCTCGGTA-3'
```

To the PCR reaction solution, the restriction enzyme DpnI was added, and a reaction was allowed to proceed at 37° C. for 1 hour, followed by purification using a MinElute reaction Cleanup kit (Qiagen), whereby a sample for use in In-Fusion was prepared. Meanwhile, the humanized antibody gene X/pEF_LHN# was digested with the restriction enzymes HindIII, NheI, NdeI, and FseI, followed by agarose gel electrophoresis, whereby two large fragments among the resulting fragments were separated. Each of the fragments was cut out from the gel, and the DNA was extracted from the gel, whereby a sample for use in In-Fusion was prepared. All the samples for use in In-Fusion were put together, and cloning was performed using an In-Fusion™ Advantage PCR Cloning Kit (TAKARA), followed by transformation, alkaline lysis, and sequencing, whereby a single humanized antibody gene X expression vector (humanized antibody gene X/pCMV_LHN#) was constructed.

9-5) Cloning of DNA Element A7

A7 was selected from the 5 types of DNA element which had been confirmed to have the effect of enhancing SEAP expression, and cloned into an antibody expression vector.

In the same manner as in 7-2), by using each of the single humanized antibody gene X expression vectors (humanized antibody gene X/pEF_LHN# and humanized antibody gene X/pCMV_LHN#) digested with the restriction enzyme NotI as a template, DNA for transfection was prepared by the PCR method (94° C. for 15 sec, 55° C. for 30 sec, and 68° C. for 11 min×30 cycles) using the following primers and KOD-Plus-.

Humanized antibody gene X/pEF_LHN# D:

(SEQ ID NO: 67)
5'-CTCTTCCCATTCTCATTTGAATCTACTTCAAAAGGTTTACCATACTA

AGACTCGAGGCACTAGTGACGTCAGGTGGCACT-3'

Humanized antibody gene X/pEF_LHN# R:

(SEQ ID NO: 68)
5'-CTCTTCCCATTCTCATTTGAATCTACTTCAAAAGGTTTACCATACTA

AGAGCACTAGTGACGTCAGGTGGCACTTTTCGG-3'

Humanized antibody gene X/pCMV_LHN# D: Humanized antibody gene X/pEF_LHN# D was used.

Humanized antibody gene X/pCMV_LHN# R: Humanized antibody gene X/pEF_LHN# R was used.

By using the above-prepared DNA for transfection and a BAC transfected with pRed/ET, the DNA element A7 was cloned into the single humanized antibody gene X expression vectors described in 9-3) and 9-4). A schematic view of the vector construct is shown in FIG. 7. Incidentally, the procedure was performed according to the method described in 7-2).

9-6) Evaluation Using Antibody Expression as Index

Each plasmid constructed in 9-5) was evaluated using the host cell CHO-K1 (ATCC) and the transfection reagent Lipofectamine 2000 (Invitrogen).

Antibiotic selection with Geneticin (Roche) at 800 µg/ml was performed for about 2 weeks starting 2 days after transfection, whereby a stably expressing polyclonal cell line was established. The thus established cell line was subjected to medium replacement on the day before measurement, and a given number of the cells were seeded onto a 24-well plate. At 24 hours after plating the cells, the culture supernatant was collected, and the expression level of the antibody in the culture supernatant was measured by the ELISA method. Incidentally, the ELISA was performed as follows. In a 96-well plate coated with anti-kappa light chain at 50 ng/well, 100 µl of the cell-free culture supernatant was added to each well, and the plate was incubated at 37° C. for 1 hour. Subsequently, the sample (culture supernatant) was removed, and each well was washed with 200 µl of PBS-Tween (0.05%). Then, 100 µl of HRP-labeled anti-human IgG (Fc) was added to each well and the plate was incubated at 37° C. for an additional 1 hour. Thereafter, the HRP-labeled anti-human IgG (Fc) was removed, and each well was washed with PBS-Tween (0.05%). Then, a color was developed using a POD Substrate ABTS Kit (Nacalai), and the absorbance at a measurement wavelength of 405 nm was measured. For the dilution of the anti-kappa light chain, the anti-human IgG (Fc), and the sample, PBS-Tween (0.05%) was used. By using human IgG serially diluted to 12 ng, 6 ng, 3 ng, 1.5 ng, 0.75 ng, 0.375 ng, and 0.1875 ng as a standard, the concentration of the sample was calculated.

The results are shown in FIG. 8. It was confirmed that the sample having the DNA element A7 has a greater effect of enhancing antibody production as compared with a control with no element when the EF-1α promoter or the CMV promoter was used in the antibody expression vector.

Example 10

Length of Sequence Exhibiting Activity of Enhancing Foreign Gene Expression 10-1) Cloning of DNA Elements Having Different Sequence Lengths Based on the length of the sequence used in Example 7, vectors containing each of the DNA elements but having different sequence lengths were constructed.

The details of the DNA elements having different sequence lengths which were designed based on the full length of each of the DNA elements A2, A7, A18, B5, and C14 are shown in FIGS. 9, 11, 13, 15, and 17, respectively. The pCMV/SEAP ires Hygro described in 7-1) was digested with the restriction enzyme SpeI for several hours, followed by ethanol precipitation, and the precipitate was dissolved in sterile water. By using the vector digested with SpeI as a template, DNA for transfection was prepared by the PCR method (94° C. for 15 sec, 55° C. for 30 sec, and 68° C. for 10 min×30 cycles) using the following primers and KOD-Plus-. By using the thus prepared DNA for transfection and the corresponding BAC transfected with pRed/ET, each DNA element having a different sequence length was cloned into the pCMV/SEAP ires Hygro described in 7-1). Incidentally, the procedure was performed according to the method described in 7-2).

A2-1D:

(SEQ ID NO: 69)
5'-CATGCACAGATTAGCCATTTAGTACTTACTAAATCAAAC

TCAATTTCTGAAGTCTAGTTATTAATAGTAATCAATTACG-3'

A2-1R:

(SEQ ID NO: 70)
5'-CTCATTCTGTGGGTTGTCATTTCACTTCCTTGATGCTATCC

TTTCAAGCAAAATTCAATAATCAATGTCAACGCGTATAT-3'

A2-2D:

(SEQ ID NO: 71)
5'-ACACTGGTCAAAGGGACAGGTCATTGTTATGCTGGCAAT

GCAGGCTGCTGAAAACTAGTTATTAATAGTAATCAATTACG-3'

A2-2R:

(SEQ ID NO: 72)
5'-ACTGTAGCTTCTTATTTTTTACCTGCAGTGCATTCCTGTA

AAAGTAGTGTGGAGTCAATAATCAATGTCAACGCGTATAT-3'

A2-3D:

(SEQ ID NO: 73)
5'-CTGGAAATTGAGAAGTATCATTCACAACAGTACCACAAA

CATGAAATAAATGTGCTAGTTATTAATAGTAATCAATTACG-3'

A2-3R:

(SEQ ID NO: 74)
5'-CCAAGCTTGTCCAACCGCGGCCTGCAGGCTGCATGCAGC

CTGTGAAGGCTTTGATCAATAATCAATGTCAACGCGTATAT-3'

A2-4D:

(SEQ ID NO: 75)
5'-TCAATCATTTATCAATTTTATCTTCAAAGTCCCTCACTTC

AGGGAGATGATATACTAGTTATTAATAGTAATCAATTACG-3'

-continued

A2-4R:
(SEQ ID NO: 76)
5'-ATATATAAAAGTTCATGTATATATAAAATCATGCAATA

CACGGCCTTTTGTGACTCAATAATCAATGTCAACGCGTATAT

A2-5D:
(SEQ ID NO: 77)
5'-CGCATAAAAGGAAAAGCATCCTTAAAATAAACACCATC

AATGGCTCCTCGGTGGCTAGTTATTAATAGTAATCAATTACG-3'

A2-5R: A2-5R was used.

A2-6D:
(SEQ ID NO: 78)
5'-GGGAGGCTACAGCTTGCCTCTCTAACCACTAAAAGGCA

TGACCCTCCTCAAAGCTAGTTATTAATAGTAATCAATTACG-3'

A2-6R: A2-6R was used.

A2-7D:
(SEQ ID NO: 79)
5'-TCTGGCTTCCCTGGGCCACGCTGGAAGAAGAATTGTC

TTGCGCCACACATAAAACTAGTTATTAATAGTAATCAATTACG-3'

A2-7R:
(SEQ ID NO: 80)
5'-AGCTGATTTTTACGTTAAATGTAACATGTAAAGAAATAT

ATGTGTGTTTTTAGATCAATAATCAATGTCAACGCGTATAT-3'

A2-8D:
(SEQ ID NO: 81)
5'-GTGAAGAGGAGGAGATGTCAAAATTCAAAGTCTTAAAT

GATGTAGTTTTAAGTACTAGTTATTAATAGTAATCAATTACG-3'

A2-8R:
(SEQ ID NO: 82)
5'-ATGACACTTGATATTGTTGTTTATATTGCTGGTTAGTATG

TGCCTTCATTTACCTCAATAATCAATGTCAACGCGTATAT-3'

A2-9D: A2-6D was used.
A2-9R: A2R was used.
A2-10D: A2-2D was used.
A2-10R A2-7R was used.
A2-11D: A2-8D was used.
A2-11R: A2-2R was used.
A2-12D: A2-2D was used.
A2-12R: A2-4R was used.
A2-13D: A2-8D was used.
A2-13R: A2-7R was used.
A2-14D: A2D was used.
A2-14R: A2-2R was used.
A2-15D: A2-2D was used.
A2-15R: A2R was used.
A2-16D: A2-8D was used.
A2-16R: A2-4R was used.
A2-17D: A2D was used.
A2-17R: A2-7R was used.

A7-1D:
(SEQ ID NO: 83)
5'-AAAAACAAAACTGGAGTAAACAAGATGAATTGTTTTAA

TAGAGGCACTGTATTACTAGTTATTAATAGTAATCAATTACG-3'

A7-1R:
(SEQ ID NO: 84)
5'-ATACAATGTTCCATGTATTCTGTGCCTGAACCTATGCAGC

TGATGTAGCTGAAGTCAATAATCAATGTCAACGCGTATAT-3'

A7-2D:
(SEQ ID NO: 85)
5'-GATCTTATTTTCTAAGTAGTATAGACTTAATTGTGAGAAC

AAAATAAAAACTTGCTAGTTATTAATAGTAATCAATTACG-3'

A7-2R:
(SEQ ID NO: 86)
5'-TGTTGTTTTCAGCCACTAAGTTTGAGGTGATTTGTTCTGG

CAGTCCTAGGAAACTCAATAATCAATGTCAACGCGTATAT-3'

A7-3D: A7-2D was used.

A7-3R:
(SEQ ID NO: 87)
5'-AGCCTACACTACCCTTTGCAGCCTTTGGTAACTATCCTT

CTGCTGTCTACCTCCTCAATAATCAATGTCAACGCGTATAT-3'

A7-4D:
(SEQ ID NO: 88)
5'-AGGAGCTCCTGAATGAAGGACATCACTCAGCTGTGTTAA

GTATCTGGAACAATACTAGTTATTAATAGTAATCAATTACG-3'

A7-4R:
(SEQ ID NO: 89)
5'-GACATAAAATGTAAGATATGATATGCTATGTAAGATATG

ATACCTGCCTTAAAATCAATAATCAATGTCAACGCGTATAT-3'

A7-5D:
(SEQ ID NO: 90)
5'-CACTGCTTGATACTTACTGTGGACTTTGAAAATTATGAAT

GTGTGTGTGTGTCTAGTTATTAATAGTAATCAATTACG-3'

A7-5R:
(SEQ ID NO: 91)
5'-CAATTACATTCCAGTGATCTGCTACTTAGAATGCATGACT

GAACTCCTGGGTGGTCAATAATCAATGTCAACGCGTATAT-3'

A7-6D:
(SEQ ID NO: 92)
5'-TTATTTTGAAGAGAAACTCCTGGTTCCCACTTAAAATCCT

TTCTTGTTTCCAAGCTAGTTATTAATAGTAATCAATTACG-3'

A7-6R:
(SEQ ID NO: 93)
5'-AAGCAGTGTGTGTTTACCTGCATGTGTATGTGAATTAAC

TCTGTTCCTGAGGCATCAATAATCAATGTCAACGCGTATAT-3'

A7-7D:
(SEQ ID NO: 94)
5'-ATTGCATGTTCTCATTTATTTGTGGGATGTAAAAATCAAA

ACAATAGAACGTATCTAGTTATTAATAGTAATCAATTACG-3'

-continued

A7-7R:
(SEQ ID NO: 95)
5'-TTGGGAGGCCGCAGCTGGTAGATCACTTGAGGCCACGAA

TTTGACACCAGCAGGTCAATAATCAATGTCAACGCGTATAT-3'

A7-8D: A7-1D was used.

A7-8R: A7R was used.

A7-9D: A7-7D was used.

A7-9R: A7-5R was used.

A7-10D: A7-4D was used.

A7-10R: A7-7R was used.

A7-11D: A7-6D was used.

A7-11R: A7-4R was used.

A7-12D: A7-2D was used.

A7-12R: A7-6R was used.

A7-13D: A7-7D was used.

A7-13R: A7R was used.

A7-14D: A7-4D was used.

A7-14R: A7-5R was used.

A7-15D: A7-6D was used.

A7-15R: A7-7R was used.

A7-16D: A7-2D was used.

A7-16R: A7-4R was used.

A7-17D: A7-4D was used.

A7-17R: A7R was used.

A7-18D: A7-6D was used.

A7-18R: A7-5R was used.

A18-1:
(SEQ ID NO: 96)
5'-ATCCCCTGCTCTGCTAAAAAAGAATGGATGTTGACTCTC

AGGCCCTAGTTCTTGATCCTATTAATAGTAATCAATTACG-3'

A18-1R: A18R was used.

A18-2D:
(SEQ ID NO: 97)
5'-CTAAAGTGCTGGGATTACAGGCATAAGCCACCGTGCCC

GGCTGGAGCATTGGGATCCTATTAATAGTAATCAATTACG-3'

A18-2R:
(SEQ ID NO: 98)
5'-ACTACTTACACATTTCGAGTTTTAAATAAGGCGTTCAA

TATAGAGTGAACACCTAGTCAATAATCAATGTCAACG-3'

A18-3D:
(SEQ ID NO: 99)
5'-CAGGCATAAGCCACCGCACCCGGCCACCCCTTACTAAT

TTTTAGTAACGTCGATCCTATTAATAGTAATCAATTACG-3'

A18-3R:
(SEQ ID NO: 100)
5'-CTGATTGACTTTGACCTCTGCTTTCCAACTTTGCCCCAA

AGAAAGTTAGTCACCTAGTCAATAATCAATGTCAACG-3'

A18-4D: A18-3D was used.

A18-4R:
(SEQ ID NO: 101)
5'-TTCAATGAAACAAGCTCTGTGAGGCTCATTTGTACCCAT

TTTGTTCAGTACTGCCTAGTCAATAATCAATGTCAACG-3'

B5-1D:
(SEQ ID NO: 102)
5'-ACATACCCAGAGACACTGAGAGAGACAGACAGACAGTA

AACAGAGGAGCACGATCCTATTAATAGTAATCAATTACG-3'

B5-1R: B5R was used.

B5-2D:
(SEQ ID NO: 103)
5'-GCTCAATTGTATCTTATGAAAACAATTTTTCAAAATAAA

ACAAGAGATATGATCCTATTAATAGTAATCAATTACG-3'

B5-2R: B5R was used.

B5-3D:
(SEQ ID NO: 104)
5'-CCTGTGCTGAATACCGTCTGCATATGTATAGGAAAGGGT

TAACTCAGCAGGGATCCTATTAATAGTAATCAATTACG-3'

B5-3R:
(SEQ ID NO: 105)
5'-TATGTGAATGGAAATAAAATAATCAAGCTTGTTAGAAT

TGTGTTCATAATGACCCTAGTCAATAATCAATGTCAACG-3'

B5-4D: B5D was used.

B5-4R:
(SEQ ID NO: 106)
5'-GAAAGTCTACAATTTTTTCAGTTTAAAATGGTATTTATTT

GTAACATGTACCCTAGTCAATAATCAATGTCAACG-3'

B5-5D: B5-1D was used.

B5-5R:
(SEQ ID NO: 107)
5'-CAAAGATGAAGGATGAGAGTGACTTCTGCCTTCATTAT

GTTATGTGTTCATATCCTAGTCAATAATCAATGTCAACG-3'

B5-6D:
(SEQ ID NO: 108)
5'-CAGTGAATTATTCACTTTGTCTTAGTTAAGTAAAAATAAA

ATCTGACTGTGATCCTATTAATAGTAATCAATTACG-3'

B5-6R:
(SEQ ID NO: 109)
5'-GAACAGACAGGTGAATGAGCACAGAGGTCATTTGTAAAC

CGTTTGTGGTTAGCCTAGTCAATAATCAATGTCAACG-3'

C14-1D:
(SEQ ID NO: 110)
5'-CTTTTTGGCTTCTGTGTTTAAGTTATTTTTCCCCTAGGCC

CACAAACAGAGTCGATCCTATTAATAGTAATCAATTACG-3'

C14-1R:
(SEQ ID NO: 111)
5'-AACCTTGGAAAAATTCTGTTGTGTTTAGAAGCATGTACC

AATCTATCACTCCTAGTCAATAATCAATGTCAACG-3'

-continued

C14-2D:
(SEQ ID NO: 112)
5'-CTATTCACTGTCTGTAGGATGAAAAAGTTAATAACAC

CCTGAGAGGTTTCGATCCTATTAATAGTAATCAATTACG-3'

C14-2R:
(SEQ ID NO: 113)
5'-CCTTAGATTAGTTTATTGTATTTTTTATCAGCTACTATA

AGGTTTACACACCCTAGTCAATAATCAATGTCAACG-3'

C14-3D:
(SEQ ID NO: 114)
5'-CAAGACCCTCAAAATTCAAAAATTTCCTTTATCTTGCTG

TAGCACCTCCTGCGATCCTATTAATAGTAATCAATTACG-3'

C14-3R:
(SEQ ID NO: 115)
5'-GGAGGGGATAGGAAGGGGATGAGGCCTAACAGGTTGA

TGATCTAGGCTTTACCTAGTCAATAATCAATGTCAACG-3'

C14-4D:
(SEQ ID NO: 116)
5'-CTCAAAAAGGAGATAATTCCAGCCCCTCGCCTTAAAGA

ATCCCTATCAAGTGATCCTATTAATAGTAATCAATTACG-3'

C14-4R: C14-1R was used.

C14-5D:
(SEQ ID NO: 117)
5'-CGCTTGAACCTGGGAGGCAGAGGTTGCAGTGAGCCGA

GATCACGCCGTTGGATCCTATTAATAGTAATCAATTACG-3'

C14-5R: C14-1R was used.
C14-6D: C14-4D was used.

C14-6R:
(SEQ ID NO: 118)
5'-TTAACTTTTTCATCCTACAGACAGTGAATAGTAAAGCTT

TCTGTGAAGACATACCCTAGTCAATAATCAATGTCAACG-3'

C14-7D: C14-2D was used.
C14-7R: C14-1R was used.
C14-8D: C14-3D was used.

C14-8R:
(SEQ ID NO: 119)
5'-AAATTATTTCCTGGTGGGCAATATTAGAATATGGGAAT

GTTTGCTTCTGAGCCTAGTCAATAATCAATGTCAACG-3'

C14-9D: C14-4D was used.
C14-9R: C14-3R was used.
C14-10D: C14-2D was used.
C14-10R: C14R was used.
C14-11D: C14-3D was used.
C14-11R: C14-2R was used.
C14-12D: C14-4D was used.
C14-12R: C14-8R was used.
C14-13D: C14-3D was used.
C14-13R: C14-1R was used.
C14-14D: C14-4D was used.
C14-14R: C14-2R was used.

As for the polynucleotide sequences of the respective fragments of A2, A2-1 corresponds to the polynucleotide sequence of nucleotides 1 to 3000 of SEQ ID NO: 10 in the Sequence Listing; A2-2 corresponds to the polynucleotide sequence of nucleotides 2801 to 5800 of SEQ ID NO: 10 in the Sequence Listing; A2-3 corresponds to the polynucleotide sequence of nucleotides 5401 to 8450 of SEQ ID NO: 10 in the Sequence Listing; A2-4 corresponds to the polynucleotide sequence of nucleotides 701 to 2700 of SEQ ID NO: 10 in the Sequence Listing; A2-5 corresponds to the polynucleotide sequence of nucleotides 701 to 2200 of SEQ ID NO: 10 in the Sequence Listing; A2-6 corresponds to the polynucleotide sequence of nucleotides 701 to 3700 of SEQ ID NO: 10 in the Sequence Listing; A2-7 corresponds to the polynucleotide sequence of nucleotides 2001 to 5000 of SEQ ID NO: 10 in the Sequence Listing; A2-8 corresponds to the polynucleotide sequence of nucleotides 4001 to 7000 of SEQ ID NO: 10 in the Sequence Listing; A2-9 corresponds to the polynucleotide sequence of nucleotides 1 to 3700 of SEQ ID NO: 10 in the Sequence Listing; A2-10 corresponds to the polynucleotide sequence of nucleotides 2001 to 5800 of SEQ ID NO: 10 in the Sequence Listing; A2-11 corresponds to the polynucleotide sequence of nucleotides 2801 to 7000 of SEQ ID NO: 10 in the Sequence Listing; A2-12 corresponds to the polynucleotide sequence of nucleotides 701 to 5800 of SEQ ID NO: 10 in the Sequence Listing; A2-13 corresponds to the polynucleotide sequence of nucleotides 2001 to 7000 of SEQ ID NO: 10 in the Sequence Listing; A2-14 corresponds to the polynucleotide sequence of nucleotides 2801 to 8450 of SEQ ID NO: 10 in the Sequence Listing; A2-15 corresponds to the polynucleotide sequence of nucleotides 1 to 5800 of SEQ ID NO: 10 in the Sequence Listing; A2-16 corresponds to the polynucleotide sequence of nucleotides 701 to 7000 of SEQ ID NO: 10 in the Sequence Listing; and A2-17 corresponds to the polynucleotide sequence of nucleotides 2001 to 8450 of SEQ ID NO: 10 in the Sequence Listing.

As for the polynucleotide sequences of the respective fragments of A7, A7-1 corresponds to the polynucleotide sequence of nucleotides 601 to 3600 of SEQ ID NO: 11 in the Sequence Listing; A7-2 corresponds to the polynucleotide sequence of nucleotides 3601 to 8420 of SEQ ID NO: 11 in the Sequence Listing; A7-3 corresponds to the polynucleotide sequence of nucleotides 5401 to 8420 of SEQ ID NO: 11 in the Sequence Listing; A7-4 corresponds to the polynucleotide sequence of nucleotides 3401 to 6400 of SEQ ID NO: 11 in the Sequence Listing; A7-5 corresponds to the polynucleotide sequence of nucleotides 1501 to 4500 of SEQ ID NO: 11 in the Sequence Listing; A7-6 corresponds to the polynucleotide sequence of nucleotides 4401 to 7400 of SEQ ID NO: 11 in the Sequence Listing; A7-7 corresponds to the polynucleotide sequence of nucleotides 2401 to 5400 of SEQ ID NO: 11 in the Sequence Listing; A7-8 corresponds to the polynucleotide sequence of nucleotides 1 to 3600 of SEQ ID NO: 11 in the Sequence Listing; A7-9 corresponds to the polynucleotide sequence of nucleotides 1501 to 5400 of SEQ ID NO: 11 in the Sequence Listing; A7-10 corresponds to the polynucleotide sequence of nucleotides 2401 to 6400 of SEQ ID NO: 11 in the Sequence Listing; A7-11 corresponds to the polynucleotide sequence of nucleotides 3401 to 7400 of SEQ ID NO: 11 in the Sequence Listing; A7-12 corresponds to the polynucleotide sequence of nucleotides 4401 to 8420 of SEQ ID NO: 11 in the Sequence Listing; A7-13 corresponds to the polynucleotide sequence of nucleotides 1 to 5400 of SEQ ID NO: 11 in the Sequence Listing; A7-14 corresponds to the polynucleotide sequence of nucleotides 1501 to 6400 of SEQ ID NO: 11 in the Sequence Listing; A7-15 corresponds to the polynucleotide sequence of nucleotides 2401 to 7400 of SEQ ID NO: 11 in the Sequence Listing; A7-16 corresponds to the polynucleotide sequence of nucleotides 3401 to 8420 of SEQ ID NO: 11 in the Sequence Listing; A7-17 corresponds to the polynucleotide sequence of nucleotides 1 to 6400 of SEQ ID NO: 11 in the Sequence Listing; and A7-18 corresponds to the polynucleotide sequence of nucleotides 1501 to 7400 of SEQ ID NO: 11 in the Sequence Listing.

As for the polynucleotide sequences of the respective fragments of A18, A18-1 corresponds to the polynucleotide sequence of nucleotides 1 to 5040 of SEQ ID NO: 12 in the Sequence Listing; A18-2 corresponds to the polynucleotide sequence of nucleotides 1001 to 6002 of SEQ ID NO: 12 in the Sequence Listing; A18-3 corresponds to the polynucleotide sequence of nucleotides 2001 to 7000 of SEQ ID NO: 12 in the Sequence Listing; and A18-4 corresponds to the polynucleotide sequence of nucleotides 3000 to 7000 of SEQ ID NO: 12 in the Sequence Listing.

As for the polynucleotide sequences of the respective fragments of B5, B5-1 corresponds to the polynucleotide sequence of nucleotides 1 to 4001 of SEQ ID NO: 13 in the Sequence Listing; B5-2 corresponds to the polynucleotide sequence of nucleotides 1 to 3200 of SEQ ID NO: 13 in the Sequence Listing; B5-3 corresponds to the polynucleotide sequence of nucleotides 2491 to 5601 of SEQ ID NO: 13 in the Sequence Listing; B5-4 corresponds to the polynucleotide sequence of nucleotides 5373 to 8401 of SEQ ID NO: 13 in the Sequence Listing; B5-5 corresponds to the polynucleotide sequence of nucleotides 901 to 4001 of SEQ ID NO: 13 in the Sequence Listing; and B5-6 corresponds to the polynucleotide sequence of nucleotides 4001 to 7000 of SEQ ID NO: 13 in the Sequence Listing.

As for the polynucleotide sequences of the respective fragments of C14, C14-1 corresponds to the polynucleotide sequence of nucleotides 960 to 4015 of SEQ ID NO: 14 in the Sequence Listing; C14-2 corresponds to the polynucleotide sequence of nucleotides 1987 to 5014 of SEQ ID NO: 14 in the Sequence Listing; C14-3 corresponds to the polynucleotide sequence of nucleotides 4020 to 7119 of SEQ ID NO: 14 in the Sequence Listing; C14-4 corresponds to the polynucleotide sequence of nucleotides 960 to 8141 of SEQ ID NO: 14 in the Sequence Listing; C14-5 corresponds to the polynucleotide sequence of nucleotides 960 to 6011 of SEQ ID NO: 14 in the Sequence Listing; C14-6 corresponds to the polynucleotide sequence of nucleotides 4939 to 8141 of SEQ ID NO: 14 in the Sequence Listing; C14-7 corresponds to the polynucleotide sequence of nucleotides 960 to 5014 of SEQ ID NO: 14 in the Sequence Listing; C14-8 corresponds to the polynucleotide sequence of nucleotides 2994 to 7119 of SEQ ID NO: 14 in the Sequence Listing; C14-9 corresponds to the polynucleotide sequence of nucleotides 4020 to 8141 of SEQ ID NO: 14 in the Sequence Listing; C14-10 corresponds to the polynucleotide sequence of nucleotides 1 to 5014 of SEQ ID NO: 14 in the Sequence Listing; C14-11 corresponds to the polynucleotide sequence of nucleotides 1987 to 7119 of SEQ ID NO: 14 in the Sequence Listing; C14-12 corresponds to the polynucleotide sequence of nucleotides 2994 to 8141 of SEQ ID NO: 14 in the Sequence Listing; C14-13 corresponds to the polynucleotide sequence of nucleotides 960 to 7119 of SEQ ID NO: 14 in the Sequence Listing; and C14-14 corresponds to the polynucleotide sequence of nucleotides 1987 to 8141 of SEQ ID NO: 14 in the Sequence Listing.

The start and end points of the respective fragments on the full-length sequence are also shown in FIGS. 20 and 21.

10-2) Evaluation of DNA Elements Having Different Sequence Lengths

Each plasmid constructed in 10-1) was evaluated using the host cell CHO-K1 (ATCC) and the transfection reagent Lipofectamine 2000.

In the same manner as in 7-3), antibiotic selection with hygromycin was performed after transfection, whereby a stably expressing polyclonal cell line was established. The thus established cell line was subjected to medium replacement on the day before measurement, and a given number of the cells were seeded onto a 24-well plate. At 24 hours after plating the cells, the culture supernatant was collected, and the activity of SEAP was measured.

The measurement results are shown in FIGS. 10, 12, 14, 16, and 18. It was confirmed that not only the full-length DNA elements, but also clones having a sequence length shorter than the full length have an effect on enhancement of expression. Based on the results, it was confirmed that DNA elements A2, A7, A18, B5, and C14 have the activity of enhancing foreign gene expression even in cases where they have a sequence length shorter than the full length. However, they exhibit the highest effect when the sequence length is the full length.

Example 11

Effect Using Host Cells Other than CHO Cell Line

A CHO cell line was used as the cell line in the evaluation in Examples 7 to 10. However, in Example 11, an HEK293 cell line was selected as a cell line other than the CHO cell line. The HEK293 cell line was subjected to static culture at 37° C. in the presence of 5% $CO_2$ using DMEM medium (Invitrogen) containing 10% FCS, and a given number of the cells were seeded onto a 6-well plate on the day before transfection. In order to evaluate the SEAP expression vector containing each DNA element constructed in 8-2), transfection was performed using each plasmid and the transfection reagent Lipofectamine 2000 (Invitrogen). Antibiotic selection with hygromycin was performed for about 2 weeks starting 2 days after transfection, whereby a stably expressing polyclonal cell line was established. The thus established cell line was subjected to medium replacement on the day before measurement, and a given number of the cells were seeded onto a 24-well plate. At 24 hours after plating the cells, the culture supernatant was collected, and the activity of SEAP was measured. The activity of SEAP in the culture supernatant was measured using the SensoLyte™ pNPP Secreted Alkaline Phosphatase Reporter Assay (ANASPEC).

The measurement results are shown in FIG. 19. In the same manner as in Example 3, it was confirmed that each DNA element is also highly effective in enhancing the expression of a foreign gene (SEAP) in the HEK293 cell line.

INDUSTRIAL APPLICABILITY

By introducing the foreign gene expression unit using a promoter according to the invention, or the foreign gene expression vector according to the invention, into mammalian host cells, it becomes possible to improve the production of a foreign gene of a therapeutic protein, an antibody, or the like.

The invention claimed is:

1. A gene expression unit for the expression of a foreign gene in a host cell, comprising:
    (i) a polynucleotide consisting of a nucleotide sequence of SEQ ID NO:1 in the Sequence Listing and having promoter activity,
    (ii) the foreign gene, wherein the foreign gene is artificially introduced into the host cell, and
    (iii) a transcription terminator region.

2. The gene expression unit according to claim 1, wherein the foreign gene encodes a multimeric protein.

3. The gene expression unit according to claim 1, wherein the foreign gene encodes a heteromultimeric protein.

4. The gene expression unit according to claim 1, wherein the foreign gene encodes an antibody or a functional fragment thereof.

5. A gene expression vector comprising the gene expression unit according to claim 1.

6. The gene expression vector comprising the gene expression unit according to claim 5, and further comprising one or more of the following polynucleotides:

(1) a polynucleotide consisting of the nucleotide sequence represented by SEQ ID NO: 10 in the Sequence Listing;
(2) a polynucleotide consisting of the nucleotide sequence represented by SEQ ID NO: 11 in the Sequence Listing;
(3) a polynucleotide consisting of the nucleotide sequence represented by SEQ ID NO: 12 in the Sequence Listing;
(4) a polynucleotide consisting of the nucleotide sequence represented by SEQ ID NO: 13 in the Sequence Listing;
(5) a polynucleotide consisting of the nucleotide sequence represented by SEQ ID NO: 14 in the Sequence Listing;
(6) a polynucleotide comprising at least 3000 consecutive nucleotides of a nucleotide sequence represented by any one of SEQ ID NOs:10 to 14 in the Sequence Listing;
(7) a polynucleotide comprising at least 2000 consecutive nucleotides of a nucleotide sequence represented by any one of SEQ ID NOs:10 to 14 in the Sequence Listing;

(8) a polynucleotide comprising a polynucleotide sequence having an identity of 95% or more to the nucleotide sequence of the polynucleotide according to any one of the above (1) to (7); or
(9) a polynucleotide comprising a nucleotide sequence having an identity of 99% or more to the nucleotide sequence of the polynucleotide according to any one of the above (1) to (7).

7. A transformed host cell into which the gene expression vector according to claim 5 has been introduced.

8. A transformed host cell into which the gene expression vector according to claim 5 and an element vector have been introduced.

9. The transformed host cell according to claim 7, wherein the cell is a cultured cell from a mammal.

10. The transformed host cell according to claim 9, wherein the cultured cell from the mammal is a COS-1 cell, a 293 cell, or a Chinese Hamster Ovary (CHO) cell.

11. A method for producing a protein comprising culturing the transformed cell according to claim 7 and obtaining a protein expressed from the foreign gene in the culture.

* * * * *

SEQUENCE LISTING

<160> NUMBER OF SEQ ID NOS: 119

<210> SEQ ID NO 1
<211> LENGTH: 2348
<212> TYPE: DNA
<213> ORGANISM: Homo sapiens

<400> SEQUENCE: 1

| | | | | | |
|---|---|---|---|---|---|
| atttatgtat | attaacagca | cattaacagc | taaaaagaaa | aactcacata | atcatattag | 60 |
| ttcatagaaa | caatgcattt | gacatactcc | aacatccatt | catgatttta | ttttattttg | 120 |
| tatttatata | ttttttttga | gatggagtct | cgctgtcacc | caggctggag | tgcaatggct | 180 |
| cgatctcggc | tcactgcagg | ctccgccccc | ggcggttcac | gccattctcc | tgcctcagcc | 240 |
| tcccgagtag | ctgggactac | aggcgcccgc | cacctcgccc | agctaatttt | ttgtattttt | 300 |
| agtagagacg | gggtttcacc | gtgttagcca | ggatggtctc | gatctcctga | cctcgtgatc | 360 |
| cacccgcctc | ggcctcccaa | agtgctggga | ttacaggcgt | gagccaccgt | gcccggccca | 420 |
| tgattttaaa | aaaacctctc | agaaatagaa | acagagggaa | cttcctgaat | ttgattaaaa | 480 |
| atacctgcaa | aatcctagag | ctaatattat | acttaatggt | gaaagactga | atggttttcc | 540 |
| cctaagatgg | agaacaaggc | acggatgtcc | ttgctcacca | ctcctattca | acaaaggact | 600 |
| ggaaccagaa | ataaacttta | atttttttt | ttctcaagtg | ataggttcac | agagaaaaag | 660 |
| ctttactgga | tgaactttta | gattactact | tttatagagc | agcagagata | aaagccaggt | 720 |
| cgaaaagtgc | atgtggagta | aggaaatgga | cctagttcga | caaagggct | cagaacgact | 780 |
| gcccagatga | gattgtagac | gcagctgtag | tttactttct | atctggaaga | aacttcaagt | 840 |
| tatccttaat | tttccaagga | gacagtcact | tacctttaa | aaaacattat | tagagaagca | 900 |
| ccgggcggga | gcatatctag | cattaaaaat | gtgggatgaa | taccatctct | gcttggtaaa | 960 |
| ggtggttggg | aatcctgaga | gagggcacct | agtgtggctt | ctgcattttt | cacagtgcct | 1020 |
| ggaccacggc | tgaaagtaac | tcttgcatga | catttgacag | aagaggaaac | cgaagctcag | 1080 |
| attaaattcc | ctgtccacag | cgggatcatt | cggcacgagt | tcctccctgt | ctggaatgct | 1140 |
| cttccccagc | aatagatcct | gcggctcttc | cgtgtctcag | tctaatgtca | ttccgttcca | 1200 |
| ggattcccga | cttcttaaag | cataaataat | ccctccccac | cctctcattg | tactgttatg | 1260 |
| taacttatta | caatatgtca | ttatatattt | agtcatactg | ctttaggtaa | tgtcttctcc | 1320 |
| actgaactgt | aagctccatg | agggcaagag | ttcagtcggt | tttacttaat | aattagcacc | 1380 |
| tagtacagta | ctagcataga | atgaaggcct | cgcaattttt | tttaaattta | tttttagaca | 1440 |
| gggtcttgcg | ctgtcgccca | ggctggagtg | cagtggtgca | acctcggctc | acggcagcct | 1500 |
| cgacctttcg | gctccagcga | tcctcccgcg | tcggcctccg | gggtagctgg | gactgcaggc | 1560 |
| gcgcaccacc | atgactggct | aatttttttt | ttttttttt | tgtagacatg | gggtctcgcc | 1620 |
| atgttgccca | ggctggttcc | tgagctcaag | tgatcctcct | gcctcggcct | cccaaagtgc | 1680 |
| tgggattaca | ggcgtgagcc | tcagcgccca | gccaagttag | cctttttaa | acgtcctgtc | 1740 |
| tccggaggtt | gccgaagttg | gttttcttcg | gcctccttct | ctctcccagg | cccagggctg | 1800 |
| ggacgaggcc | ggttcccgcc | tgcaacctgc | actgaagacg | ggaaccttgg | gagccggtac | 1860 |
| cggaacgctc | ggaaacggca | ccaaagtacg | aatcctaggg | cggaaaagcg | ttaccaagac | 1920 |
| actcgtcccc | agagccgctt | cctgggactc | tctagcctcc | taccgcttct | cagtgatgtt | 1980 |
| ccggtttccg | ccctcctcct | cgcgctgttt | ccgcctcttg | ccttcggacg | ccggattttg | 2040 |
| acgtgctctc | gcgagatttg | ggtctcttcc | taagccggcg | ctcggcaagg | taggttggcg | 2100 |

```
gcctgctctc cgacagaact tttcttcttg ggttgaggaa aacgcctttt ggagtcaggc    2160
cctggagggg cgagccttgc tcacagggtg gggatacagc cgattacccg ccctgtgctt    2220
tccgatggct tctgcggggc gagcggggcc tggccggggg gtgcgggcgg gagggcgagc    2280
cagcggcgcc tgcagcccgg gccgcgtaac gctgaccgct gtgccttcag ttctcccagg    2340
agaaagcc                                                             2348
```

<210> SEQ ID NO 2
<211> LENGTH: 3345
<212> TYPE: DNA
<213> ORGANISM: Homo sapiens

<400> SEQUENCE: 2

```
ctaaagtgat tcctaaagaa ttcttccctt ttatcacttc cagtaggcct ctgtgaaacc      60
aaatctacct ccgcttacaa gaaagatgct gggctggcct tctctcaaag tctttccaaa     120
cttttcttgg cattgactta gacaccctag gaatctaact tgagaaaatg ttttcattaa     180
aaaaaatctc aggaagtaaa acctcctgaa tgattactga gttgacataa atcttatgtg     240
tatattctta tcagaaaaaa agtatcttca ttttgtggga caccaattca tgtattatta     300
ttattttgag acaaagtttc gctcttgttg cccaggctgg agtgcaatgg cgcgatctcc     360
acttactgca acctccacct cctgagttca agtgattctc gtgcctcagc ctccctagta     420
gctggaacta caggcatgtg ccaccacacc cagctaattt tttgtaactt tagtagagat     480
ggggtttcac catgttggcc aggatggact cgaactcctg accacaggtg atctgcccac     540
ctcagcttcc caaagtgctg ggattacagg catgagccac cgcgcccagt cgctgggtct     600
tacagtaact ttatgtttaa cattttgagg aaatgctatt cttttccaaa gtgactgcac     660
catttcatat ttgcactagc actgtacgga cattcccatt tctctgtcct agtgagtgtg     720
aaatggtatc tcactgcagt tccagtttgt atttccctga tggctaatga tgtggatcat     780
ttcatgtgtt cattggccac agagaaatgt ctatttggat tctttaccca ttttttcaatt    840 gggttatttg tctttatagg tttgttgttg ttgagacaga gtcttgctct gtcactcagg     900
ctggagtgca gtggcattat cacagctaac tgcagtctag aactgctggg ctcacgtgat     960
catcccagct cagcctctcg agtaactggg actacaggca tgcgccacca gccccagcta    1020
attattttat tttttgtaga gacagggtct tactatgttg cctaggccgg tcttgaactc    1080
ctgggctcaa gcaaatctcc cacctcagac tcccaaagta ttggaattat aggtgtgaac    1140
catagtgctc agccaatttg cacaataatc ttaaatacaa aagctaagca aaacaaatca    1200
agagcatctt taaaaactag gcagtctggg aggcaggggc tgccgtgagc cgtgagatgg    1260 caccttttgca ttccagccta ggtgacagag ggaggccctg tctaaaaaaa accaaaaacc    1320
aaaaaacaaa acaaaacaaa aacatctag gcagtagctc gtgcccgtaa tcccagctac    1380
tcaggaggct gaggcgagag aatcgtttga gcccaggagt tcaagaccag cctgggcaac    1440
agagtgagac cccatttcta aaaatgaac aaagaaaaac taggcagttt cgcccagtgg    1500
ttagaagcgt ggagtttgga gtcaagtctc caaatttcat cttccacata tgcaaaatgg    1560
agacaataat aggggtacgt tatagaattg tggtaggcat agtgaactcc atcgcatgtt    1620
agctgttttc gttactattt actgtctaaa ttcggtgatg aaattattag gaagtctctg    1680
tcttgttctc ttctgaccac taagaggcgc acttcggagt agaagaaacg cgggcggaaa    1740
tagcccaaaa gcggattggc ttcgacttct ggcggaagta aattcctccc tccaccaggt    1800
```

-continued

| | |
|---|---|
| cttattagct cagaaagaat tccaaatttc tacgtagtcc caaggatagg tagaatacat | 1860 |
| ttctcagtcc tattcctagt tattattgtc tattaaaaca tgtatactca gaattttttgc | 1920 |
| ggcattattt tttgacgtgt ctttatttta tttaaaagag ccggagccgg aagtgcttgc | 1980 |
| cttttttccct gctaggaccc aggggttacg acccatcagc ccttgcgcgc caccgtccct | 2040 |
| tctctcttcc tcggcgctgc ctacggaggt ggcagccatc tccttctcgg taagtgttaa | 2100 |
| tccgtggcaa tccgcattcc tgcgggattc atctggcccc gtcgcccagt ggtgcgagg | 2160 |
| cctccccttc agcgcggtag tgtctgtggg tattgttatt gtcagcttac tggagcgtgt | 2220 |
| acaggaacag aacgaagccg ccgagttgat agggctttgc gtcccagagc ctcctgccct | 2280 |
| ccgcctgtat tcagagctgc gggctgcttg tttgttcctt ggcggtggag ggtgctagtt | 2340 |
| gaggccagac ttcggggtct cctgggggcc gtgggacgac caggggtggc ccagcttgac | 2400 |
| agctttcagc tgggatctgt ggatcccagc gctcaccaat gtcggcccac gtgtattcgt | 2460 |
| tcatgccatg gccggcttct tccgctgcag tctctggccc gagggctgct gctgcgggac | 2520 |
| cgccaaggaa agacgagctg taggtcggct ggtccagctg caggcagaaa ttctggtagt | 2580 |
| atctctggga atatgaagat gcaactgccc ccaccttgcc ttcgaggata tcatgggcca | 2640 |
| gaaggcagag tcgttttgaa tacgtggttc attgagtacc cactctgggc cagttgatgg | 2700 |
| ctgcgaagag agcagaaggg gtgctgctgt aggaaatcaa tggctcggaa gaccacactg | 2760 |
| aggaaggtgt gagttgatac tggaagatct ccaggtttga ggcatcttca gaggtatatg | 2820 |
| gtggttttgt gtgtgttgag ggtgtggtag cgcagcagct ccctagggaa ttagaaggtt | 2880 |
| ttattgaaca tttaccctgt gacaggcact gcaggcattc agcgcgcagt gtcatcttca | 2940 |
| ttttacaggt gaggaaaaga ctcaggttca agtagatggt caaggccagt actaccggaa | 3000 |
| ggaccatctg ggggttcgga cactggtggg gtgggatttg ctgccccttg caaattgaga | 3060 |
| gtgtcttggg gtcagttttg atttgctcag ctgttggcat tctttgggct ctgagtgggt | 3120 |
| gaggtgaccc ttgacctcct gggatcgcat ctggagagtg cctagtattc tgccagcttc | 3180 |
| ggaaagggag ggaaagcaag cctggcagag gcacccattc cattcccagc ttgctccgta | 3240 |
| gctggcgatt ggaagacact ctgcgacagt gttcagtccc tgggcaggaa agcctccttc | 3300 |
| caggattctt cctcacctgg ggccgcttct tccccaaaag gcatc | 3345 |

<210> SEQ ID NO 3
<211> LENGTH: 3337
<212> TYPE: DNA
<213> ORGANISM: Homo sapiens

<400> SEQUENCE: 3

| | |
|---|---|
| atggtggcac aatcatggtt cactgcagcc tcaaacttct aggctcaagt gatcctccag | 60 |
| cctcagcctc ctgagtaggt gggactaaag gtgtgtgcta acacctggg ctaattaaaa | 120 |
| aaaaaaaatt tgtagagatg ggcgtctcgc tatgttgccc aggctgatct ttaactacag | 180 |
| gtctcagtga tctttctgta tcagcctccc gaagtgctag gattaacagg catgggccac | 240 |
| tgtacctggc tgtctttgaa gttttttaata agattgccat atctctctca agactgatca | 300 |
| agaaaaaatg caaatacaaa tttaaagaga gggaaaaata gtattatgga actgggttaa | 360 |
| gtaccttaag ggaaaactac aacaatgaga ccactattct tatctacttg ggtggggggaa | 420 |
| ggcacggaca gagacgtaaa caacagcata gtgtgccaag ggctcccatc tcctgttctc | 480 |
| ttctgctctg caaagtctct cttaaaatat agagaacata ttgcaagtaa atacattcat | 540 |
| tagtgcattt attcaaaaac cacatttgtc tctctatgca agcttccatc tcaatgcctg | 600 |

```
gcacagagac gaaaaggatt tcagaggaca aaaatcaaag gactggaaag gagggaagta      660
gctgatgaca aggtcggggg agaagcagct atttgagagt gagcagaggg aaggatataa      720
ccagagcctt ccatctggtg ttgtgacaaa gatggcagtg atgtgaggct tgatagaatc      780
aataggcctc acagttcaag acagactaca tgccctcagt cacttgcctg ctttcttggt      840
ttgctagatg gattagaaat actagaagga aagttgagtg ggtactggga tatcctatcc      900
aaatcctctc ttctggggca atgcagctgc ctcacagcaa ccacgttgtg gatcacctga      960
ccccgccttt ctcagcttcc tggaggtgca ttctaagagc gctccccata agccaacact     1020
caagtctctt cgaggtgtgt ttccagggag cctgatctaa gattaaaaac ttaaaggccc     1080
cttttagaat tgtcttttac agcccaggca aagagttctt tactttttta gaggtcatga     1140
atccctttga caaggtgatg aaagccaggg accctcttct cagaaaaata cacacgtgcg     1200
cttaatgtaa aattttacat actgttttaa aggttaaact ttaccaccca tgaaaagcct     1260
caagtagttc tttgtacata atcataagat tagcaaccat ttactgagca cttcctctct     1320
ataagaccct gtgctaagtg ctttaacttc ataatgcctt tgatcatgac ataacatggc     1380
acggtagttc ctaatatctt ccttttagag atttaagggc ttgctcaaag taacatagct     1440
aataattagc agacactgga ttaaaatccc aatttgtttg taaagcttgt gctctgaata     1500
aatgacaagg aaagagaagg gaaggttgaa gaagggaagg ttcttgaagg tccctggtcc     1560
ttgaaggtcc cttaaccata aatgtcaaga gttgggattt aaacccaggt ctaacgccag     1620
agctggcgcc ctttagatta aaagtgcagt gtccatgaca acgaaagaag ttgattttgt     1680
cccacctttg ctctttgcgg cttttcattt gcgtttgttt ccacagcgat ttccaataga     1740
tttctgcgtg gccttgacac agacagctag tgtgaatccc cgcccacaga ggggcggcac     1800
gttggttgcc gtacaacgtg gtggttccct gcatctctgc ccacgtcgga gaggtgcgtc     1860
ggcttccgta caacacggat actctctctc tgacgcaact tcctgtcctg cgcaattcta     1920
tttgaccttt gaactggcaa aggctttttt cttcctcttc cggggacgtt gtctgcaggt     1980
atggatgttg ttctcttttc cctgtcttta tttccttacc aatcggctgc catccgagga     2040
gctgaggaag cctagagctc tcagaagcag tcctttgagc tggtgtaggg gtaagggca     2100 caacagggag gttggtggtg aggaagttcc ttactttgat ctttggaaat cccttgttcc     2160
tggtggcacc tccaaagccg tgagtagcca cagctcacca cccgggactt tgctgcattc     2220
caagtgtagc gtttggagac taacgagttg tggtttggcg gtttgagtct ggaaaatcgc     2280
caaacgtttt catattttac acccacgttt tcacagcacg cctgtacgtg tccttagtct     2340
ttgggagggc agggtccggc gagttcgggt ggtttcgcta tttggcttct gcgtccaagg     2400
cccatgtcaa ggaagagaaa aatgtgttag aagtttctgt cttgcttttg gagatgcaaa     2460
cagaataatg gcttcataaa tcactcgcac tggttttacg tgtcaagttt tggtgtctgg     2520
taattctgtt ttagtttaat tttagtgaga ggcttgtgac aacaaatgag gtggttacaa     2580
ggggtggaat gggaagatta aattagttca agtattgatt atgttttacg ttgggtagtt     2640
cccttaacga agttgctcgt atgcatatct gtataaccga tttgctaaat aacatcacga     2700
tgtttccaga agtgggaaga aagcaggtgc cataacccaa agaaacttgt gtaatatcaa     2760
aattagtatt aaagggtatg cctttacgca ggtggtgctt tagggcaaga cattgaaccc     2820
tgatatgtgc caggcattgt gttgggacgg atagcccacg tcgtttaatc ctaatgcacag     2880 ctgtataaag tagacagaat tcccatgtta gagataagga ggctagctcc ttgcccttta     2940
```

```
tattcccagt aaatggcata gctaaggatt cgacttcaga gctcactttt tgtgctcttt     3000
gtttaaagcg gtgtttctcc aactgggctc gtggcacttt tctggacacc actccaaaca     3060
aaattagact ctgagtaagg agcctggtca tcagaacgtt aaggaagtgc cacgtttgat     3120
taccatcagg aaagctaaca ttcttggcct cttgtttatc agtcaccttt aaatacaagt     3180
agttttaaaa tgtggaataa tacatcttaa tttaagggtg ttacatacaa ggatatgtat     3240
gtgaatgaaa tagaccacat gatactgttt tgagatttta tttacttta caatggaaag      3300 atttgatgtt actctattct aatttaggc actcaga                              3337

<210> SEQ ID NO 4
<211> LENGTH: 1361
<212> TYPE: DNA
<213> ORGANISM: Homo sapiens

<400> SEQUENCE: 4
cctagtgtgg cttctgcatt tttcacagtg cctggaccac ggctgaaagt aactcttgca       60
tgacatttga cagaagagga aaccgaagct cagattaaat tccctgtcca cagcgggatc      120
attcggcacg agttcctccc tgtctggaat gctcttcccc agcaatagat cctgcggctc      180
ttccgtgtct cagtctaatg tcattccgtt ccaggattcc cgacttctta aagcataaat      240
aatccctccc caccctctca ttgtactgtt atgtaactta ttacaatatg tcattatata      300
tttagtcata ctgctttagg taatgtcttc tccactgaac tgtaagctcc atgagggcaa      360
gagttcagtc ggttttactt aataattagc acctagtaca gtactagcat agaatgaagg      420
cctcgcaatt tttttttaaat ttattttag acagggtctt gcgctgtcgc ccaggctgga      480
gtgcagtggt gcaacctcgg ctcacggcag cctcgacctt tcggctccag cgatcctccc      540
gcgtcggcct ccggggtagc tgggactgca ggcgcgcacc accatgactg gctaattttt      600 ttttttttt ttttgtagac atggggtctc gccatgttgc ccaggctggt tcctgagctc      660
aagtgatcct cctgcctcgg cctcccaaag tgctgggatt acaggcgtga gcctcagcgc      720
ccagccaagt tagccttttt taaacgtcct gtctccggag gttgccgaag ttggttttct      780
tcggcctcct tctctctccc aggcccaggg ctggacgag gccggttccc gcctgcaacc      840
tgcactgaag acgggaacct tgggagccgg taccggaacg ctcggaaacg gcaccaaagt      900
acgaatccta gggcggaaaa gcgttaccaa gacactcgtc cccagagccg cttcctggga      960
ctctctagcc tcctaccgct tctcagtgat gttccggttt ccgcctcct cctcgcgctg     1020 tttccgcctc ttgccttcgg acgccggatt ttgacgtgct ctcgcgagat ttgggtctct     1080
tcctaagccg gcgctcggca aggtaggttg gcggcctgct ctccgacaga acttttcttc     1140
ttgggttgag gaaaacgcct tttggagtca ggccctggag gggcgagcct tgctcacagg     1200
gtggggatac agccgattac ccgccctgtg ctttccgatg gcttctgcgg ggcgagcggg     1260
gcctggccgg ggggtgcggg cgggagggcg agccagcggc gcctgcagcc cgggccgcgt     1320
aacgctgacc gctgtgcctt cagttctccc aggagaaagc c                        1361

<210> SEQ ID NO 5
<211> LENGTH: 867
<212> TYPE: DNA
<213> ORGANISM: Homo sapiens

<400> SEQUENCE: 5
cctcggctca cggcagcctc gacctttcgg ctccagcgat cctcccgcgt cggcctccgg       60
ggtagctggg actgcaggcg cgcaccacca tgactggcta attttttttt ttttttttt      120
```

| | |
|---|---|
| gtagacatgg ggtctcgcca tgttgcccag gctggttcct gagctcaagt gatcctcctg | 180 |
| cctcggcctc ccaaagtgct gggattacag gcgtgagcc cagcgcccag ccaagttagc | 240 |
| cttttttaaa cgtcctgtct ccggaggttg ccgaagttgg ttttcttcgg cctccttctc | 300 |
| tctcccaggc ccagggctgg gacgaggccg gttcccgcct gcaacctgca ctgaagacgg | 360 |
| gaaccttggg agccggtacc ggaacgctcg gaaacggcac caaagtacga atcctagggc | 420 |
| ggaaaagcgt taccaagaca ctcgtcccca gagccgcttc ctgggactct ctagcctcct | 480 |
| accgcttctc agtgatgttc cggtttccgc cctcctcctc gcgctgtttc gcctcttgc | 540 |
| cttcggacgc cggattttga cgtgctctcg cgagatttgg gtctcttcct aagccggcgc | 600 |
| tcggcaaggt aggttggcgg cctgctctcc gacagaactt ttcttcttgg gttgaggaaa | 660 |
| acgcctttg gagtcaggcc ctggagggg gagccttgct cacagggtgg ggatacagcc | 720 |
| gattacccgc cctgtgcttt ccgatggctt ctgcggggcg agcggggcct ggccgggggg | 780 |
| tgcgggcggg agggcgagcc agcggcgcct gcagcccggg ccgcgtaacg ctgaccgctg | 840 |
| tgccttcagt tctcccagga gaaagcc | 867 |

<210> SEQ ID NO 6
<211> LENGTH: 2372
<212> TYPE: DNA
<213> ORGANISM: Homo sapiens

<400> SEQUENCE: 6

| | |
|---|---|
| cctctcgagt aactgggact acaggcatgc gccaccagcc ccagctaatt attttatttt | 60 |
| ttgtagagac agggtcttac tatgttgcct aggccggtct tgaactcctg ggctcaagca | 120 |
| aatctcccac ctcagactcc caaagtattg gaattatagg tgtgaaccat agtgctcagc | 180 |
| caatttgcac aataatctta aatacaaaag ctaagcaaaa caaatcaaga gcatctttaa | 240 |
| aaactaggca gtctgggagg caggggctgc cgtgagccgt gagatggcac ctttgcattc | 300 |
| cagcctaggt gacagaggga ggccctgtct aaaaaaaacc aaaaaccaaa aacaaaaaca | 360 |
| aaacaaaaaa catctaggca gtagctcgtc ccgtaatcc cagctactca ggaggctgag | 420 |
| gcgagagaat cgtttgagcc caggagttca agaccagcct gggcaacaga gtgagacccc | 480 |
| atttctaaaa aatgaacaaa gaaaaactag gcagtttcgc ccagtggtta aagcgtgga | 540 |
| gtttggagtc aagtctccaa atttcatctt ccacatatgc aaaatggaga caataatagg | 600 |
| ggtacgttat agaattgtgg taggcatagt gaactccatc gcatgttagc tgttttcgtt | 660 |
| actatttact gtctaaattc ggtgatgaaa ttattaggaa gtctctgtct tgttctcttc | 720 |
| tgaccactaa gaggcgcact tcggagtaga agaaacgcgg gcggaaatag cccaaaagcg | 780 |
| gattggcttc gacttctggc ggaagtaaat tcctccctcc accaggtctt attagctcag | 840 |
| aaagaattcc aaatttctac gtagtcccaa ggataggtag aatacatttc tcagtcctat | 900 |
| tcctagttat tattgtctat taaaacatgt atactcagaa ttttgcggc attattttt | 960 |
| gacgtgtctt tattttattt aaaagagccg gagccggaag tgcttgcctt tttccctgct | 1020 |
| aggacccagg ggttacgacc catcagccct tgcgcgccac cgtcccttct ctcttcctcg | 1080 |
| gcgctgccta cggaggtggc agccatctcc ttctcggtaa gtgttaatcc gtggcaatcc | 1140 |
| gcattcctgc gggattcatc tggccccgtc gcccagtggt gcggaggcct ccccttcagc | 1200 |
| gcggtagtgt ctgtgggtat tgttattgtc agcttactgg agcgtgtaca ggaacagaac | 1260 |
| gaagccgccg agttgatagg gctttgcgtc ccagagcctc ctgccctccg cctgtattca | 1320 |

| | |
|---|---|
| gagctgcggg ctgcttgttt gttccttggc ggtggagggt gctagttgag gccagacttc | 1380 |
| ggggtctcct gggggccgtg ggacgaccag gggtggccca gcttgacagc tttcagctgg | 1440 |
| gatctgtgga tcccagcgct caccaatgtc ggcccacgtg tattcgttca tgccatggcc | 1500 |
| ggcttcttcc gctgcagtct ctggcccgag ggctgctgct gcgggaccgc caaggaaaga | 1560 |
| cgagctgtag gtcggctggt ccagctgcag gcagaaattc tggtagtatc tctgggaata | 1620 |
| tgaagatgca actgccccca ccttgccttc gaggatatca tgggccagaa ggcagagtcg | 1680 |
| ttttgaatac gtggttcatt gagtacccac tctgggccag ttgatggctg cgaagagagc | 1740 |
| agaaggggtg ctgctgtagg aaatcaatgg ctcggaagac cacactgagg aaggtgtgag | 1800 |
| ttgatactgg aagatctcca ggtttgaggc atcttcagag gtatatggtg gttttgtgtg | 1860 |
| tgttgagggt gtggtagcgc agcagctccc tagggaatta aaggtttta ttgaacattt | 1920 |
| accctgtgac aggcactgca ggcattcagc gcgcagtgtc atcttcattt tacaggtgag | 1980 |
| gaaaagactc aggttcaagt agatggtcaa ggccagtact accggaagga ccatctgggg | 2040 |
| gttcggacac tggtggggtg ggatttgctg ccccttgcaa attgagagtg tcttggggtc | 2100 |
| agttttgatt tgctcagctg ttggcattct ttgggctctg agtgggtgag gtgacccttg | 2160 |
| acctcctggg atcgcatctg gagagtgcct agtattctgc cagcttcgga aagggaggga | 2220 |
| aagcaagcct ggcagaggca cccattccat tcccagcttg ctccgtagct ggcgattgga | 2280 |
| agacactctg cgacagtgtt cagtccctgg gcaggaaagc ctccttccag gattcttcct | 2340 |
| cacctggggc cgcttcttcc ccaaaaggca tc | 2372 |

<210> SEQ ID NO 7
<211> LENGTH: 1862
<212> TYPE: DNA
<213> ORGANISM: Homo sapiens

<400> SEQUENCE: 7

| | |
|---|---|
| gcagtttcgc ccagtggtta gaagcgtgga gtttggagtc aagtctccaa atttcatctt | 60 |
| ccacatatgc aaaatggaga caataatagg ggtacgttat agaattgtgg taggcatagt | 120 |
| gaactccatc gcatgttagc tgttttcgtt actatttact gtctaaattc ggtgatgaaa | 180 |
| ttattaggaa gtctctgtct tgttctcttc tgaccactaa gaggcgcact tcggagtaga | 240 |
| agaaacgcgg gcgaaatag cccaaaagcg gattggcttc gacttctggc ggaagtaaat | 300 |
| tcctccctcc accaggtctt attagctcag aaagaattcc aaatttctac gtagtcccaa | 360 |
| ggataggtag aatacatttc tcagtcctat tcctagttat tattgtctat taaaacatgt | 420 |
| atactcagaa tttttgcggc attatttttt gacgtgtctt tattttattt aaaagagccg | 480 |
| gagccggaag tgcttgcctt tttccctgct aggacccagg ggttacgacc catcagccct | 540 |
| tgcgcgccac cgtcccttct ctcttcctcg gcgctgccta cggaggtggc agccatctcc | 600 |
| ttctcggtaa gtgttaatcc gtggcaatcc gcattcctgc gggattcatc tggccccgtc | 660 |
| gcccagtggt gcggaggcct ccccttcagc gcggtagtgt ctgtgggtat tgttattgtc | 720 |
| agcttactgg agcgtgtaca ggaacagaac gaagccgccg agttgatagg gctttgcgtc | 780 |
| ccagagcctc ctgccctccg cctgtattca gagctgcggg ctgcttgttt gttccttggc | 840 |
| ggtggagggt gctagttgag gccagacttc ggggtctcct gggggccgtg ggacgaccag | 900 |
| gggtggccca gcttgacagc tttcagctgg gatctgtgga tcccagcgct caccaatgtc | 960 |
| ggcccacgtg tattcgttca tgccatggcc ggcttcttcc gctgcagtct ctggcccgag | 1020 |
| ggctgctgct gcgggaccgc caaggaaaga cgagctgtag gtcggctggt ccagctgcag | 1080 |

```
gcagaaattc tggtagtatc tctgggaata tgaagatgca actgccccca ccttgccttc    1140
gaggatatca tgggccagaa ggcagagtcg ttttgaatac gtggttcatt gagtacccac    1200
tctgggccag ttgatggctg cgaagagagc agaaggggtg ctgctgtagg aaatcaatgg    1260
ctcggaagac cacactgagg aaggtgtgag ttgatactgg aagatctcca ggtttgaggc    1320
atcttcagag gtatatggtg gttttgtgtg tgttgagggt gtggtagcgc agcagctccc    1380
tagggaatta gaaggtttta ttgaacattt accctgtgac aggcactgca ggcattcagc    1440
gcgcagtgtc atcttcattt tacaggtgag gaaaagactc aggttcaagt agatggtcaa    1500
ggccagtact accggaagga ccatctgggg gttcggacac tggtggggtg ggatttgctg    1560
ccccttgcaa attgagagtg tcttggggtc agttttgatt tgctcagctg ttggcattct    1620
ttgggctctg agtgggtgag gtgacccttg acctcctggg atcgcatctg gagagtgcct    1680
agtattctgc cagcttcgga aagggaggga aagcaagcct ggcagaggca cccattccat    1740
tcccagcttg ctccgtagct ggcgattgga agacactctg cgacagtgtt cagtccctgg    1800
gcaggaaagc ctccttccag gattcttcct cacctggggc cgcttcttcc ccaaaaggca    1860
tc                                                                   1862

<210> SEQ ID NO 8
<211> LENGTH: 2363
<212> TYPE: DNA
<213> ORGANISM: Homo sapiens

<400> SEQUENCE: 8
gcttcctgga ggtgcattct aagagcgctc cccataagcc aacactcaag tctcttcgag     60
gtgtgtttcc agggagcctg atctaagatt aaaaacttaa aggccccttt tagaattgtc    120
ttttacagcc caggcaaaga gttctttact tttttagagg tcatgaatcc ctttgacaag    180
gtgatgaaag ccagggaccc tcttctcaga aaaatacaca cgtgcgctta atgtaaaatt    240
ttacatactg ttttaaaggt taaactttac cacccatgaa aagcctcaag tagttctttg    300
tacataatca taagattagc aaccatttac tgagcacttc ctctctataa gaccctgtgc    360
taagtgcttt aacttcataa tgcctttgat catgacataa catggcacgg tagttcctaa    420
tatcttcctt ttagagattt aagggcttgc tcaaagtaac atagctaata attagcagac    480
actggattaa aatcccaatt tgtttgtaaa gcttgtgctc tgaataaatg acaaggaaag    540
agaagggaag gttgaagaag ggaaggttct tgaaggtccc tggtccttga aggtcccttaa   600 accataaaatg tcaagagttg ggatttaaac ccaggtctaa cgccagagct ggcgcccttt    660
agattaaaag tgcagtgtcc atgacaacga agaagttga ttttgtccca cctttgctct    720
ttgcggcttt tcatttgcgt ttgtttccac agcgatttcc aatagatttc tgcgtggcct    780
tgacacagac agctagtgtg aatccccgcc cacagagggg cggcacgttg gttgccgtac    840
aacgtggtgg ttccctgcat ctctgcccac gtcgagagg tgcgtcggct tccgtacaac     900
acggatactc tctctctgac gcaacttcct gtcctgcgca attctatttg accttttgaac    960 tggcaaaggc tttttctctc ctcttccggg gacgttgtct gcaggtatgg atgttgttct    1020
cttttccctg tctttatttc cttaccaatc ggctgccatc cgaggagctg aggaagccta    1080
gagctctcag aagcagtcct ttgagctggt gtaggggtaa ggggcacaac agggaggttg    1140
gtggtgagga agttccttac tttgatcttt ggaaatccct tgttcctggt ggcacctcca    1200
aagccgtgag tagccacagc tcaccacccg ggactttgct gcattccaag tgtagcgttt    1260
```

| | |
|---|---:|
| ggagactaac gagttgtggt ttggcggttt gagtctggaa aatcgccaaa cgttttcata | 1320 |
| ttttacaccc acgttttcac agcacgcctg tacgtgtcct tagtctttgg gagggcaggg | 1380 |
| tccggcgagt tcgggtggtt tcgctatttg gcttctgcgt ccaaggccca tgtcaaggaa | 1440 |
| gagaaaaatg tgttagaagt ttctgtcttg cttttggaga tgcaaacaga ataatggctt | 1500 |
| cataaatcac tcgcactggt tttacgtgtc aagttttggt gtctggtaat tctgttttag | 1560 |
| tttaatttta gtgagaggct tgtgacaaca aatgaggtgg ttacaagggg tggaatggga | 1620 |
| agattaaatt agttcaagta ttgattatgt tttacgttgg gtagttccct taacgaagtt | 1680 |
| gctcgtatgc atatctgtat aaccgatttg ctaaataaca tcacgatgtt tccagaagtg | 1740 |
| ggaagaaagc aggtgccata acccaaagaa acttgtgtaa tatcaaaatt agtattaaag | 1800 |
| ggtatgcctt tacgcaggtg gtgctttagg gcaagacatt gaaccctgat atgtgccagg | 1860 |
| cattgtgttg ggacggatag cccacgtcgt ttaatcctaa tgacagctgt ataaagtaga | 1920 |
| cagaattccc atgttagaga taaggaggct agctccttgc cctttatatt cccagtaaat | 1980 |
| ggcatagcta aggattcgac ttcagagctc acttttgtg ctctttgttt aaagcggtgt | 2040 |
| ttctccaact gggctcgtgg cacttttctg gacaccactc caaacaaaat tagactctga | 2100 |
| gtaaggagcc tggtcatcag aacgttaagg aagtgccacg tttgattacc atcaggaaag | 2160 |
| ctaacattct tggcctcttg tttatcagtc acctttaaat acaagtagtt ttaaaatgtg | 2220 |
| gaataataca tcttaattta agggtgttac atacaaggat atgtatgtga atgaaataga | 2280 |
| ccacatgata ctgttttgag attttattta cttttacaat ggaaagattt gatgttactc | 2340 |
| tattcttaat ttaggcactc aga | 2363 |

<210> SEQ ID NO 9
<211> LENGTH: 1858
<212> TYPE: DNA
<213> ORGANISM: Homo sapiens

<400> SEQUENCE: 9

| | |
|---|---:|
| gtaaagcttg tgctctgaat aaatgacaag gaaagagaag ggaaggttga agaagggaag | 60 |
| gttcttgaag gtccctggtc cttgaaggtc ccttaaccat aaatgtcaag agttgggatt | 120 |
| taaacccagg tctaacgcca gagctggcgc cctttagatt aaaagtgcag tgtccatgac | 180 |
| aacgaaagaa gttgattttg tcccacccttt gctctttgcg gcttttcatt tgcgtttgtt | 240 |
| tccacagcga tttccaatag atttctgcgt ggccttgaca cagacagcta gtgtgaatcc | 300 |
| ccgcccacag aggggcggca cgttggttgc cgtacaacgt ggtggttccc tgcatctctg | 360 |
| cccacgtcgg agaggtgcgt cggcttccgt acaacacgga tactctctct ctgacgcaac | 420 |
| ttcctgtcct gcgcaattct atttgacctt tgaactggca aaggcttttt tcttcctctt | 480 |
| ccggggacgt tgtctgcagg tatggatgtt gttctctttt ccctgtcttt atttccttac | 540 |
| caatcggctg ccatccgagg agctgaggaa gcctagagct tcagaagca gtcctttgag | 600 |
| ctggtgtagg ggtaaggggc acaacaggga ggttggtggt gaggaagttc cttactttga | 660 |
| tcttttggaaa tcccttgttc ctggtggcac ctccaaagcc gtgagtagcc acagctcacc | 720 |
| acccgggact ttgctgcatt ccaagtgtag cgtttggaga ctaacgagtt gtggtttggc | 780 |
| ggtttgagtc tggaaaatcg ccaaacgttt tcatatttta cacccacgtt ttcacagcac | 840 |
| gcctgtacgt gtccttagtc tttgggaggg cagggtccgg cgagtcgggg tggtttcgct | 900 |
| atttggcttc tgcgtccaag gcccatgtca aggaagagaa aaatgtgtta agaagtttctg | 960 |
| tcttgctttt ggagatgcaa acagaataat ggcttcataa atcactcgca ctggttttac | 1020 |

```
gtgtcaagtt ttggtgtctg gtaattctgt tttagtttaa ttttagtgag aggcttgtga    1080
caacaaatga ggtggttaca aggggtggaa tgggaagatt aaattagttc aagtattgat    1140
tatgttttac gttgggtagt tcccttaacg aagttgctcg tatgcatatc tgtataaccg    1200
atttgctaaa taacatcacg atgttccag aagtgggaag aaagcaggtg ccataaccca    1260
aagaaacttg tgtaatatca aaattagtat taaagggtat gcctttacgc aggtggtgct    1320
ttagggcaag acattgaacc ctgatatgtg ccaggcattg tgttgggacg atagcccac    1380 gtcgtttaat cctaatgaca gctgtataaa gtagacagaa ttcccatgtt agagataagg    1440
aggctagctc cttgcccttt atattcccag taaatggcat agctaaggat tcgacttcag    1500
agctcacttt ttgtgctctt tgtttaaagc ggtgtttctc caactgggct cgtggcactt    1560
ttctggacac cactccaaac aaaattagac tctgagtaag gagcctggtc atcagaacgt    1620
taaggaagtg ccacgtttga ttaccatcag gaaagctaac attcttggcc tcttgtttat    1680
cagtcacctt taaatacaag tagttttaaa atgtggaata atacatctta atttaagggt    1740
gttacataca aggatatgta tgtgaatgaa atagaccaca tgatactgtt ttgagatttt    1800
atttactttt acaatggaaa gatttgatgt tactctattc ttaatttagg cactcaga     1858

<210> SEQ ID NO 10
<211> LENGTH: 8450
<212> TYPE: DNA
<213> ORGANISM: Homo sapiens

<400> SEQUENCE: 10
attttgcttg aaaggatagc atcaaggaag tgaaatgaca acccacagaa tgagagataa      60
tttttgcaaa tcatgtatct gataagggac ctgtagtcag aatatgcaaa gaacccttac     120
aattcaataa gacaacccaa tttaaaaaca ggcaaaggat gtgaataggc atttctccaa     180
agatacggaa aaacggccaa taagcacata aaaagatgct caaaatcatt tgccattggg     240
gaaatgcaat caaaaccaca atgaggtatc acttcacgcc cattagggtg ctatagatc      300 agaaagtcag ataacatgtg ttggcaagca catggaaaca ctgaagtcct tacacactgc     360
tggtaggaat gtaaatggt gcagccactg tggaaaacag ttttccaatt tctcaaaatg      420
ttaaacacag ttatcataca cccaagcaat tctactctta ggtatatacc caagagaaat    480
gaaaacatat gtcttcacca gaacttgctg ttcacagcag cattatgcat aatagaccaa     540
aagtggaaac aactcaactg cccatcaact ggtgaatgga taagtaaaat gtgatgtaac     600
cagtcattgg actgtcattc attaataaaa agaacaaggt actgattcat gttctaacat     660
gagtgaatct tgaaaacact atgctaaatt aaagaagcca gtcacaaaag gccgtgtatt     720
gcatgatttt atatatacat gaacttttat atatatataa ttatatatat tatatataat     780
tttatatata taaatttcta tatataaata tataaaatca tatatatgat atatattttt    840
tcatatacat catatatatt tacaaaaatt atatatcata tatcatatga tatatgagat     900
atatatcatg atatatatga tatatgatat atatcatatg agatatatga tatcatgaga     960
tatatgatat catatgatat atatgatata gatatcatat gatatatata taatatatat    1020
atgatagata tattatatat gatagatatg atagatatca tattatatat gatagatatg    1080
atagatatca tattatatat gatagatata gatatcatat tatatgat agatatgata    1140 gatatcatat tatatgat agatatgata gatatcatat tatatgat agatatgata    1200 gatatcatat tatatgat agatatgata gatatcatat tatatgat agatatgata    1260
```

```
gatatcatat tatatatgat agatatgata gatatcatat tatatatgat agatatgata   1320
gatatcatat tatatatgat agatatgata gatatcatat tatatatgat agatatgata   1380
gatatcatat tatatatgat agatatgata gatatcatat tatatatgat agatatgata   1440
gatatcatat tatatatgat atcatatata taccacatac atcatatata catcatatat   1500
acatcatata tatcatacat atatatgaac tttccagaat aggtatatca ataaagacag   1560
gaagtataca agtggttgcc acagcctgag aggagcaggg aatggtgagt gactgctaat   1620
ggatatggca ctttttttgg ggggtgatga aaatgttctg gtcagacaat ggcaattaca   1680
aaactgtata cacacgaaaa accaaagaat cacacacttt aaaagggagg atttagctcg   1740
gcatggtggc atgcgcctgt actcccagtt actcgggagg ctgaagcagg actgcttaga   1800
gcccaggact tcaaggctgc agcgagctat gatcgctcca ctgcactcca acaaggatga   1860
cagtgcgaga cccgttttct aaataataat aataataata ataataaata acccaaggta   1920
cccagttcac atgcaaaacc actggtaaac ataaattatc tccaagtaat ctagaaagaa   1980
aatgagcaca taagacgtct tctaaaaaca cacatatatt tctttacatg ttacatttaa   2040
cgtaaaaatc agctatgcag aagttacatg aacattttat gttggaaagg taaatgacta   2100
ttattaatac agaatggtta agtacattta tgtttttatg tacaaacgca taaaaggaaa   2160
agcatcctta aaataaacac catcaatggc tcctcggtgg tcacaaaaca aaatcctcac   2220
acctttgtct tccttcacaa ttgagcttta tccaccttt caggcttatc tcccattatt   2280
acctgacaca aacttgggtg ggccagagtt tccactgacc atcccccgac tattcatcca   2340
acactatgtt cactgcctcc cattcctgac catttgcctt ttgtcttcaa ctaattctgg   2400
ggacgttttg tccaaataaa tgatccatat tcttgaaggc tggaatcaag tcctattaca   2460
aatatatttt ctcaccctct ccagagcata gcaacccagc atctactggc ctctcacagc   2520
tctaaccatc cacaaccccta agctggcttc tcatcaaacg ggtacttttc accacccaaa   2580
ttcaattaat tcactcttac aataatgaag aatagtcgcc tacagcctac cttttccagc   2640
cttgattcaa tcatttatca attttatctt caaagtccct cacttcaggg agatgatata   2700
tcagctttca cccagagtcc taagaaaaac agcactcttg ccaatgacat agtgccacct   2760
agtggcaaca taaggtaaat cacagtggca gtagaaggat ctccacacta cttttacagg   2820
aatgcactgc aggtaaaaaa taagaagcta cagtactgtt tggcaggaca atttgtttca   2880
tacgtgcata ctatcgccct gactaaatta actcgcaagt cttacaggta ttatttgttt   2940
tcagttccat gcacagatta gccatttagt acttactaaa tcaaactcaa tttctgaagt   3000
gtcttacacc aatatattca tgcacatatg gttaaaattt tccttgagga tctatcatgt   3060
gagagtgtgg cttattataa caagtaaaca gaacaaataa atacaaaatg aaaagaaatc   3120
gtatgattta ctcgcatata agggagcttg ttgtggatta agtttcatga cccaggacac   3180
tgaaacagaa atggaataaa tgagaataaa attaaaagtt gtcatcaaaa atatagaagc   3240
catctaaaga cctaggtgtc aagcatagct ctatgagtac aatcccgtgc ctgagattac   3300
catatgccca gctgtatgct atacactaag agatttagga aggaagcggg gtcagggatt   3360
gaccccagac tccatctttt caagtgggga agaaagatct tccgattgaa aaataaaggc   3420
aaaaaaggct tcaccgtcac agaagtttca acaaccaaca ggatatttaa aacagttatc   3480
aaagcaaaac cattgtatgt tcacttacat ttttacatag tccctcaaac tcacaaaatg   3540
ctgtttactc agggacttct tccggtctta ctagggagcc tggaaagtga cgggaggatt   3600
gcaagggacc actagaaccc tcttcctcaa ttcccctct ctgagaaggg aggctacagc   3660
```

-continued

```
ttgcctctct aaccactaaa aggcatgacc ctcctcaaag ttaatagccg gattccctga    3720
tagatatttt cactaaatga attctcataa aactctcact aagatttaga gaaggcttcc    3780
agggttgaat tcctgaacat taagaacagc atgttttta aaagtttaac ttggtgattg     3840
gaccaggact tcatctaggc tatgaatgct cagaatggta ggtcctttac caaacagctt    3900
gagtttgtgt ataaagtgat ctcatcctct taagagtcag agaaacagaa ccaagcgact    3960
tcactataat ttgatctgag gaagtttctt actcacaata ggtaaatgaa ggcacatact    4020
aaccagcaat ataaacaaca atatcaagtg tcattcacac atgcaaaaaa cagacaaaat    4080
cccaaactct gtgttctaac aaatcgcaaa aacctcacta acaataaatt gaaatgacca    4140
aatgtttgga ctgaaaagca atgccttggt agcctagcca tgcctaactc aaataacaga    4200
accatctcga tgttaaaatc ctcacagatc aagctgtgta tgtctcgggt caagacttcg    4260
ccaaaaagca gtgagcacac acttaagagg gaaaaaatct acctcagcct cctaaatgca    4320
atcatctcta cacgagttgc aggccccaag cttcaacgtg ttctgctgga caacgcagta    4380
gaaagctgac aagcaggtgg ccttcccaca ctgactgaac cacctccatg cccatgtcca    4440
ttcattttct tgcccacccc atgtgctata acagacctcc tggctcaggg cactcttcc     4500 ttcctgactg ccttcactta atgactttgt acttttaggt gcaaaaatta tctgcagaaa    4560
tccacactga aaaccaagct tgagaaaggc agcaataacc aacatttta caagaagaac     4620 aaggtcaata tcaagcccat cagattcaaa tagcaagcat ggatgaaaat gaaagattga    4680
aaggcttgag tgccttctta atgtattaaa tatccattta atttacaatt aagctcactg    4740
tgctcactgg ccttttaatc agctttccag gtcctgctca gacttgccta ggacatggga    4800
atgaaagaac ctatacattt atggaccaat ctaccttaac taacttgtca agtgttcctg    4860
catcaagcag aagaaacatc agtgaaactg atacaggaat taaccccttg ttaatccata    4920
aaacttaaag gagcgggatc caatcttctg gcttccctgg gccacgctgg aagaagaatt    4980
gtcttgcgcc acacataaaa tacacgaaca ctaataatag ctgctaagct ttaaaaaaat    5040
tgcaaaaaag gaaaatctca taattttttg tttgttgtga ggtggagcct cactctgtca    5100
cccaggccgg agtgcagtgg caccatcttg gctcactgca acctctgcct cctgggttca    5160
agccattctc ctgcctcagc ctcccgagta gctgggatga taggcgtgtg ccaccatgcc    5220
cagctaattt tcgtattttt agtagagacg gggtttcacc atgttggcca ggctggtctc    5280
aaactcctga cctcaggtga tccacccacc tcggcctccc aaagtgctgg gattacaggt    5340
gtgagccacc gtgcccggcc aatgttttaa gaacgtttac gaatttgtat tgggccacat    5400
tcaaagcctt cacaggctgc atgcagcctg caggccgcgg ttggacaagc ttggattaga    5460
gaaatctaca gagacaaact agtgacttag tagccctctg atagctcatg atttgcaaga    5520
aacttaggat gactatgtgt aaagaccaca acatcaatt taactgaatg gttcccgcca     5580
cactggaatg aggaagctga gcaaactcag aggactctaa gaaagggctg atgtcatctg    5640
aactgttcgg aattataaac tcctctaaac atgtttcaaa gccagaactt gtaggagttg    5700
ttctgataca cggattaaaa gagggatgac aaagtgtctg tccccacac tggtcaaagg      5760 gacaggtcat tgttatgctg gcaatgcagg ctgctgaaaa gaatgtatct gtcaaaagta    5820
atcaaagtaa tgaccccaga aggctccaga aacagactgg taaattcagg ttgctttcag    5880
acttccacaa tgctggcaca caaggggaaa gacaaaacta acatttacag agcattatat    5940
ttgatattac atttaatccc cattaaaaag atactatttc ccgtttcact agtgaaaaag    6000
```

```
ttgatctttc aaaggttaaa ttatttaaca ccaaggtcaa agggtaagtt ggagagacca      6060
gattcaaacc cagtctgaca ttaaaacatg tgttttcccc ccacatcgtc tcctgctaat      6120
aacctcaaat ctaaaaactg acttgcccta caccttgagc cccatcctac aaactctccc      6180
tgacgttatt aattcagctg tcactgtgca cctacaacgt gccagacacc atactcctca      6240
acactctgta ggcacagaag gaacagataa aaatccctac cttcatagat attattctag      6300
gggtaacaca ggtaaataaa acattaaaat agttttcaca tagtagcaaa ttccatatag      6360
caaaataaaa cagaagaagg aatagcaaat gagggagatg ccctcttaaa catggtgctg      6420
agggaaggcc tccctgagaa agatatcatt taccccaaaa ataaaaaagc aagtaataga      6480
aaaaacaggt aaaaggtgtt ctagacactt aaacctgcca cattgagaac tcagggttct      6540
gatgcaaaac ctcgctgcat agaatgcatt aacttatttt tatacattta aacaaacaaa      6600
ctctacttaa gaactgtgtt ctaaaggaag gagcatatta caggaaggca attttggtc       6660
agagtagaca cacttaaaaa ctaaacctat tgaaagacca agaacaactg aaagtctttg      6720
ctttgtcaga ttttgacca aaaggaaaat taaagaaaca caccgtgccc atccaatgat       6780
ttcaccaagg aattttaaga gagaaaatcc tacttcttcc tcacccagta gccagtgaaa      6840
tgactgagca aattcacaag ttcactgggg ctgctttcat gtaacacagg gacaacacat      6900
gacagacaca gtggaaccct acaggttgcc tagtatttga aagactgtga agaggaggag      6960
atgtcaaaat tcaaagtctt aaatgatgta gtttttaagta tgttcagcaa tttcaccact      7020
cagtagtaaa gccagctaca gttgaaagca atcagaaatt tgagggtgt gaaataagca       7080
gaagcacaga agttaaggat ttgtattctt cccacatttt ccactttatt ttatactgct      7140
gagaaaaaac aaatttaata gttttctgct gtataagaga gacacattca ctttatgtca     7200
cagtaagagt cactcaattt taatacaact atctcaatgt ataaattaac attctccccc      7260
ctgcccacac atagtaagtc tcttatgatg ttgctgatta gagaagcaaa agttgccgct      7320
acaattctct tcctgcattt taatataaac aatcatcagt cttttcttca tagagtgcag      7380
tgtgggcact atcatcagaa tgtaccagca ctgggtgtgc aaagtttaca aagattagca      7440
agagcaaaag tgttgagatt tttgaaattc atgctgctgc aaagaagtat gtaaaaactc      7500
actcaccata gaggaccaca cagaaactca ggcatgaagt tatatggctg tgtgagtggt      7560
ttgggagaag gaacggaaag cacttccacc aacctatatg cctgagcaaa ttaatgcaaa     7620
acctcagaag ctacaaaaaa gtttatctac ctaaattaaa attggtgtcc acagcagtag      7680
ccagcaaaat gcctgcgaag cgcaaagtgg taaatatttt agggtctgta ggtcatatgg      7740
tctctgttaa acaatatgta aatgaatggg tgtggctgtg ttccaataaa acttcattta     7800
taaaagagg cagcatggta catccagtca gcaagctata atgtaccaac ccccggtcta      7860
acactaacca aatacctctt aataagccaa agaaactgtg tcctcttagg ccggaagcgg     7920
tggctcacac ctataatccc agcattttgg gaggccgagg cggggagatc acctgaggtc      7980
aggagtttga gaccatcctg gccaacatgg tgaaacccta tttctactaa aaatacaaaa     8040
attagccagg cgtgctggcg ggcgcctgta atgccaacta ctgggaggc tgaagcacga      8100
gaatcgcttg aacccaggag gcagaggttg cagcgagcct agatcacgcc attgcactcc     8160
agcctgggca acaagagaga aactccgtct caaaaaaaaa aaggaaata aaagtataca      8220
aagtgaaaac aaagaaatta aactgccctt atttgccagt gacattactg tctatgcaca     8280
aaattccaaa aatctacaaa aaagcttcta gtactaaaaa tgagtttagc aaggttgtag     8340
aatccaaggt cagcatataa cataaaatca ccttcctata tactagcaat caccaactgg     8400
```

```
                                   aaattgagaa gtatcattca caacagtacc acaaacatga aataaatgtg      8450

<210> SEQ ID NO 11
<211> LENGTH: 8420
<212> TYPE: DNA
<213> ORGANISM: Homo sapiens

<400> SEQUENCE: 11
tcttagtatg gtaaacctt tgaagtagat tcaaatgaga atgggaagag agaaaaggga         60
gagaagcaac ataagaaatc tcttttaagg aatttttatat agagagaaac agaggaatca      120
gttgatagtt ggaaattatt ttaaagaaaa tgggttattt taaagaaaaa aggtattaca       180
acatgtttgc actattgtgg gaataatcaa gttgagacag aaaattattt tttaaggaag       240
agtctaattg ctgaagtgaa agagaatgaa tgagaccctg tgcataagtg tgatcagata       300
ggagcatgta cagctcaagt aagaacagga agaaagagac aataaacatg tacagatagg       360
atgggctggt cgatgtggtg gtgaaaagac atgcgagtta ttactgatta cttctatttc      420
cccagtgaaa taggaagcca ggttcataaa ccaaaatgaa gaggagcgag gcagtattgg       480
aagttcagga aaagtaatag gtgtaaaaat atgtaaagta gaattaccag ggagtatgaa       540
gatacatttc caattaagga tgaagaattt aaagtgaggc cagccaatac ccctgctttg       600
cttcagctac atcagctgca taggttcagg cacagaatac atggaacatt gtatttaaat      660
agggcctgga ttttacaaaa gtaacacaat gaagaagaga gatgcaaggc tatttgaggg      720
tgtttgtggg agagattgta aaatattagc taagtaagaa ggggactgca aattttagtg      780
gtataaagga atgaggaaaa gtgtaaatac agtggggtca aagaatgttt ggagccaagg      840
cactagaggc aattagctga aaatgtaggt gattattggt gagtgacatg gtttaaatga      900
aaagtataga agggtacaat tatccatcat gaaaagttct agggtacaac taagatctga      960
gtagctgaag tagaatgaaa gtagaatgga cctttccata tccagccagg ttcagtgaca     1020
gaaggttagg aaacaaatta taaaccactt gagagaacat atccctaag ttgttttgc       1080 tattttcctt tcagcatata tttgttggaa tgccaactat gttcagttca attaatatgg     1140
gcttcttaaa taagggctcc agcactggat aatcctgcca tttattttga tacattccat     1200
cctgctgctc agatctattg gcatctacag gatgtctttt gagaagatgg gcattcacat     1260
ccctatgtcc tagcaaattt ccaactcaga aaaccacatt aggcttctct atatatcttc     1320
caactatttc aatggaaaat acaattctct gatttcttcc tatgatattt atcaaagaga     1380
atggtgcctg ccagttctag ggtgggggaa ctcaatacaa atcaccaacc tttagatgac     1440
accctgtctt caaagtgctt tcaaagtctg gcagaaaaaa agtacccagt ggctataaga     1500
ccacccagga gttcagtcat gcattctaag tagcagatca ctggaatgta attggctagt     1560
gagttcattt tactcttctc ttccttggtca catgttaccg cccttgtacc ctgcacgttc     1620
tctttcccag acttacaaag catgttctct gaattcgtt ctcttttaa attcacacag       1680 tcttaatgat tcttctttca caagagtctt tcactcttac aattcagttc aagtcatcca     1740
catgcttatt atgagcaagg gtctgggact taggggaaaa gggaataaaa agatgaatga     1800
aatgtgatcc ctgcagtcca agagcttgct gtgaaaaagg aagtttggct tacattgcct     1860
ccctaatccc ttggctaggc cagaacagaa tattgtctaa aacctcctca cgtcagcagt     1920
cctctggggt ggtgactgga agtagaattt aaacaaaaat ataattgaca cataataatt     1980
gtgcatactt ataggtaca atctgatgtt tcgatatgtg tttaaatggg tgcattgtgt       2040
```

```
aatgatcaaa ttgaggtaat ttatccacca ccttgaagag agattttcca atattctcat    2100
tgcgaagaag caggaatttt tagcagacaa ctgagatgct tcttgttcac actaagtcat    2160
tctgacgatg gatttacata acttgttgtt tttttgtgt gtgtgttttt gagacagagt     2220
cttactttgt cgactaggct gaagtgcagt ggcacaatct cggctcactg caacctccac    2280
ctcccgggtt caaacgattc tcctgcctca gcctcctgag tagctgggat tacaggtgca    2340
tgcaactagg cctggctaat ttttatattt ttaatacaga tgggatttca ccatgttggc    2400
cctgctggtg tcaaattcgt ggcctcaagt gatctaccag ctgcggcctc ccaaagtgca    2460
gggattacag gtgtgagaca ccaagcctgg tacatttaca tttcttatct ggatcttttcc   2520 tttagtaagt gctaaggaat cctacttccc ccaatatttt ttcctatttc aatgttttag    2580
catgtatcat gttactactt tgcagacatt tgattttccc ctttgtttac tgtaaagtat    2640
atttttatag cctttgtaat agaagtattc taaaatctgc ctgcaaccta tctttctgac    2700
tctgcatttt agggaataat tctctgttgt ggaatgaaaa aaaaaacaga gcctgtggag    2760
tcagagatct catttcaaat tatagttatc cctaggaata aatctgagtg acaggtagta    2820
tagtataata ataagtataa agctatggtt aaggaaaact caacaacctt atctgtaaat    2880
tgggatgaca acagcctacg tcaaaaaaat gtgaaggtaa atgagataat gtaaggctga    2940
tacttagtaa gcaatttaaa aacacccaaa aaactattgc catgattact ctacttactc    3000
tatttctcta tgctccaggc aaatgaacta ctaatgaccc aggggtcctt ccccattctc    3060
ttcttcacaa ggaaatattc tctctctgtg tgctgtttat taaatctac tgccccttt      3120 agaagccttt ccagatcatc ccatggccaa gaacgatcgc tgcttcctct tctttacata    3180
cagatgtttt tctcctgctt gacaattatt tttgtgcaat tatttttcctt ttgattgtgt   3240 ttttaatgtc cccccaccc cacaattttc cagactgttt gctccacgag agaggagacc     3300
atcatctctg tgctcaccgt tgtatgacca gtatcctgag gagtggctgt tacataatta    3360
catcaggcac tcaataaaaa tttgatgaat aaacactgga ttttaaggca ggtatcatat    3420
cttacatagc atatcatatc ttacatttta tgtccctcac ataaatacca cagagtgaag    3480
tatatgacag ataaggtcat ttctcttgat aagtacatag tccagtctga aacagatatg    3540
ccaaaaaaaa acaaaactgg agtaaacaag atgaattgtt ttaatagagg cactgtatta    3600
gtttcctagg actgccagaa caaatcacct caaacttagt ggctgaaaac aacaaaaatt    3660
tattgtctca cagttataga tgttagaagt ataaaattaa ggtgtcagtg ggattggttc    3720
cttctggggg ctgtggaaga gaatctgtcc caagccttca cactgtaaag tacagtactg    3780
gagggatagg acttcaactt gctctatctc agatagagag gagccatttg ttgtgaattg    3840
agaagagggg tatgttgaat ccataataag cacataaaaa cttggctggt tcataggaga    3900
agtaacatgt ttccagctct agtaaaaaac aaattgaagt ggcctataaa aaggtacaga    3960
gtacgacaga atgaaaaata aatgaacaag aatacagaga ggatgtggta aattatcatg    4020
tttccctaat atgttattgg acactaaatg gtattagaat tatttatcaa taataattct    4080
aaactgttgc aattgaaaga atatattaag tggtgttata tgagaagtgc cagggcattc    4140
tcatttctgt ccaatgggag aaacattttc gtttgagacc tccgtgaata atacagtctt    4200
ttagttagga gagctgcatt ttgagtggtg caggcagaat ggcgatctct caccacaca    4260 aacactaaga tagagagaga cagagacaga gacagagaca gcagagagag acagagaaag    4320
gaagtacagg tactcagata gagataagcc atttcttgac attaagaaat aaagtagaat    4380
ccattggagg gaaataaaac tgcctcagga acagagttaa ttcacataca catgcaggta    4440
```

```
aacacacact gcttgatact tactgtggac tttgaaaatt atgaatgtgt gtgtgtgtgt    4500
gtgtgtacat tcagccctcc atatccatgg attttgcatt cacagattca accaaccatg    4560
aattaaaaac atttggaaat aacaaacatt aaaatataac aatacaacaa taaaaataat    4620
acaaataaaa aatatagtgt aacaactgtt tacatagcat gtatgttgta ttaagtagta    4680
taaatctaga gattacttaa tgtataccag aggatgcata ggctatatgc aaatactatg    4740
ccactttaaa ctgataagaa cagatactaa acttcatctt agccaaaagt cagagaaaca    4800
atataactat gccattttac ataagggact tgagctgagc atcctcagat ttcagtatct    4860
ttggagttcc tggaaacaat tccttgtttt atatatatat atgtgtgtgt atatatatat    4920
atatatatac acacatatat atatatatat atatgataga gctactgagt gacaggtgat    4980
attataccat accacttgtc actcagtagc tgtatatgca tatgtatata tatcatata     5040 catatatgtg tgtatgtgta tgtgtgtgtg tgtgtgtgtg tgtgtatg ctgtctttcc      5100 tcggtatcac agggaattgg agatatatat attcttttca gtacaaaaaa aattgaacac    5160
agatgggtat ggtaccagaa cagaaggtaa agacacatga aaaaaatttg caacaacatg    5220
aatggaactg gagatcatta tttgaggaga ataatccag gcacagaaaa acaagcattt     5280
tattatttta ggtgaaagac aaacatttta ttttaggtga ataatccag gcacagaaag     5340 acaaacattg catgttctca tttatttgtg ggatgtaaaa atcaaaacaa tagaacgtat    5400
ggaggtagac agcagaagga tagttaccaa aggctgcaaa gggtagtgta ggctttgagg    5460
gtgaggtggg gatggttatt gggtacaaaa aatagttaga aagaataaat aatatctagt    5520
atttaatagc acaacaggtt gactatagtc aaaataacat aattgtacaa tttaaatatg    5580
aaattaaata tatatacaag actagaacac caagttgaat gactccagct tgcgaaaccc    5640
acattgatca ccatgcttgc cccaagggaa gctgtacaat gtctggctcg tccagaaccc    5700
catcatttat cactagcaat ctattgtcca taatcatgtt taaattaata gcattttaaa    5760
ggtacaaata tttttttaaaa aacaaataat tatttaattc gccttttaaa agcttttttaa   5820 aaacgttttt aaaaacttt tttaaagtcct gaggactatt tctttaaag tgctcagtta     5880 cagagctcca tatattgggc tatgatagcc ttacctgatt cttgccaaga atctagtgcc    5940
cagaaaatgc aaatacaaag taagcaactg aaaaataaac aaataagttg gaggtatgct    6000
acctgttgaa atatgaccta gcgcaaacac ctatgccact tgcttatgaa atcatatagg    6060
ttttcggtgt gcagttttga ctgaatgagg gagtttacgc tggaccacaa gggggcccct    6120
ctgtcaataa cgtactccat ttgtgtatta agtcaaaaat gaaatggaag agaaaagaaa    6180
catcgatgac cccaagtctc tttaattgaa tggaggtaaa agggaaacaa cgaatgagaa    6240
aagtactctg ccctttttaag aatcttgcat tcacattcct gatgaagtta tttttcctcc    6300
tctcactgat tcccatttca ctctattaca tagcaccgtg ttccccagga gctcctgaat    6360
gaaggacatc actcagctgt gttaagtatc tggaacaata aatatactag tttcaatgtc    6420
taggctatgg gtattccttt ttactgaagg tatgacatat agctgcccag gcctgactaa    6480
attaatagta ataataatta ataatggcaa attttattc tattaagtta cttggcttga     6540
cttgtagaaa tagcaacatt catctgaaat gcccctcct acacttatgt ctaaggacaa      6600
atcccacata caccacagat aacttcattt tacatgtttt attctgttac caaactaaat    6660
ttttatcata tagtctgttg ctcactgaac tcttcagtaa ttctcaacat accatgtaaa    6720
gcattaagca cagttccaac acagagcaaa tgagcaataa ctgttagtta ttataacatt    6780
```

```
attatgtgtt ttcagtgcat taaaccactg gtctgatacc tagcccaaca ttctattaaa    6840
ccacataatc cagttgaata atatatgata atataataaa atggcgataa gtgctaaata    6900
tccagataga aacacagatg gaatcagaca gctttcccaa gaaatagaga aaatagtaga    6960
taggcgatct aggcctaagc actctaagca gaagctaagt tatcacagga tatcttggca    7020
atctgtggca cgtgaaccct tttcttctgg agtctggaac tatgttgcaa ctctcacttt    7080
ctccctatct agagactcag tttgttccct tgtgattatc agcagttgag aaatccttag    7140
accttctgaa aggactactt tttaaattta tatatataat atttaaaata catatcttta    7200
tatataatat atatttaaat atataatatt taaattaata tatatttaaa tataataaat    7260
ttaaattaat atatatttaa ataaataaat ttatatttaa atatataata attaaaatat    7320 attttaatg aacagagagt aaaggattat tttgaagaga aactcctggt tcccacttaa     7380
aatcctttct tgtttccaag ttttcaaat ggagccctct ttaccagctt gcccctcag     7440 agataagctg ttccctact tattcagatc tgagatctga aaacattcct ttcctgtga     7500 gttcagctag gacaaagatg gagcttttg ataaaattg gcaaacacat tttttaaaga     7560
tgaaaatttt taaaaattga aaaaaaaaca tttatagaaa gagacttcta atccaaattt    7620
aacttctcaa actatgtttt gaccggctag cataatgttt cagtctttct ggagaatgcc    7680
ccttgaaact gttttcttct acacaacttc ctccttttcct ttgactttcc tgctctggaa   7740
gggaagaaca ggaagaggac agatcaaatt actcaagagg aaggacaaga aataaggaac    7800
caaattatca acaattggag aaagaaagct gatgtcagta tcatttcata tatgattatg    7860
tcagagtcag gtggataagc caatcctgtt gaatagcata cttttcctgc tactcctgaa    7920
gggtaaagag gtcttctct acaaagccg tcctagctag taatcttaca ggtgcaaaaa      7980
gcttgttttc atgttatttc ttagtaactc aaaataccct caaagttata catattatga    8040
aagtactaca gtcacagtgc tgagaaaagg agtaaataag acaatgtata taaaaacact    8100
tggctcagcc cctggctctg tggttgataa atattaagtt agtattcatt attattataa    8160
tttccaaaga gtccattaaa agatatagaa gaagggaggc agcaataaca ctaagagaaa    8220
attccattat ctccaactat ttatcctcta gcccaaaata attgccatta gaaagagcaa    8280
ctttaacaaa aattttaagt tgcaatagat gttcaacttt aaatccatcc cagaaaaatt    8340
tctaaccaaa ggagcataga agatttgatc ttatttcta agtagtatag acttaattgt    8400
gagaacaaaa taaaaacttg                                                8420

<210> SEQ ID NO 12
<211> LENGTH: 8475
<212> TYPE: DNA
<213> ORGANISM: Homo sapiens

<400> SEQUENCE: 12
gcataacttg taagaaatgg agtgaggtct cagttcaaac tggcttctgt atgacttcaa      60
agccaaagtc agcaacttag aaggcaaaaa ttataattta gttggcaaat acgagaaaag    120
gtcagaaaca catgaaatga agctcaatag gaacacttac agggtagcag ggtagtagcc    180
tagggaaaaa agtcagacac taaaattgtt taaataggta agttcaaggg acaggtaaag    240
accttagtgg gtaagaagcc aatcagcaga cgaactgcaa gcaagcactg tctctctttc    300
ccttctgtct cctcttgtag taactgacca caattaaggc tgcctagggg aataatgaag    360
taatcctcct attatcagca atggtctgat ccagtgccag gcaccacaga caacttggtg    420
ttcagagaag atccttcaag atgaacaaag ggtcaaaata aaaaattcta gaagagagaa    480
```

```
gactgatcac aatttaatgt aaggcttgga aggaactgat ctctaccttc cttaacatct      540
caagaacttc ctcagattca ttggatgttg agtgtgtgtg agtctagtag aaaaatgaat      600
ttttgtttct taacttggat atgtgattag gatgttaata attaagtctg ggctaatatt      660
gaaggtatct tatgatgggc ttcttaaagc attgatcaca aagactgcat gttcataaac      720
tgagctgcac ttgttaggat tctagatgtt tgaaatttct tgtgttattt ggtctcaga       780 tttctagaca aattttctca aattcctatt tcacttttg acatatcatg agtgactcaa       840
atgtttgccc ttgagtcgga aaacacccag cattaggaat aggcacataa acataatact      900
tcaagcttca gatttaagct caattataaa gtgtttaaag gctgtgctga tagttcttct      960
gagtagaatt cctacaacta tgggtttgtc tataataaaa tgttcactct atattgaacg     1020
ccttatttaa aactcgaaat gtgtaagtag taataaagaa aatatgtcct cctgtaacca     1080
aagctaggac cgattacatg ttcacttgac tgacagatac aatcacctat attaggagca     1140
atcagcactt cctacaaac taacaacttg agatgtagtg ttcccattgg ctatgaagat      1200 tttcttatt tactcagaat agtctgtagg atctgccagc tgcccctgat tataccagct       1260
gcacccaatg atcacagtga acattatttt acattctaaa taactggtgc aaggtgagcc     1320
atggttttct gagtttccta tcacctttgt gtttcaggtc ctcaaatgtt aatttgtaaa     1380
gctgctgttt caggcaaaac taacaaaatt agcatctaat caataaccat actatgtcca     1440
cccatatcct ataacacaga agtaggggaa gagtgagaaa ggtggaagtg agaaatagaa     1500
ggcccaaaaa gaaagtttta tcacaggaat atctagatgt cttctgggat tgtctgttaa     1560
agagctgtga cactcatata aatgcagaat tactctcttt cttccttgtt ggttagaagg     1620
ccaagggtgc catggtaata ctaccaaaca tatatcaaag cttggcagga aaaatggtac     1680
cttcagaaat tttataatct gatatcaaat aggtcaagaa atataataaa actagtttct     1740
ttggtttcct tagaaacctg gaaaacttta aattagaaac ttagaaagct ttaaatcaga     1800 cttttgtagtt aaaaaaggaa attttagttc cttccagcat tagaattccg tgattctctg    1860
actctgagcc tggattaaat ctagcccagc tgagtggaaa cttaagtaac tagctggttg     1920
cctttagtga tcttccactt tatggctgct tccgcctaag aagttcatca tcgtgactta     1980 cttttctttgg ggcaaagtcg tgactaactt tctttggggc aaagttggaa agcagaggtc    2040
aaagtcaatc agaaatggga caaactcact tcctactgcc tggtgaaggg gccattttca     2100 gtagccccctt ttcaagatta gtttcattca agatttgata agctgtttg actttactat     2160 agatcttatt atccatgtca gttaagttta tgcttccact aaatctatct gaattcaaaa     2220
ggtaaaaagc taatgctcag tcttatcaga tttatcttat ttattaatag aatgtggatt     2280
tttttaagca tataacaata atagtaatga taggaccata aatgtggatg gctctttaca     2340
agtcactaac attacataaa ttcctcaaca acacactctg aggccataac aaacttttag     2400
aaataacaca attggctacg gaactccagc catctagctt catgggctcc cactttaatt     2460
tcaaaacaac agaactgtgc acattcattt acatgattag ggcagagctt aactgtatct     2520
catgtagcac ctacatcatt cttcagacaa acttattgcc ttttacagac aagaaaactg     2580
gggctcaaaa aaggacttgc ttataactgg ctaataaaga ggaactctgg gttcaaagtg     2640
agtccaattc tttcttccac ccacagcttc tgctaaagtc attacagaaa tgcatagagc     2700
agttcttcca cgttattgct taggtttcta aagagcagtg acctaataca acatgctcta     2760
taatttatta ctgatttaac tatttcacta aggattcact tttaactttt aacttgtaaa     2820
```

```
tatgtctaat aaacaccact gaaatagcaa cctctttctt catggccttg tggttgtaaa    2880
gcaagctagt aatatatgtc tgtggatttg tgctaataaa gttctataca cctcattaat    2940
tccacaaatc ctactgggta tttcttatct gccagatcct acgctaggta ctggatacac    3000
agtactgaac aaaatgggta caaatgagcc tcacagagct tgtttcattg aaaagcagag    3060
agatacacac taatcaacaa attaatagta acacactacg atgtgttttg aaggaaaatt    3120
agagcatcaa agagacggtg ttagcaggtg gaggggagc cttttagatg gagaatgaga     3180
atgcctccct aaagacatgg gaataaattg agatcacaaa aaatgagaaa tagccagcct    3240
tgagaagagc agaaggaaga acattcaaag gaaagaaag tgcatactgg aaagcctgaa     3300
cactagagtt tggtgtatgt aaggagctga gcaatggtca cttgtgtgat aagatgtgtg    3360 gatgtgggt gggggcagg ggtgagtccc acgcagctct taagtgtgtc ctcagactcc      3420
tgtggtttcc atcagccaca acctgaataa ctgtgtggta atccaaaaat gattacagat    3480
taaacatata aaatatcat tacacccata gtacctaagc caaggacaca gtattctatc     3540
ttttcaatga agatctgcat gaagtaaaat tattatatat aatttttaggt attgatatag   3600 atacatcagt ggatagatat agatatgtgt ctctggtata gaaaaaagtt ttaaagggat    3660
attaaaagtt cttatcttgc agggttgaag attgtggcaa ctttcatttc ttttaatttt   3720
taagaaaaaa gtggtattat gggggattag catgtttgtg ggtatatgta tattttaat    3780 taaaaataa acaacaaat gaaacgtttt ttcttctatg aaagcctaat aagaagaaat     3840
ttcagctgtt ttaacttagg gagctaaaaa catcaaatcc aagaatgttc tctggaactg   3900
agctcaatac atttttattt gagtaagaat tggatacatt tccatcccct tggggctcca   3960
gtctgtcaat attttacttt tcagcgataa aaagacacat gtagataatc acagtgacct   4020
cagtaacttt ccttctctta tttaagttta ttttatttct atcgtagttt tccctgttaa    4080 agatttttc ttttgctta catatataat tttagagaat aacaatgcac acacaaaaaa      4140
ttcctcttgt tctgctagac ctggactttt tctctaatat atatctccat tttttgtctt   4200
ttttcagacg tattttggaa gcaaaggaga gaattgctat atagctgact tcctcttctc    4260
atcaacagtg ttttaacagt ttttaagcaa aagtcagctt tgtttatcta agattttttt    4320
tgctggcatt taacctaccc ctgcctcccc tttcccaagt ccacttcagc caacctctca    4380
ttcgacaggt accaccctct aacataactg aaataatgtc taccattact ggatcttgct    4440
agcaaagaat ctcaaatttt cccacttggt tgtaaattat tttgtaatct ctagtgttta    4500
aggtgcgctt gtcctatcta atccctccc tggcaggaca ccttacagaa cctaccctt     4560 acactagtca ttaagcacca tcagggacgg atggctgtgt cactggtctg tttggtattc    4620
cctactgatc ctaccatgtg gtgattatct atgacttccc taatccctgg ctgccttagc    4680
tgggactggc tgacatgctt ctcaggttgc cgctggcttt acagtccttt actgcccatg    4740
ccactttgga gataggcagg gctagtactt ttctatataa gcccccaaac ttgactttgt    4800
gtttcacagt aggtgaaaaa gttgggtctc ttttctttta cttttctttc cacaagatga    4860
taaagctagg ggaagcctgt ggacatggtt tatttctgca actgcaatga ttgattggtg    4920
cttcctgctg cttacttcct aaactttgtg ctcagtgtca gatccctagc agtttctatc    4980
ccctgctctg ctaaaaaaga atggatgttg actctcaggc cctagttctt tttaattaaa    5040 ttgtatttt gttatcatta ttattattat tattttgaga tggggtctta ctctgtcgcc     5100
caggctgaag tgcagtggtg caatcacagc tcactgtttt agcctcctga gtagctggga    5160
ctacaagcgt catgccacca tgcttctttt taatttttta aaatggtttt ctgccttcaa    5220
```

```
ttctaagcac ttctcaattg taaccaagag ataatacttt ttatgaattc ttaaagttat    5280
caacagatac tcaaagtttt agcaaagtct aaatgatatt aagcttgtcc ttattgccca    5340
agtgacttca atgactattt gttaattgca accaagggtc atttttttaaa tgaatatata   5400 ttattattat atatataata ttaaggtcct caaataccta aaagtttagc aaaatctaaa    5460
taatattgtg catattcttt tattactgta ttagtccgtt ttcatgttgc tgataaagac    5520
atacccaaga ctgggcaatt tacaaaagaa agaggttcac tggactcaca gttccacgtg    5580
gctggggagg cctcacaatc acggcagctt acgggattgt tgagaaatga cacttctcaa    5640
gctgggccta aactatctct gtggtagttg ttctgattca agtattgaat tggttttttt    5700 tgttttttt gagatggagt ttcgttcttg ttgcccaggc tggagtgcaa tggcacgatc     5760
tcagctcacc gcaacctctg cctcccgggt tcaagtgatt ctcctgcttc agcctcccaa    5820
gtagctggga ctacaggcat gagccaccac acccagctaa ttttgtattt ttagtagaga    5880
catggtttct ccatgttggt caggctggtc tcaaactccc aacctcaggt gatccacctg    5940
ccttggcctc ctaaagtgct gggattacag gcataagcca ccgtgccggg ctggagcatt    6000
ggtatataaa agctgcctag gtaactctaa cctttggccc catacatctg aaggatacct    6060
acaatgcacc tgaaaaatgc aactgaaaca gtagttccct gggaccacac actcagaaag    6120
ggggtgtatc aggagatcta gggaccagga gggtggaaga cctaaggcag cactacagat    6180
gatggagaaa aacccactgg ggaggggcga tcctaaccct gagaatcact gagatcatgc    6240
agaagtattt gatcctacag cattaatatt gtattgtatt gtattagtat atatatatag    6300
tgtatatata tagtattagt atatatattg tattgtatta gcatatatat actaattgta    6360
ttgtattgta tttatatata tagtattgta ttagtatata tatacagtat atatgtatat    6420
atactaatac aatgtactaa tacaatacaa taccatatat atatacacta acacaataca    6480
attagtatat atatatatat atatactaat acaatacaat actatatata tactaataca    6540
atatatacat atatactcac caagacatat tagtggtctg atgtctggct gccacactca    6600
tcttctacct tcagctctgc tctaccaaat atcatttgtt tctgggatct ttgcagtcca    6660
aggaacttca tccttgatat cccacccctt actaactttt ttttttttt ttttttttga    6720 gacggagtct cgctgtgtca cccaggctgg agtgcagtgg tgtgatctcg gctcactgca    6780
agctccacct cctgggatca caccattctc ctgcctcagc ctcccaagta gctgggacta    6840
caggtgcccg ccaccacacc aggctaatgt tttaccgtgt tagcaaggat ggtctcgatc    6900
tcctgacctc atgatccatc cgccttggcc tcctaaagtg ctgggattac aggcataagc    6960
caccgcaccc ggccacccct tactaatttt tagtaacgtc caaggattaa aggaaatttg    7020
ccttacctat ttaacaggaa tcaacagggt taatctcact cccttttctaa aaataattta    7080 taaacattgc agacaatctc atctatccct gtctaaactg tgtggaatta ctgccattta    7140
atgtaatcag tctactcatt tagttttgcct aaggaatttt tgaaaaaaca gttaaatgaa    7200
tgacttaatg gaataaccag gaagttgaag tctccaatag taagaatgaa ctcttgctct    7260
ctggataatc aaatgggtcc ttcctccttc aggtagatca tgccatttcc tcacttacac    7320
tgaacaggta aacaacataa ttactgactt caacttctag ttaattcctt cttttatcac    7380
tgagtatcct ttggctggga gttttgttgg ctatgctgcc attttttcta gttatcacag    7440
tcctataaca taccaatcct tcaatataac tcatctttaa attgtggttt taccttctca    7500
agaagttatt aattatgcca gtgctaaatc ttctaaaatg attgttgact tgttgattag    7560
```

| | |
|---|---|
| cccccatgca attcccctct cccgtccctc agcacgtaag gaatggccct ttgcttactt | 7620 |
| ccacagatcc ttaaatctac cagttagaag ctaatagcct acctctctac caggaaggaa | 7680 |
| ctgtgggctg aacataata catgttgact tataatttct tagaaaattg tgtgagaaac | 7740 |
| atcaaactcc tgattccagg atatgccaaa gacacatcat taaaaagcaa aacaaaacaa | 7800 |
| aacaaacctc atttgacgtt gctagtagtg gcatatttca tcaagatcag ctcaaataaa | 7860 |
| tagaagtgag attttcacac aaattagact gtagtgcttt ttttttttaac ttatctttac | 7920 |
| catatgattt ttaacggtaa aaaaaatcgt ttgagatatt agatgtataa tatttatcat | 7980 |
| ccaattactt cattagttca atctttttc aatggcgctc ctgcatctga gaataaggtc | 8040 |
| agaaaatttc atgttctgat ttcatgctga ttttcagaag aaaaatgtta gttttgtata | 8100 |
| gaataaccca tcctaagaaa tacatttctt attatatttc ttatcttata tttcttagga | 8160 |
| caatgagcta ttcaaagggt gatgataacc agcaccatca gtcagcatta tctaagaata | 8220 |
| agaatctgtg tttctacata cagacctcct aaaaaggaac ctacacttaa caggattccc | 8280 |
| caggcaattt ggatgcacat taaagcttga gcaacactgc attagaaagt tagttttcca | 8340 |
| tcacaaaaac agtaacaaaa ggaatataaa gtaagttact ttaataatat aagaagaggg | 8400 |
| gcaggccggg cgcagtggct cacgcctgta atcccagcac tttgggaggc tgaggcgggt | 8460 |
| ggatcacctg aggtc | 8475 |

<210> SEQ ID NO 13
<211> LENGTH: 8401
<212> TYPE: DNA
<213> ORGANISM: Homo sapiens

<400> SEQUENCE: 13

| | |
|---|---|
| tttcatctaa gactacattt ctattgtttt atataatcag ccccccctaag atcaacatgt | 60 |
| ccacattttt tggcaaagac aaagcctact gatttcagga tcattatttt ccttttttcaa | 120 |
| aagcacaaac ccaaactgag aaataaatca agagaaattc tccttttttc tatgctaatt | 180 |
| tagaagtaga gtcttatttt cttttcaaac ccaaagagaa tcagacatac aatatgaatt | 240 |
| tatctacttt cgcttgctca gactgagagg aaagattaat attttcaggc tgttagtcaa | 300 |
| aactgttcat tcaaatatta tttaataaaa tccaagaacc agctaaaaag tcgcttaagc | 360 |
| taagaaacct tcaccagcct catgggaaat tgtgtacagt tttccactag aatagcctat | 420 |
| aaatgcttac tgaaaatgtc taagttcata tcttggtaac taacattta attcaatctg | 480 |
| cagaataata tatgcttctt tagtgctaag atatgaatat tagaggcatt ctttcttaaa | 540 |
| atttctattt agttatactt tcacaaataa ctatataata ttaaaattct gcatgtggca | 600 |
| taaaacatat tttaatggag aaggtaatgt gtagggagtt tatttctgtt tgctattaga | 660 |
| acttgtgttt attcttggtt aaaaaaactg cagattacaa catagaaaaa aacaaaagta | 720 |
| tgttgtatat ctcttacagt agaagataaa gagtagttct aaatttagaa aggaaaaata | 780 |
| aatatacaca gtgaaaatat gtgtcagtga gatgttaatc aaagatcaac tattgctgag | 840 |
| accagcaata ttaaatccct gcacaattac tcatattata atgagaattt taaaaagaaa | 900 |
| atatgaacac ataacataat gaaggcagaa gtcactctca tccttcatct ttgtattccc | 960 |
| aattcaggaa gctggtatag tatcttcatt ataattacta ttcaacaaac atttgtaaaa | 1020 |
| tgaatgaata aggaatgaat gatgagaaaa atgataaaca tctccctctg tctcctggga | 1080 |
| gttaactgca ctacttctt ttaaatttaa ttaatcctca atgtccttgt aaaatagcca | 1140 |
| aagggaaaat gtatttacat tactctaaat attgatgcaa tctacaaaaa gtgttaaaca | 1200 |

```
acttcctcaa agtaaataaa atgttcacaa tccagctagg ataaaaggat ttaaatcatt    1260
tcctaggtag agggctttca attagagccc ctgctgcatt aaccatggga actcatctca    1320
ctctcttcat gatggagccc tgagtgttgc tgctaatctg tactctacca ttctaatgct    1380
tttaaggttc cttttcagcc cttcctcctc gtaatccaca aatactgaga ccaaggcatt    1440
ttttgggtca gtcctaattt caagcattct atcctgccct ccccaaatga actcacactt    1500
attagaccat atgttcctat attagttcag gaaggggggaa aaaatgttaa tcacacttgt    1560
atataagaga tcatagaaaa acagtttact aacctgtgaa aataccattc attctctgtt    1620
tacctctggt ccacagctaa gcaatcagca ggatataaat gtaccctatg ttcactattc    1680
agtattcata agtatactac ttatgaattg gaaatctgac acaacattta catgacctaa    1740
ttttgaaaat ttaaaatagt gtaaggcccc taggcttaat tttacagggg aaagattaaa    1800
gggacacaag caaacatata ttctctctct gtgctgtggg acactggtaa ttttttgact    1860
taaaatattt gatacttaaa atgccaaact tctacatttc tgcagtaaca aggcagttat    1920
catattgaat accatttctt tctctccagt aagtagagtt aatattagca catgaactga    1980
aaatattaag tgattataaa aacgtccaaa taaattcatt aaaatttagc ttggcaaaat    2040
gttagtttca tgttcttggt agaagtcctt ttatatttat attcaaatga aatgaacaat    2100
ttacaagcaa aggaaatggc atcaaatatt tcacaccctg cctcccaagg tgtattgatt    2160 catgctttt gctcagatct aggtttctcc actcaggaaa agaggagaat gtacccatac    2220
ttgggaaaac aagtttccga tggcacagct ttgatcaaac agcaaaattc tatccatcta    2280
tgtattgcca tctgacagta tgacaaatgg tcccatgtgc gatattcaca ctgcattgca    2340
gtcaaacctg taagtcaaag gatatgaaat aatagtaact atacattaag cacagaagaa    2400
aatgaaacaa acaaaaaggt tttaaaccaa ccaaaaatat gtcttatttt ggatgttcta    2460
tatgttctta cattctctca ggtcttttgt gtcattatga acacaattct aacaagcttg    2520 attatttat ttccattcac atattacagg caacaagctg aaaaagtaga acggggtgta    2580
gagagacagg acaaagtaca gattagggct tgaagtgccc ctgaccagtc gacagcaacc    2640
acatggaata atgactcatg tgcattaatg atcacactaa atgatatttg ttttttacc    2700 tagtccttca actgacagct taaagaactt caggttgttc tgattcttga gcctcctcta    2760
cagcttcaga gaggactttc attttatttt ggatcaaatg ctccacaact agttgaaact    2820
ggaattaaat tttatatgaa gttcctagat gatttaaagc tgtaagaaga agaataatga    2880
atcataagaa aacttgctgc tacagatatc aaaaaggaat gttaccatcc ctcatgctaa    2940
tccttttcat tttaaataaa caggatctaa aaaaaataat gctgggaagt cctaaccaca    3000
tcaagaatgc ctcagatcag tgacccaggg aaccttccag aatggatgaa atagacccaa    3060
agctgaattc acctaatttt agggccaaaa acccaaaaaa caaaacaaga ccaaaaaaat    3120
cttcagatac tgggagaaca aatctcaatt gctcaattgt atcttatgaa acaattttt    3180 caaaataaaa caagagatat ttaagattca ttaagttctt gtcatttcaa attttaagaa    3240
aaatattttc taatggaatt acatatattt atatgattct tctagttata tccatggtaa    3300
taaatactct tttcagttgg aaataaaacc catttgtgct atattattag ggaaaatatc    3360
tacataaatt agttttaat ttaactaaag tctatctttt gaattcataa gcataaaatt    3420
ttaaccactt gcaaaattta taacacactt aaggtagtca gatgccttgt caagtagttt    3480
aacaaaagtg atttcacct gtttgtttta ataacagtgc atcgatttta tgaaaatcag    3540
```

```
gcatgccctc gggtcctaac aaagtatacg aagctgaatg gatctatgcc aaatatgcca   3600
gattttactt tctgagtctg attttatact tctgtcctct ttcttaccac atggcttcca   3660
gtatcactta cagactaacc cttcaaaagg agaaggctaa gttactaaca tttggaaggc   3720
ttatgaaagt gaagcatagt tatgagccag caatgttttt atttagggaa tgtgtgcaaa   3780
ccatacactt aagcaagctc tggggaatga gagttggggg gaatcaactc ttttatttgc   3840
taattggtat ttcctttaaa agatagagtt cttccagatt ttaactgtgt taatagttac   3900
tctagaaaaa ttggagattt gtgtgcatat attttatgtt gtaaacagac acatacccag   3960
agacactgag agagacagac agacagtaaa cagaggagca ctaaccacaa acggtttaca   4020
aatgacctct gtgctcattc acctgtctgt tccccacctt gccttttata gcaactatag   4080
caacagccat gagagtcatt gtggaaagaa ataaaataaa attaaaaaat cctggaagct   4140
tgtaaagaat gtgagcaaag gggaggaagt tgtgaaaaaa atgaataaag ggcaccgatc   4200
cagagtattg aagaaggcag agtggagagc ctagtaatga gtatctggta ccccagtatc   4260
ctctcccaca gaatctgtac agctctccgt ttatgacagt ttaaacttaa tttaaattat   4320
caaacagaca ctttcctcaa acatataaat gatgaggcag ttcattcagg ctgtatgtat   4380
aaagttgttc cagccacctt tttctaatgg cttctctata tcttttacat ggagacaatg   4440
agagatttgc ttaggacaat ttgactgtaa tttagaagta ggaaatggga agtatttgta   4500
tcttctttgc ctaactcaca ttagttactc aagtaagcat ttcttccgtt attgcatttt   4560
cctgattaca agttttatgt tttctctaaa acacatatca aagaaatgt cctaagcact   4620 atgcagggg aagccatgac atttatccac cactgtcagc aaaaacatga acttagccct   4680
caacagaata tttcacttca ttctagtgtc acctctgcgt cacctgcact ggagtcacca   4740
cttgcctgtt gggtaagacc aggatgcacc gctgaaataa aaaggggtca gacaatacaa   4800
gaaaagccag tagaaattgc caaatgtatc agaatacaca caggctttct aaggatatgg   4860
cccaagagga aggctctaga gcccacccctg aaacaggatt tttgacttca cagataaatt   4920
atttaatttt caataacaca attcaattaa agaaagggaa atacaaggct aaacaaataa   4980
gaaatgaaga caaaaaccca accttcaaa tctaaagaaa ataatctgtt ttaaagacac   5040
agatgaagat caggaaccca aaacagaaga aaggaaaggc aattaacgct ggcatctgat   5100
aacaacgaaa agtatggagt ctggagaatc gctagactct aaaaattata aaggtttaga   5160
cttggacttt gtacactgaa gaaaagaaaa ctgcatgcat ttatactgac caatgtacac   5220
tattgctgct ttttaacttt tgtgtatatg tagggtagat ttttttttaa gtgaaagcaa   5280
gcttattaag aaagtaaaag aataaaaagg tggcttctcc ataggcagaa aactagcgta   5340
gtttttttat tagaaattgt tattcaataa tagtacatgt tacaaataaa taccatttta   5400
aactgaaaaa attgtagact ttcaaatcag ttagggtggt caccctaaaa aagggcattt   5460 tttccccctta gtctccttgt tcatgttgct cacaacaaga aatgggctaa tgctatgaat   5520
aataataaca aacactgcct tctgtcaggc cctgtgctga ataccgtctg catatgtata   5580
ggaaagggtt aactcagcag gtcttgtttg cccagactct gtacatttcc aagaaaggtc   5640
tgcctttagg actggtcctt ggccagctcc tggagaatga gctctcagct tttgaaaat   5700 tctatctgct aagaatagtt ttgcatgtct caggtcttgg gccacaaaat atcagtttaa   5760
tcagatggtt tatgttaaca agtatgattt atggcaaaca tagatctcta atctccattt   5820
ctctctcata tatctatatt tatctatcca tatatatgta cctatatata tcaaatatga   5880
agatatgttt atagcaattg catataaata gagagatagt atgtagtagg aagagagaca   5940
```

```
tagatattat tcttcatttt agaatgttat cttggtatgt ttaaaaggaa aaacttaaga      6000
tgtgttgcaa ttgcagtatg agtttcaggt atgtacatgt tatgtgtgtg tgtgagagac      6060
acacacaaac acatttcaaa catgttttat gtttaagctc aatattcaaa cacagaaata      6120
taacatctat tcttaatatg ttttatgtaa gtacagcagc agcattatta aatactgtat      6180
ttctatggtg attgaaaatt agtaggcaga gaattttgt aatggttctt aataatttt        6240 gtaatagtaa atgattactt tttgtttagt atagttttat aatctataca tgaataaagt      6300
ggatatttct attcatatag aaatgtgatt tactctcatg tacttatcta catgctaaaa      6360
ccataagtta tcaattttag ttctgtgcca aggcacttt actgaataaa aataatcagc       6420
taattttata ttttcctgat tcaaatttat atgcccgtgt aatgttccgg ggtttttttt      6480
tttaatttct gtaaatcaga atattcagat gttgaaaaag tctttgcctt cagatttaaa     6540 agatacctt gaaatgtagc atatcccaaa atgcaaccca gaggctggca atgtcaacat       6600
ttttctgttt taaaaaacct cttatgaaaa ctattgccat actaaatttt ttacttgctg      6660
atgacttaca gctggaaagg attctgtaca tataagacat caaatattga ggatactgga     6720
acttttaaat taatggcaaa gaaagtcaac aaaggaagtt catatgaaat caaactagta     6780
atatgattac aaaaaaaaaa gtttaaaatt tttcttggcc ccagtcttat catttctgag      6840
ccaaatacaa ttctatcgaa atcacctgaa actgaaatca ccattctagg ctggttttcc     6900
cataaagatg gactgctcca aaaagaggaa tcaagaaaga atttggctca cagtgaatta      6960
ttcactttgt cttagttaag taaaaataaa atctgactgt taactacaga aatcatttca      7020
aattctgtgg tgataataaa gtaatgacca ctttcagct ggagggacta acttctttt        7080 tttttttgct gcatatatag ctgtggtaca ttttaatgtg aaatgatgac tgcatcagct      7140
tatatccatg gagcagattt tagcattcag cttgggtctc ccagtcaata tctacgagtc     7200
tcttcttaag gagatcgatg acacagatac atacagacta acaaatgtga taccaataat     7260
caagaattca ctcagttaag attttgccca ctgatttcca cacaagaaac ctagaatta     7320 ctagattctt gtgcctgtga ggctccactc atttccctga atcacaaaag ctacagagta    7380
tttagataga aatataccta ctcttaacat gaaccatttt aaatatatgt attactgtgt     7440
ccacaggagt acactttaaa gcagggactt cactcttcaa tctctccaat cacgtgttac      7500
ctaaagtggc atgtggttcc ctaaagctta ataactgaca ttgccttaaa aaaggggttt     7560
gcttcccgac taatgtggaa aaagtctgaa aaatgatttt aaatctttca ctaaatttct     7620
catttggtca cgtggaggaa aatgatttca ccaaatagat actctcatta atttttaat      7680 gtaatttatc aaagaaatga aatatttaga taaattccag atttccccca ccatgagctt     7740
ctccgaaagt atactccatc acagactgct cactaagaag ctctactgca gtcaaagtga     7800
ccgaatttaa ggggacataa tgactacttc tgctacacag aaacattatc catctctaac     7860
acttccctat gagatggaag acggacttct aatcaggtac cagagagggc tctgccaact     7920
tcagggcttt gatgaataag aatggttgag agcgctcatc ataaatgaat tcagtataac     7980
tgagtgagaa agtgagagaa ccagagaaat aaatcctcat gtagaaaatt taggggtatg     8040
aaatgccaaa tgccagttaa ccaaagcttt cttttgtcata aagcaacttc tataaaaatt    8100
gctgaaaata aattcttcat ggctcaatgt gaatcagtaa tttccatctc tattacactg     8160
ttgtttaccc aaaaactatt tttaatgact aagactcaga gttgccaga gtgttttcca     8220 caaaacaact gttttgagat actccagatc tgtaatcaag taagtctgaa aaaccccaaa     8280
```

| | |
|---|---:|
| tacctcactc acctcttgga tatgcataaa gcacactaat atataacgtt ctaaaaagcc | 8340 |
| aatcattaaa accgttttat attgtttaag catttcctag acatatttgg ctacaaatct | 8400 |
| a | 8401 |

<210> SEQ ID NO 14
<211> LENGTH: 8427
<212> TYPE: DNA
<213> ORGANISM: Homo sapiens

<400> SEQUENCE: 14

| | |
|---|---:|
| gcacctgcca ccacgcccag ctaattttct attttcagta gagatgaggt tttgccatgt | 60 |
| tggccaggct ggtctcgaac tcttgacctc aggtgatcca cccgcctcag cctaccaaag | 120 |
| agctgggatt acaggcgtga gccaccgcgc ctggccatat taacaaattt taaatcacaa | 180 |
| ctatgtgggg ggggaggcta gtattattac agcagattgg tttgctatat aaacaagtac | 240 |
| tttaaaaaat atttcttggg ccaggcgtgg tggctcacgc ctgtaatccc agcactttgg | 300 |
| gaggccgagg tgggcagatc acttgaggcc aagagttaag agaccagcct ggccaacatg | 360 |
| gtgaaacccc atctctacta aaaatataac aattagccag gcatggaggt gcatgcctgt | 420 |
| aattccagct gctcgagagg ctgaggcatg agaactgctg gatcctggga ggcagaggtt | 480 |
| gcagtgagct gatattgcgc cactgcactc catatccagc ctgggcaaca tggcaagact | 540 |
| ccgtctcaaa taaataaata aataaataaa taaaactaaa ggcagagttt tcttaaataa | 600 |
| acatggtagc cctcagcaac aatattgtaa gaactcctcg caagagaaaa agctggaata | 660 |
| agatactggc taagcaagta agaaaggcac tgccctgctt ctgcatacat tcaaactaag | 720 |
| acatatacat tgcagcttac acttacattt tccaatatcc ccaggcatcc ctttcccttc | 780 |
| tcaaacagcc aaaaggaacc agccatgcaa ataaaaatac aagttcaaga gcctaaaaga | 840 |
| agtcagtgtc ctaaaagaga aaattaatgt aaagaattaa gatttttga aactacactt | 900 |
| tctttctggg gctgtttact ggcctccaat acatcaatcc tgtaacactg tgaactacag | 960 |
| tgatagattg gtacatgctt ctaaacacaa cagaattttt ccaaggttac atacactgta | 1020 |
| acaaaggggg cattttgcag catcttattt tccttaatca actagtttgg atattctaac | 1080 |
| agtgcaaaca ttgtaaacaa taaattttca ttaccttttg aactttctga agtcaaccaa | 1140 |
| aggcttgtgg tatggatgca atgagtacta gacaggcaga gctgaatact agtcaaaata | 1200 |
| ttcagttact ggtgtgatag tccttttggg ggcatacatc acttagggag aaactgaggt | 1260 |
| gcaaggacat tttacacaca gcaaaaacat tctcaggaat ttgtcacatc attaccataa | 1320 |
| gccaaaaatc tcaaggtctt agaacagcct gagcttctga tcaaattata ttgtaaaaag | 1380 |
| agaggaaaaa aatgtgaagc gtgctatttt ttaaaataac agtaactact actactgctg | 1440 |
| ctgctgctaa ttctaaacgt ttactgagcc cttattatgt gccaagcacc gtgctaggta | 1500 |
| cggtcataga ttttaacaat taatccctgt aacaaccctc tgatattagt taataaaatt | 1560 |
| aaagtagaat cctcaccaaa aaatttaaa ctttccaaat aaaatataa ataaattatt | 1620 |
| aaagacattt cacctctttc tctgcctcag actacatttt caagtattaa atttacacta | 1680 |
| aaaccacatt tattttcagg aattccagtt aaagcgtaca gatattcaag atgttgacaa | 1740 |
| ttattacaga agaatcacag aactctgaaa ttaaatactg gcacagaaaa ccttccatcc | 1800 |
| aaccttacgg aacaactatc cccatttta aaaaaagga acagcatata tatcaggctt | 1860 |
| gataataaga ggcttctcat gcccacacta gcatgaatg atgccataat tataaagaga | 1920 |
| cctgtatcgc cacatgcata aaaataattt acatctgcta agtcaagttt tcaatatatt | 1980 |

```
attttgtgtg taaaccttat agtagctgat aaaaaataca ataaactaat ctaaggtaaa    2040
ctaaaacact aggttgtttc tgaagactca ctttagaatt tgagcagcat aataatcata    2100
atattagtaa tcaaactact tagcagaaag ttcttagagg gctgggaagc tgtgtataat    2160
aaaatggagc agacaagaag gaagggtttt ccgtactgtt taaatcaact acaggtccca    2220
gcatgcagtg ctctaatctg aagttaagca aaaactgcaa tgcatactgg gacttgtagt    2280
aagtaaacca cgttatcaca gcaagtttca agaaagtctg aactatctag cacaatttga    2340
ctatatctta ttatcagagt ctaatcaaat ttaaatcaaa tttgtatgtt ctctgatgtg    2400
gcacacagtt tctctagcac ataccggaaa aagtatcaat atttagacca acattttcac    2460
attagaaaaa tcttacgtag gagaagcaca gaaaaaaatg ctgaaaaagc aaaaaaactt    2520
gatgaataaa aaatataatt tttgaaatag ttttttaaag tttgaatgga tccatttcaa    2580
cattctctaa tcctccccca caaaaagttt aattgttttg gccgggcgcg gtggctcacg    2640
cctgtaatcc caacacttta ggaggctgag gcgggtgaat tacgagatca agagatcgag    2700
accatcctgg ccaacatggt gaaaccatct ctactaaaaa tacaaaaatt agttgggcgt    2760
ggtggcgcac gcctgtagtc ccagctactc aggaggctga gacaggagaa ttgcttgaac    2820
ctgggaggtg gaggctgcag tgagctaata tcgcaccact gcactccagc ctggtgacag    2880
tgtgagattc attctcaaaa aaaaaaaaaa aaaagtttta attgttttaa caggttgctt    2940
tttaacaatt attcaagatg tatttataa ataatttttc ttgaagaaaa ttctcagaag    3000
caaacattcc ccatattcta atattgccca ccaggaaata attttttttag taatacgcac    3060 acacccatc acaaaacaa acaaaaaaca ctgaagttct gcttttgtca agtccttact    3120
caatatttat gccctccatt cctcacctct aattccctac acacacacac acacgcac    3180 acatcccac acacacacgc ttctacaaag aacacttaga aaaacagtat tccaactaca    3240
agcccacttc tctcatccac tgacctcttc tgaaaacaca aaagattttt taagctatca    3300
gtaacacgtc caaacacaag ctgataagtt tgagctagaa tttacatata tacagttgct    3360
acacaccctc ctattttctg caagtctgtg gaaggaggct gggaagaac taagtgcaat    3420 ctgcatcagg aggcctaaca caggtggtgg gttattttca ggcaacagca ccttcacaaa    3480
catgttttgg aatatagtcc aagaaattcc taacaaggaa agataagctg gcacacaaat    3540
ttaacgcaat ccagctaaaa atcatctgca acacatgcta ctacatttca ccataaaagt    3600
gacgggctac tataaaggat ttgaagcttc gtcaatacaa catactgtcc ataaggccag    3660
agatagcagt tgccatggtt actataccca ctttttatcag gaaattactg tcattacccc    3720
aaagttttgg gtacttattt aaaatttaaa aaaacacac acaatttagg gttctgactg    3780
ttaattgagt gaaataatca actactgttt gatttgtaag tatgtcgctt tggagatgca    3840
catggttaac aatacttgga tctgcagcag aaaaaaaatc aattcctttc tgctgctcct    3900
tctcctcaag tactgacagt ttgtattctc aatgcagcca aaacaataaa acaaaaccca    3960 tcttttttggc ttctgtgttt aagttatttt tcccctaggc ccacaaacag agtcaaaata    4020
aagcctagat catcaacctg ttaggcctca tcccttcct atccctcca tactggttca    4080 ctttcttgac tacttagaaa aggcagaaaa catttctgta actgattcca agtatagaa    4140 aagaatagtt gccttcaact gagatatttt caccaaagtc ttttttattt acttttttt    4200 taaggcaggg agaggggaga gacttgcagg gtactgaaag ggagaagtgg aggagtattc    4260
aaattgccac acaagtctag tgtaagaaag ttgctttaga agagtccaaa ggatggctga    4320
```

```
acctcacata taatttctaa aagctttgga agagttcacc ataattttaa gactgaattg      4380
agggacaagt aatagaaaag ttattcataa agtctacttc aacattttta caaaagataa      4440
ctattcaaaa atttaacaca catataagaa ttatacgaaa gcctacaaaa tagtatggcc      4500
acatatacac acaaacatac aaagtagaaa acataagcta tttaagaaat aattatctac      4560
aataaattca atgcaatgtt aacatattat ctcttttta aaaaatcgca aagcagcaaa       4620
aacatacacc tgagaaaatt aatgtgatca aaacgttaaa gaattcttag gcctataaaa      4680
aaagcccatg tacaaaagct cctgagaagt caacataaat cattaatatt tcccagcaca     4740
aaataatatg aaaattcaaa catgtttcaa gaaatcagtt ctagatatag atataaaaga     4800
attccattaa aggtcagaga cctaaaactt taattccttc ccttctctgt ttgaatagta      4860
attaaataca aaagccttca gcaataaaat actaaggata caaaatttaa aagcacatta      4920
atataagctt aacttcagta tgtcttcaca gaaagcttta ctattcactg tctgtaggat     4980
gaaaaagtta ataacaccct gagaggtttc atttttatct aaacagttaa gtgtttttct     5040
caccgttcac agaagcaagt ttctatattt acttctaaa gggggcaatt tcaaaagaat     5100
agtcacttct aaaatttaag atactatacc ttttgatagg ctcataaaca cagggttcct    5160
aattatctat attttacttt aaaatgtttc tattccaaat ttgtgagcag agtttataag    5220
aaagctgaaa ctcaaggctt taaacttttg ggttattttt acacaaaaat atttcagtgc    5280
actcctctag atttgagtag tcatttcctt gtgcatcctt ctaaaataga aaacaaaaa      5340 tgatatatcc atatatacct aatactaaca catacagata tacatctttt tcactgtgaa    5400
acaagcttga aagctttagg cagtaagaat ttttcagaaa gttagcagag tcagtcaaaa    5460
cattcaaaac ttgaaccatg acatctgtta ctctgtcaat aagagtctat agaagaatca   5520
gggaacttac atactcacta aaatcaacta ctatcacatc acatcaatgg agaaatgaag    5580
aaaaactgta ataggggaca tacaattcac aggatcttca aaagggaaaa tgatctttt    5640 ttttttttta aattatgaga aactgactag gcagcatttt ttcaaaagca gcttcaaaac   5700
tataacaaag acatttttgg taaccacagc agtatttaaa aaacaaaaat ttaggccggg   5760
cgtggtggct cacgcctata atcccagcac tttgggaggc caaggcaggt ggatcacctg    5820
agtcaggagt tcaagaccag cctgaccaac atggtgatac cccgtctcta ctcaaaatac    5880
aaaacttagc cgggcgtagt ggcggacacc tctataatca cagctactca ggaggctgag    5940
aggcaggaga atcgcttgaa cctgggaggc agaggttgca gtgagccgag atcacgccgt    6000
tgcactccag cctgggaaac agagcgagac tccgtctcaa aaataaaaa aataaaaaaa     6060 ctatagtgtc cagggtgcac tttaaatgta ttactttctc aactgatatg gaaaaagtta    6120
gcatttaaag acagaagctt ctgtccatgt attaattagt tacctatctc aacaacttaa    6180
tatctgcatg ctttcttacc atttatgaag aactttata tgtattatct catttggtct   6240
tactgagaaa acagtatttt gcctacaaaa tagacaaaat tcaaagcaga tttatcaaac    6300
tttctagcat ccccaaattt ttaaaacttc gacacaaaac tttacaagca accacagtgg   6360
catgatattt tcagtgataa tcaattcacc taacactaac agagtttcaa aggaccatgt    6420
gctataaatg ctatgaaact gttaaagtag ctatattcat ctttatgcag ttactgttac    6480
atcaacaatg acctaccact gatacaactt gacttacagt tcaagaatct cagtctttgc    6540
aggctaactt aagtacatca accatatgta tttataaagc cgagtgccta aaaattgatc    6600
tatattagaa tcatagtctg taaatccgag gggaaaaaac tacaagaagt ctaaaatttt    6660
ttcaacacac tatacccctt tccaaaatct caactactct atatcctatt tgtattaata    6720
```

```
ttatagggat gataacaagg cttaaagccc taaatcatac caactacttt tgtttataac    6780
aattacaaat aattttttaa aatacatgct caacatccca ctcatcaaca caagactaat    6840
tccccttcca aataaaataa ttctaaacag tgctctgtac caagggccag aatccttata    6900
ctatccgcaa tcgcacatct actttgtaca gtcaaagact tcactttcaa gtagcaaaca    6960
ttatttatga atggaattt taaatggact tactcaaaat ctttctggaa ctttaaggtg      7020
ttaatcctgt tgcttagctg aagctaagca gagctgtaat aagtagcaag accctcaaaa    7080
ttcaaaaatt tcctttatct tgctgtagca cctcctgctg gatagcattt agagatcttc    7140
atgtaagcag aagaagagta tttcagaggc agctccttcc agaagactga ataggaaaaa    7200
ggatggaccc ttcaaagcta aagaaatag gccccatcca tcacttatac cttctaaaaa     7260
tacaatttag cccaggtagg tgtcttttc atctattact actccagttc cacaaagact     7320
tgcctcagtc caaatacaa catgcttaaa taagcctgc aaaattgtct aaaaactaag      7380
ttaaaaagca ttcaatagca cccaagcaaa acactttatt atgggcagcc aagcaatgtc    7440
agtcaaactg taaatactat tatgttacca aaagcaaaag tctgatgtta aaaaaaaaa     7500
aaaaaagcc cctggaatat tcgtaacatg ttagccagat gtttgtgttt tgagaacttt     7560
gtgcactatt actatgctct tcacttaagg atagttgtac atctacaaac gttttaagta    7620
cagaaatttt tttataaaca ttagcataac tgtacacaaa atttcctctt tgccatgaaa    7680
agataggtcc tgggatttga aaatgtattt ttcagacatt tttaatgacc ccctaaaata    7740
aactagtttt aagcccacaa caccgattcc ataaacaagt aaagacagaa gaagagaata    7800
agaaggaact taccaaaatt aaaatgaata atagtatttc cagtaaaaat gtagtaacag    7860
tttccaacaa tgctgtaaac caaataaatt gtgaaactta aaaaggaag gaggggggcca    7920
gtcttcaaag accaaaagca aagctgacct atttatttct attgcttaga gtgaacacca    7980
gatgtaaaca aatatcataa acactgaaaa gtacgcttac atggtttagc ctcaatttca    8040
gtacccttac caggccctca ataaagctac agatgttggt gagaactcgc tcaaaaagga    8100
gataattcca gcccctcgcc ttaaagaatc cctatcaagt gaacctgtga aaagacttcc    8160
ttcccagagt gcacaactgc tttaaaaaaa aaaaactttc atcagcccaa attaatctga    8220
ttctaatatt caactatcca ttatttatat ataaatgttc ttccctctct aactttccca    8280
gctcgagcat ctacattcct gacaccgact attagcaaaa atgcacaact ccttccccag    8340
ctatggggca atctttgaa atctgaaaca cagccacaaa gttcactgtc aaggccaggt     8400
gatgaggccc acacatgccc ggacctt                                         8427

<210> SEQ ID NO 15
<211> LENGTH: 1704
<212> TYPE: DNA
<213> ORGANISM: Artificial Sequence
<220> FEATURE:
<223> OTHER INFORMATION: Synthetic Fragment A

<400> SEQUENCE: 15
ggtaccaccc aagctggcta ggtaagcttg ctagcgccac catggtgctg cagacccagg      60
tgttcatctc cctgctgctg tggatctccg gcgcatatgg cgatatcgtg atgattaaac     120
gtacggtggc cgcccctcc gtgttcatct tccccccctc cgacgagcag ctgaagtccg      180
gcaccgcctc cgtggtgtgc ctgctgaata acttctaccc cagagaggcc aaggtgcagt    240
ggaaggtgga caacgccctg cagtccggga actcccagga gagcgtgacc gagcaggaca    300
```

| | | |
|---|---|---|
| gcaaggacag cacctacagc ctgagcagca ccctgaccct gagcaaagcc gactacgaga | 360 | |
| agcacaaggt gtacgcctgc gaggtgaccc accagggcct gagctccccc gtcaccaaga | 420 | |
| gcttcaacag ggggagtgt tagggggcccg tttaaacggg tggcatccct gtgacccctc | 480 | |
| cccagtgcct ctcctggccc tggaagttgc cactccagtg cccaccagcc ttgtcctaat | 540 | |
| aaaattaagt tgcatcattt tgtctgacta ggtgtccttc tataatatta tggggtggag | 600 | |
| gggggtggta tggagcaagg ggcaagttgg gaagacaacc tgtagggcct gcggggtcta | 660 | |
| ttgggaacca agctggagtg cagtggcaca atcttggctc actgcaatct ccgcctcctg | 720 | |
| ggttcaagcg attctcctgc ctcagcctcc gagttgttg ggattccagg catgcatgac | 780 | |
| caggctcacc taattttttgt ttttttggta gagacggggt ttcaccatat tggccaggct | 840 | |
| ggtctccaac tcctaatctc aggtgatcta cccaccttgg cctcccaaat tgctgggatt | 900 | |
| acaggcgtga accactgctc cacgcgccct gtagcggcgc attaagcgcg gcgggtgtgg | 960 | |
| tggttacgcg cagcgtgacc gctacacttg ccagcgccct agcgcccgct cctttcgctt | 1020 | |
| tcttcccttc ctttctcgcc acgttcgccg gctttccccg tcaagctcta aatcgggggc | 1080 | |
| tccctttagg gttccgattt agtgctttac ggcacctcga ccccaaaaaa cttgattagg | 1140 | |
| gtgatggttc acgtagtggg ccatcgccct gatagacggt ttttcgccct ttgacgttgg | 1200 | |
| agtccacgtt ctttaatagt ggactcttgt tccaaactgg aacaacactc aaccctatct | 1260 | |
| cggtctattc ttttgattta aagggatttt gccgatttc ggcctattgg ttaaaaaatg | 1320 | |
| agctgattta caaaaattt aacgcgaatt aattctgtgg aatgtgtgtc agttagggtg | 1380 | |
| tggaaagtcc ccaggctccc cagcaggcag aagtatgcaa agcatgcatc tcaattagtc | 1440 | |
| agcaaccagg tgtggaaagt ccccaggctc cccagcaggc agaagtatgc aaagcatgca | 1500 | |
| tctcaattag tcagcaacca tagtcccgcc cctaactccg cccatcccgc cctaactcc | 1560 | |
| gcccagttcc gcccattctc cgccccatgg ctgactaatt ttttttattt atgcagaggc | 1620 | |
| cgaggccgcc tctgcctctg agctattcca gaagtagtga ggaggctttt ttggaggcct | 1680 | |
| aggcttttgc aaaaagctcc cggg | 1704 | |

<210> SEQ ID NO 16
<211> LENGTH: 1120
<212> TYPE: DNA
<213> ORGANISM: Artificial Sequence
<220> FEATURE:
<223> OTHER INFORMATION: Synthetic human IgGl signal + human IgGl
      constant

<400> SEQUENCE: 16

| | | |
|---|---|---|
| tgctagcgcc accatgaaac acctgtggtt cttcctcctg ctggtggcag ctcccagatg | 60 | |
| ggtgctgagc caggtgcaat tgtgcaggcg gttagctcag cctccaccaa gggcccaagc | 120 | |
| gtcttccccc tggcaccctc ctccaagagc acctctggcg cacagccgc cctgggctgc | 180 | |
| ctggtcaagg actacttccc cgaacccgtg accgtgagct ggaactcagg cgccctgacc | 240 | |
| agcggcgtgc acaccttccc cgctgtcctg cagtcctcag gactctactc cctcagcagc | 300 | |
| gtggtgaccg tgccctccag cagcttgggc acccagacct acatctgcaa cgtgaatcac | 360 | |
| aagcccagca caccaaggt ggacaagaga gttgagccca atcttgtga caaaactcac | 420 | |
| acatgcccac cctgcccagc acctgaactc ctggggggac cctcagtctt cctcttcccc | 480 | |
| ccaaaaccca aggacaccct catgatctcc cggacccctg aggtcacatg cgtggtggtg | 540 | |
| gacgtgagcc acgaagaccc tgaggtcaag ttcaactggt acgtggacgg cgtggaggtg | 600 | |

-continued

| | |
|---|---|
| cataatgcca agacaaagcc ccggggaggag cagtacaaca gcacgtaccg ggtggtcagc | 660 |
| gtcctcaccg tcctgcacca ggactggctg aatggcaagg agtacaagtg caaggtctcc | 720 |
| aacaaagccc tcccagcccc catcgagaaa accatctcca agccaaagg ccagccccgg | 780 |
| gaaccacagg tgtacaccct gcccccatcc cgggaggaga tgaccaagaa ccaggtcagc | 840 |
| ctgacctgcc tggtcaaagg cttctatccc agcgacatcg ccgtggagtg ggagagcaat | 900 |
| ggccagcccg agaacaacta caagaccacc cctcccgtgc tggactccga cggctccttc | 960 |
| ttcctctaca gcaagctcac cgtggacaag agcaggtggc agcagggcaa cgtcttctca | 1020 |
| tgctccgtga tgcatgaggc tctgcacaac cactacaccc agaagagcct ctccctgtct | 1080 |
| cccggcaaat gagatatcgg gcccgtttaa acgggtggca | 1120 |

<210> SEQ ID NO 17
<211> LENGTH: 37
<212> TYPE: DNA
<213> ORGANISM: Artificial Sequence
<220> FEATURE:
<223> OTHER INFORMATION: Synthetic

<400> SEQUENCE: 17

| | |
|---|---|
| aaagctagca tgctgctgct gctgctgctg ctgggcc | 37 |

<210> SEQ ID NO 18
<211> LENGTH: 36
<212> TYPE: DNA
<213> ORGANISM: Artificial Sequence
<220> FEATURE:
<223> OTHER INFORMATION: Synthetic

<400> SEQUENCE: 18

| | |
|---|---|
| aaaagatctt catgtctgct cgaagcggcc ggccgc | 36 |

<210> SEQ ID NO 19
<211> LENGTH: 46
<212> TYPE: DNA
<213> ORGANISM: Artificial Sequence
<220> FEATURE:
<223> OTHER INFORMATION: Synthetic

<400> SEQUENCE: 19

| | |
|---|---|
| ttgattattg actagtattt atgtatatta acagcacatt aacagc | 46 |

<210> SEQ ID NO 20
<211> LENGTH: 49
<212> TYPE: DNA
<213> ORGANISM: Artificial Sequence
<220> FEATURE:
<223> OTHER INFORMATION: Synthetic

<400> SEQUENCE: 20

| | |
|---|---|
| gcagcagcat gctagcggct ttctcctggg agaactgaag gcacagcgg | 49 |

<210> SEQ ID NO 21
<211> LENGTH: 44
<212> TYPE: DNA
<213> ORGANISM: Artificial Sequence
<220> FEATURE:
<223> OTHER INFORMATION: Synthetic

<400> SEQUENCE: 21

| | |
|---|---|
| ttgattattg actagtctaa agtgattcct aaagaattct tccc | 44 |

```
<210> SEQ ID NO 22
<211> LENGTH: 43
<212> TYPE: DNA
<213> ORGANISM: Artificial Sequence
<220> FEATURE:
<223> OTHER INFORMATION: Synthetic

<400> SEQUENCE: 22
gcagcagcat gctagcgatg cctttgggg aagaagcggc ccc                    43

<210> SEQ ID NO 23
<211> LENGTH: 46
<212> TYPE: DNA
<213> ORGANISM: Artificial Sequence
<220> FEATURE:
<223> OTHER INFORMATION: Synthetic

<400> SEQUENCE: 23
ttgattattg actagtatgg tggcacaatc atggttcact gcagcc                46

<210> SEQ ID NO 24
<211> LENGTH: 49
<212> TYPE: DNA
<213> ORGANISM: Artificial Sequence
<220> FEATURE:
<223> OTHER INFORMATION: Synthetic

<400> SEQUENCE: 24
gcagcagcat gctagctctg agtgcctaaa ttaagaatag agtaacatc             49

<210> SEQ ID NO 25
<211> LENGTH: 47
<212> TYPE: DNA
<213> ORGANISM: Artificial Sequence
<220> FEATURE:
<223> OTHER INFORMATION: Synthetic

<400> SEQUENCE: 25
ttgattattg actagtccta gtgtggcttc tgcattttc acagtgc                47

<210> SEQ ID NO 26
<211> LENGTH: 47
<212> TYPE: DNA
<213> ORGANISM: Artificial Sequence
<220> FEATURE:
<223> OTHER INFORMATION: Synthetic

<400> SEQUENCE: 26
ttgattattg actagtcctc ggctcacggc agcctcgacc tttcggc                47

<210> SEQ ID NO 27
<211> LENGTH: 46
<212> TYPE: DNA
<213> ORGANISM: Artificial Sequence
<220> FEATURE:
<223> OTHER INFORMATION: Synthetic

<400> SEQUENCE: 27
ttgattattg actagtcctc tcgagtaact gggactacag gcatgc                46

<210> SEQ ID NO 28
<211> LENGTH: 45
<212> TYPE: DNA
<213> ORGANISM: Artificial Sequence
<220> FEATURE:
<223> OTHER INFORMATION: Synthetic
```

<400> SEQUENCE: 28
ttgattattg actagtgcag tttcgcccag tggttagaag cgtgg        45

<210> SEQ ID NO 29
<211> LENGTH: 49
<212> TYPE: DNA
<213> ORGANISM: Artificial Sequence
<220> FEATURE:
<223> OTHER INFORMATION: Synthetic

<400> SEQUENCE: 29
ttgattattg actagtgctt cctggaggtg cattctaaga gcgctcccc    49

<210> SEQ ID NO 30
<211> LENGTH: 47
<212> TYPE: DNA
<213> ORGANISM: Artificial Sequence
<220> FEATURE:
<223> OTHER INFORMATION: Synthetic

<400> SEQUENCE: 30
ttgattattg actagtgtaa agcttgtgct ctgaataaat gacaagg      47

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
tactagcggt tttacgggcg                                    20

<210> SEQ ID NO 32
<211> LENGTH: 24
<212> TYPE: DNA
<213> ORGANISM: Artificial Sequence
<220> FEATURE:
<223> OTHER INFORMATION: Synthetic

<400> SEQUENCE: 32
tcgaacagga ggagcagaga gcga                               24

<210> SEQ ID NO 33
<211> LENGTH: 37
<212> TYPE: DNA
<213> ORGANISM: Artificial Sequence
<220> FEATURE:
<223> OTHER INFORMATION: Synthetic

<400> SEQUENCE: 33
aaagctagca tgctgctgct gctgctgctg ctgggcc                 37

<210> SEQ ID NO 34
<211> LENGTH: 36
<212> TYPE: DNA
<213> ORGANISM: Artificial Sequence
<220> FEATURE:
<223> OTHER INFORMATION: Synthetic

<400> SEQUENCE: 34
aaaagatctt catgtctgct cgaagcggcc ggccgc                  36

<210> SEQ ID NO 35
<211> LENGTH: 78

```
<212> TYPE: DNA
<213> ORGANISM: Artificial Sequence
<220> FEATURE:
<223> OTHER INFORMATION: Synthetic

<400> SEQUENCE: 35
ggaaattgag aagtatcatt cacaacagta ccacaaacat gaaataaatg tggatcctat    60
taatagtaat caattacg                                                 78

<210> SEQ ID NO 36
<211> LENGTH: 78
<212> TYPE: DNA
<213> ORGANISM: Artificial Sequence
<220> FEATURE:
<223> OTHER INFORMATION: Synthetic

<400> SEQUENCE: 36
ctcattctgt gggttgtcat ttcacttcct tgatgctatc ctttcaagca aaatcctagt    60
caataatcaa tgtcaacg                                                 78

<210> SEQ ID NO 37
<211> LENGTH: 77
<212> TYPE: DNA
<213> ORGANISM: Artificial Sequence
<220> FEATURE:
<223> OTHER INFORMATION: Synthetic

<400> SEQUENCE: 37
cttattttct aagtagtata gacttaattg tgagaacaaa ataaaaactt ggatcctatt    60
aatagtaatc aattacg                                                  77

<210> SEQ ID NO 38
<211> LENGTH: 74
<212> TYPE: DNA
<213> ORGANISM: Artificial Sequence
<220> FEATURE:
<223> OTHER INFORMATION: Synthetic

<400> SEQUENCE: 38
ctcttcccat tctcatttga atctacttca aaaggtttac catactaaga cctagtcaat    60
aatcaatgtc aacg                                                     74

<210> SEQ ID NO 39
<211> LENGTH: 79
<212> TYPE: DNA
<213> ORGANISM: Artificial Sequence
<220> FEATURE:
<223> OTHER INFORMATION: Synthetic

<400> SEQUENCE: 39
cgcctgtaat cccagcactt tgggaggctg aggcgggtgg atcacctgag gtcgatccta    60
ttaatagtaa tcaattacg                                                79

<210> SEQ ID NO 40
<211> LENGTH: 77
<212> TYPE: DNA
<213> ORGANISM: Artificial Sequence
<220> FEATURE:
<223> OTHER INFORMATION: Synthetic

<400> SEQUENCE: 40
catacagaag ccagtttgaa ctgagacctc actccatttc ttacaagtta tgccctagtc    60
```
aataatcaat gtcaacg 77

<210> SEQ ID NO 41
<211> LENGTH: 77
<212> TYPE: DNA
<213> ORGANISM: Artificial Sequence
<220> FEATURE:
<223> OTHER INFORMATION: Synthetic

<400> SEQUENCE: 41
accgttttat attgtttaag catttcctag acatatttgg ctacaaatct agatcctatt    60
aatagtaatc aattacg    77

<210> SEQ ID NO 42
<211> LENGTH: 77
<212> TYPE: DNA
<213> ORGANISM: Artificial Sequence
<220> FEATURE:
<223> OTHER INFORMATION: Synthetic

<400> SEQUENCE: 42
gatcttaggg gggctgatta tataaaacaa tagaaatgta gtcttagatg aaacctagtc    60
aataatcaat gtcaacg    77

<210> SEQ ID NO 43
<211> LENGTH: 79
<212> TYPE: DNA
<213> ORGANISM: Artificial Sequence
<220> FEATURE:
<223> OTHER INFORMATION: Synthetic

<400> SEQUENCE: 43
cacaaagttc actgtcaagg ccaggtgatg aggcccacac atgcccggac cttgatccta    60
ttaatagtaa tcaattacg    79

<210> SEQ ID NO 44
<211> LENGTH: 78
<212> TYPE: DNA
<213> ORGANISM: Artificial Sequence
<220> FEATURE:
<223> OTHER INFORMATION: Synthetic

<400> SEQUENCE: 44
caaaacctca tctctactga aaatagaaaa ttagctgggc gtggtggcag gtgccctagt    60
caataatcaa tgtcaacg    78

<210> SEQ ID NO 45
<211> LENGTH: 38
<212> TYPE: DNA
<213> ORGANISM: Artificial Sequence
<220> FEATURE:
<223> OTHER INFORMATION: Synthetic

<400> SEQUENCE: 45
aaaactagtc agagaggaat ctttgcagct aatggacc    38

<210> SEQ ID NO 46
<211> LENGTH: 35
<212> TYPE: DNA
<213> ORGANISM: Artificial Sequence
<220> FEATURE:
<223> OTHER INFORMATION: Synthetic

<400> SEQUENCE: 46

-continued aaagatatcc ctagccagct tgggtggtac caagc                35

<210> SEQ ID NO 47
<211> LENGTH: 35
<212> TYPE: DNA
<213> ORGANISM: Artificial Sequence
<220> FEATURE:
<223> OTHER INFORMATION: Synthetic

<400> SEQUENCE: 47
aaaactagtc tgtggaatgt gtgtcagtta gggtg                35

<210> SEQ ID NO 48
<211> LENGTH: 34
<212> TYPE: DNA
<213> ORGANISM: Artificial Sequence
<220> FEATURE:
<223> OTHER INFORMATION: Synthetic

<400> SEQUENCE: 48
aaagatatca gcttttgca aaagcctagg cctc                34

<210> SEQ ID NO 49
<211> LENGTH: 77
<212> TYPE: DNA
<213> ORGANISM: Artificial Sequence
<220> FEATURE:
<223> OTHER INFORMATION: Synthetic

<400> SEQUENCE: 49
ggaaattgag aagtatcatt cacaacagta ccacaaacat gaaataaatg tgctagtcag    60
agaggaatct ttgcagc                                                   77

<210> SEQ ID NO 50
<211> LENGTH: 79
<212> TYPE: DNA
<213> ORGANISM: Artificial Sequence
<220> FEATURE:
<223> OTHER INFORMATION: Synthetic

<400> SEQUENCE: 50
ggaaattgag aagtatcatt cacaacagta ccacaaacat gaaataaatg tgctagtctg    60
tggaatgtgt gtcagttag                                                 79

<210> SEQ ID NO 51
<211> LENGTH: 78
<212> TYPE: DNA
<213> ORGANISM: Artificial Sequence
<220> FEATURE:
<223> OTHER INFORMATION: Synthetic

<400> SEQUENCE: 51
ctcattctgt gggttgtcat ttcacttcct tgatgctatc ctttcaagca aaattttaaa    60
actttatcca tctttgca                                                  78

<210> SEQ ID NO 52
<211> LENGTH: 76
<212> TYPE: DNA
<213> ORGANISM: Artificial Sequence
<220> FEATURE:
<223> OTHER INFORMATION: Synthetic

<400> SEQUENCE: 52
cttattttct aagtagtata gacttaattg tgagaacaaa ataaaaactt gctagtcaga    60
gaggaatctt tgcagc    76

<210> SEQ ID NO 53
<211> LENGTH: 78
<212> TYPE: DNA
<213> ORGANISM: Artificial Sequence
<220> FEATURE:
<223> OTHER INFORMATION: Synthetic

<400> SEQUENCE: 53
cttattttct aagtagtata gacttaattg tgagaacaaa ataaaaactt gctagtctgt    60
ggaatgtgtg tcagttag    78

<210> SEQ ID NO 54
<211> LENGTH: 80
<212> TYPE: DNA
<213> ORGANISM: Artificial Sequence
<220> FEATURE:
<223> OTHER INFORMATION: Synthetic

<400> SEQUENCE: 54
ctcttcccat tctcatttga atctacttca aaaggtttac catactaaga actagtttta    60
aaactttatc catctttgca    80

<210> SEQ ID NO 55
<211> LENGTH: 28
<212> TYPE: DNA
<213> ORGANISM: Artificial Sequence
<220> FEATURE:
<223> OTHER INFORMATION: Synthetic

<400> SEQUENCE: 55
ccacgcgccc tgtagcggcg cattaagc    28

<210> SEQ ID NO 56
<211> LENGTH: 30
<212> TYPE: DNA
<213> ORGANISM: Artificial Sequence
<220> FEATURE:
<223> OTHER INFORMATION: Synthetic

<400> SEQUENCE: 56
aaacccggga gcttttttgca aaagcctagg    30

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
cgcggccgca ctagtgacgt    20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
cactagtgcg gccgcgacgt    20

<210> SEQ ID NO 59
<211> LENGTH: 25
<212> TYPE: DNA
<213> ORGANISM: Artificial Sequence
<220> FEATURE:
<223> OTHER INFORMATION: Synthetic

<400> SEQUENCE: 59
aaacatatgg cgacatccag atgac                                           25

<210> SEQ ID NO 60
<211> LENGTH: 26
<212> TYPE: DNA
<213> ORGANISM: Artificial Sequence
<220> FEATURE:
<223> OTHER INFORMATION: Synthetic

<400> SEQUENCE: 60
aaacgtacgc ttgatctcca ccttgg                                          26

<210> SEQ ID NO 61
<211> LENGTH: 26
<212> TYPE: DNA
<213> ORGANISM: Artificial Sequence
<220> FEATURE:
<223> OTHER INFORMATION: Synthetic

<400> SEQUENCE: 61
aaagctgagc caggtgcagc tgcagg                                          26

<210> SEQ ID NO 62
<211> LENGTH: 28
<212> TYPE: DNA
<213> ORGANISM: Artificial Sequence
<220> FEATURE:
<223> OTHER INFORMATION: Synthetic

<400> SEQUENCE: 62
aaagctgagc tcacggtcac cagggttc                                        28

<210> SEQ ID NO 63
<211> LENGTH: 44
<212> TYPE: DNA
<213> ORGANISM: Artificial Sequence
<220> FEATURE:
<223> OTHER INFORMATION: Synthetic

<400> SEQUENCE: 63
cttttgcaaa aagcttcgcg ttacataact tacggtaaat ggcc                      44

<210> SEQ ID NO 64
<211> LENGTH: 43
<212> TYPE: DNA
<213> ORGANISM: Artificial Sequence
<220> FEATURE:
<223> OTHER INFORMATION: Synthetic

<400> SEQUENCE: 64
ttcatggtgg cgctagcccg cagatatcga tccgagctcg gta                       43

<210> SEQ ID NO 65
<211> LENGTH: 44
<212> TYPE: DNA
<213> ORGANISM: Artificial Sequence
<220> FEATURE:

<223> OTHER INFORMATION: Synthetic

<400> SEQUENCE: 65
tgacgtcgac aagcttcgcg ttacataact tacggtaaat ggcc           44

<210> SEQ ID NO 66
<211> LENGTH: 107
<212> TYPE: DNA
<213> ORGANISM: Artificial Sequence
<220> FEATURE:
<223> OTHER INFORMATION: Synthetic

<400> SEQUENCE: 66
ctggatgtcg ccatatgcgc cggagatcca cagcagcagg gagatgaaca cctgggtctg           60
cagcaccatg gtggcgctag cccgcagata tcgatccgag ctcggta           107

<210> SEQ ID NO 67
<211> LENGTH: 80
<212> TYPE: DNA
<213> ORGANISM: Artificial Sequence
<220> FEATURE:
<223> OTHER INFORMATION: Synthetic

<400> SEQUENCE: 67
ctcttcccat tctcatttga atctacttca aaaggtttac catactaaga ctcgaggcac           60
tagtgacgtc aggtggcact           80

<210> SEQ ID NO 68
<211> LENGTH: 80
<212> TYPE: DNA
<213> ORGANISM: Artificial Sequence
<220> FEATURE:
<223> OTHER INFORMATION: Synthetic

<400> SEQUENCE: 68
ctcttcccat tctcatttga atctacttca aaaggtttac catactaaga gcactagtga           60
cgtcaggtgg cacttttcgg           80

<210> SEQ ID NO 69
<211> LENGTH: 79
<212> TYPE: DNA
<213> ORGANISM: Artificial Sequence
<220> FEATURE:
<223> OTHER INFORMATION: Synthetic

<400> SEQUENCE: 69
catgcacaga ttagccattt agtacttact aaatcaaact caatttctga agtctagtta           60
ttaatagtaa tcaattacg           79

<210> SEQ ID NO 70
<211> LENGTH: 80
<212> TYPE: DNA
<213> ORGANISM: Artificial Sequence
<220> FEATURE:
<223> OTHER INFORMATION: Synthetic

<400> SEQUENCE: 70
ctcattctgt gggttgtcat ttcacttcct tgatgctatc ctttcaagca aaattcaata           60
atcaatgtca acgcgtatat           80

<210> SEQ ID NO 71
<211> LENGTH: 79

```
<212> TYPE: DNA
<213> ORGANISM: Artificial Sequence
<220> FEATURE:
<223> OTHER INFORMATION: Synthetic

<400> SEQUENCE: 71
acactggtca aagggacagg tcattgttat gctggcaatc aggctgctga aaactagtta      60
ttaatagtaa tcaattacg                                                   79

<210> SEQ ID NO 72
<211> LENGTH: 80
<212> TYPE: DNA
<213> ORGANISM: Artificial Sequence
<220> FEATURE:
<223> OTHER INFORMATION: Synthetic

<400> SEQUENCE: 72
actgtagctt cttatttttt acctgcagtg cattcctgta aaagtagtgt ggagtcaata      60
atcaatgtca acgcgtatat                                                  80

<210> SEQ ID NO 73
<211> LENGTH: 80
<212> TYPE: DNA
<213> ORGANISM: Artificial Sequence
<220> FEATURE:
<223> OTHER INFORMATION: Synthetic

<400> SEQUENCE: 73
ctggaaattg agaagtatca ttcacaacag taccacaaac atgaaataaa tgtgctagtt      60
attaatagta atcaattacg                                                  80

<210> SEQ ID NO 74
<211> LENGTH: 80
<212> TYPE: DNA
<213> ORGANISM: Artificial Sequence
<220> FEATURE:
<223> OTHER INFORMATION: Synthetic

<400> SEQUENCE: 74
ccaagcttgt ccaaccgcgg cctgcaggct gcatgcagcc tgtgaaggct ttgatcaata      60
atcaatgtca acgcgtatat                                                  80

<210> SEQ ID NO 75
<211> LENGTH: 80
<212> TYPE: DNA
<213> ORGANISM: Artificial Sequence
<220> FEATURE:
<223> OTHER INFORMATION: Synthetic

<400> SEQUENCE: 75
tcaatcattt atcaatttta tcttcaaagt ccctcacttc agggagatga tatactagtt      60
attaatagta atcaattacg                                                  80

<210> SEQ ID NO 76
<211> LENGTH: 80
<212> TYPE: DNA
<213> ORGANISM: Artificial Sequence
<220> FEATURE:
<223> OTHER INFORMATION: Synthetic

<400> SEQUENCE: 76
atatataaaa gttcatgtat atataaaatc atgcaataca cggccttttg tgactcaata      60
```

```
atcaatgtca acgcgtatat                                              80

<210> SEQ ID NO 77
<211> LENGTH: 80
<212> TYPE: DNA
<213> ORGANISM: Artificial Sequence
<220> FEATURE:
<223> OTHER INFORMATION: Synthetic

<400> SEQUENCE: 77
cgcataaaag gaaaagcatc cttaaaataa acaccatcaa tggctcctcg gtggctagtt   60
attaatagta atcaattacg                                              80

<210> SEQ ID NO 78
<211> LENGTH: 79
<212> TYPE: DNA
<213> ORGANISM: Artificial Sequence
<220> FEATURE:
<223> OTHER INFORMATION: Synthetic

<400> SEQUENCE: 78
gggaggctac agcttgcctc tctaaccact aaaaggcatg accctcctca aagctagtta   60
ttaatagtaa tcaattacg                                               79

<210> SEQ ID NO 79
<211> LENGTH: 80
<212> TYPE: DNA
<213> ORGANISM: Artificial Sequence
<220> FEATURE:
<223> OTHER INFORMATION: Synthetic

<400> SEQUENCE: 79
tctggcttcc ctgggccacg ctggaagaag aattgtcttg cgccacacat aaaactagtt   60
attaatagta atcaattacg                                              80

<210> SEQ ID NO 80
<211> LENGTH: 80
<212> TYPE: DNA
<213> ORGANISM: Artificial Sequence
<220> FEATURE:
<223> OTHER INFORMATION: Synthetic

<400> SEQUENCE: 80
agctgatttt tacgttaaat gtaacatgta aagaaatata tgtgtgtttt tagatcaata   60
atcaatgtca acgcgtatat                                              80

<210> SEQ ID NO 81
<211> LENGTH: 80
<212> TYPE: DNA
<213> ORGANISM: Artificial Sequence
<220> FEATURE:
<223> OTHER INFORMATION: Synthetic

<400> SEQUENCE: 81
gtgaagagga ggagatgtca aaattcaaag tcttaaatga tgtagtttta agtactagtt   60
attaatagta atcaattacg                                              80

<210> SEQ ID NO 82
<211> LENGTH: 80
<212> TYPE: DNA
<213> ORGANISM: Artificial Sequence
<220> FEATURE:
<223> OTHER INFORMATION: Synthetic
```

<400> SEQUENCE: 82
atgacacttg atattgttgt ttatattgct ggttagtatg tgccttcatt tacctcaata    60
atcaatgtca acgcgtatat                                                80

<210> SEQ ID NO 83
<211> LENGTH: 80
<212> TYPE: DNA
<213> ORGANISM: Artificial Sequence
<220> FEATURE:
<223> OTHER INFORMATION: Synthetic

<400> SEQUENCE: 83
aaaaacaaaa ctggagtaaa caagatgaat tgttttaata gaggcactgt attactagtt    60
attaatagta atcaattacg                                                80

<210> SEQ ID NO 84
<211> LENGTH: 79
<212> TYPE: DNA
<213> ORGANISM: Artificial Sequence
<220> FEATURE:
<223> OTHER INFORMATION: Synthetic

<400> SEQUENCE: 84
atacaatgtt ccatgtattc tgtgcctgaa cctatgcagc gatgtagctg aagtcaataa    60
tcaatgtcaa cgcgtatat                                                 79

<210> SEQ ID NO 85
<211> LENGTH: 80
<212> TYPE: DNA
<213> ORGANISM: Artificial Sequence
<220> FEATURE:
<223> OTHER INFORMATION: Synthetic

<400> SEQUENCE: 85
gatcttattt tctaagtagt atagacttaa ttgtgagaac aaaataaaaa cttgctagtt    60
attaatagta atcaattacg                                                80

<210> SEQ ID NO 86
<211> LENGTH: 80
<212> TYPE: DNA
<213> ORGANISM: Artificial Sequence
<220> FEATURE:
<223> OTHER INFORMATION: Synthetic

<400> SEQUENCE: 86
tgttgttttc agccactaag tttgaggtga tttgttctgg cagtcctagg aaactcaata    60
atcaatgtca acgcgtatat                                                80

<210> SEQ ID NO 87
<211> LENGTH: 80
<212> TYPE: DNA
<213> ORGANISM: Artificial Sequence
<220> FEATURE:
<223> OTHER INFORMATION: Synthetic

<400> SEQUENCE: 87
agcctacact acccttgca gcctttggta actatccttc tgctgtctac ctcctcaata    60
atcaatgtca acgcgtatat                                                80

<210> SEQ ID NO 88

```
<211> LENGTH: 80
<212> TYPE: DNA
<213> ORGANISM: Artificial Sequence
<220> FEATURE:
<223> OTHER INFORMATION: Synthetic

<400> SEQUENCE: 88
aggagctcct gaatgaagga catcactcag ctgtgttaag tatctggaac aatactagtt     60
attaatagta atcaattacg                                                 80

<210> SEQ ID NO 89
<211> LENGTH: 80
<212> TYPE: DNA
<213> ORGANISM: Artificial Sequence
<220> FEATURE:
<223> OTHER INFORMATION: Synthetic

<400> SEQUENCE: 89
gacataaaat gtaagatatg atatgctatg taagatatga tacctgcctt aaaatcaata     60
atcaatgtca acgcgtatat                                                 80

<210> SEQ ID NO 90
<211> LENGTH: 80
<212> TYPE: DNA
<213> ORGANISM: Artificial Sequence
<220> FEATURE:
<223> OTHER INFORMATION: Synthetic

<400> SEQUENCE: 90
cactgcttga tacttactgt ggactttgaa aattatgaat gtgtgtgtgt gtgtctagtt     60
attaatagta atcaattacg                                                 80

<210> SEQ ID NO 91
<211> LENGTH: 80
<212> TYPE: DNA
<213> ORGANISM: Artificial Sequence
<220> FEATURE:
<223> OTHER INFORMATION: Synthetic

<400> SEQUENCE: 91
caattacatt ccagtgatct gctacttaga atgcatgact gaactcctgg gtggtcaata     60
atcaatgtca acgcgtatat                                                 80

<210> SEQ ID NO 92
<211> LENGTH: 80
<212> TYPE: DNA
<213> ORGANISM: Artificial Sequence
<220> FEATURE:
<223> OTHER INFORMATION: Synthetic

<400> SEQUENCE: 92
ttattttgaa gagaaactcc tggttcccac ttaaaatcct ttcttgtttc caagctagtt     60
attaatagta atcaattacg                                                 80

<210> SEQ ID NO 93
<211> LENGTH: 80
<212> TYPE: DNA
<213> ORGANISM: Artificial Sequence
<220> FEATURE:
<223> OTHER INFORMATION: Synthetic

<400> SEQUENCE: 93
aagcagtgtg tgtttacctg catgtgtatg tgaattaact ctgttcctga ggcatcaata     60
```
atcaatgtca acgcgtatat                                              80

<210> SEQ ID NO 94
<211> LENGTH: 80
<212> TYPE: DNA
<213> ORGANISM: Artificial Sequence
<220> FEATURE:
<223> OTHER INFORMATION: Synthetic

<400> SEQUENCE: 94
attgcatgtt ctcatttatt tgtgggatgt aaaaatcaaa acaatagaac gtatctagtt    60
attaatagta atcaattacg                                              80

<210> SEQ ID NO 95
<211> LENGTH: 80
<212> TYPE: DNA
<213> ORGANISM: Artificial Sequence
<220> FEATURE:
<223> OTHER INFORMATION: Synthetic

<400> SEQUENCE: 95
ttgggaggcc gcagctggta gatcacttga ggccacgaat ttgacaccag caggtcaata    60
atcaatgtca acgcgtatat                                              80

<210> SEQ ID NO 96
<211> LENGTH: 79
<212> TYPE: DNA
<213> ORGANISM: Artificial Sequence
<220> FEATURE:
<223> OTHER INFORMATION: Synthetic

<400> SEQUENCE: 96
atcccctgct ctgctaaaaa agaatggatg ttgactctca ggccctagtt cttgatccta    60
ttaatagtaa tcaattacg                                               79

<210> SEQ ID NO 97
<211> LENGTH: 78
<212> TYPE: DNA
<213> ORGANISM: Artificial Sequence
<220> FEATURE:
<223> OTHER INFORMATION: Synthetic

<400> SEQUENCE: 97
ctaaagtgct gggattacag gcataagcca ccgtgcccgg ctggagcatt gggatcctat    60
taatagtaat caattacg                                                78

<210> SEQ ID NO 98
<211> LENGTH: 75
<212> TYPE: DNA
<213> ORGANISM: Artificial Sequence
<220> FEATURE:
<223> OTHER INFORMATION: Synthetic

<400> SEQUENCE: 98
actacttaca catttcgagt tttaaataag gcgttcaata tagagtgaac acctagtcaa    60
taatcaatgt caacg                                                   75

<210> SEQ ID NO 99
<211> LENGTH: 77
<212> TYPE: DNA
<213> ORGANISM: Artificial Sequence
<220> FEATURE:

<223> OTHER INFORMATION: Synthetic

<400> SEQUENCE: 99
caggcataag ccaccgcacc cggccacccc ttactaattt ttagtaacgt cgatcctatt     60
aatagtaatc aattacg                                                    77

<210> SEQ ID NO 100
<211> LENGTH: 76
<212> TYPE: DNA
<213> ORGANISM: Artificial Sequence
<220> FEATURE:
<223> OTHER INFORMATION: Synthetic

<400> SEQUENCE: 100
ctgattgact ttgacctctg ctttccaact ttgccccaaa gaaagttagt cacctagtca     60
ataatcaatg tcaacg                                                     76

<210> SEQ ID NO 101
<211> LENGTH: 77
<212> TYPE: DNA
<213> ORGANISM: Artificial Sequence
<220> FEATURE:
<223> OTHER INFORMATION: Synthetic

<400> SEQUENCE: 101
ttcaatgaaa caagctctgt gaggctcatt tgtacccatt tgttcagta ctgcctagtc      60 aataatcaat gtcaacg                                                    77

<210> SEQ ID NO 102
<211> LENGTH: 77
<212> TYPE: DNA
<213> ORGANISM: Artificial Sequence
<220> FEATURE:
<223> OTHER INFORMATION: Synthetic

<400> SEQUENCE: 102
acatacccag agacactgag agagacagac agacagtaaa cagaggagca cgatcctatt     60
aatagtaatc aattacg                                                    77

<210> SEQ ID NO 103
<211> LENGTH: 76
<212> TYPE: DNA
<213> ORGANISM: Artificial Sequence
<220> FEATURE:
<223> OTHER INFORMATION: Synthetic

<400> SEQUENCE: 103
gctcaattgt atcttatgaa aacaatttt caaaataaaa caagagatat gatcctatta      60
atagtaatca attacg                                                     76

<210> SEQ ID NO 104
<211> LENGTH: 77
<212> TYPE: DNA
<213> ORGANISM: Artificial Sequence
<220> FEATURE:
<223> OTHER INFORMATION: Synthetic

<400> SEQUENCE: 104
cctgtgctga ataccgtctg catatgtata ggaaagggtt aactcagcag ggatcctatt     60
aatagtaatc aattacg                                                    77

<210> SEQ ID NO 105
<211> LENGTH: 77
<212> TYPE: DNA
<213> ORGANISM: Artificial Sequence
<220> FEATURE:
<223> OTHER INFORMATION: Synthetic

<400> SEQUENCE: 105
tatgtgaatg gaaataaaat aatcaagctt gttagaattg tgttcataat gaccctagtc    60
aataatcaat gtcaacg                                                   77

<210> SEQ ID NO 106
<211> LENGTH: 75
<212> TYPE: DNA
<213> ORGANISM: Artificial Sequence
<220> FEATURE:
<223> OTHER INFORMATION: Synthetic

<400> SEQUENCE: 106
gaaagtctac aatttttca gtttaaaatg gtatttattt gtaacatgta ccctagtcaa     60
taatcaatgt caacg                                                     75

<210> SEQ ID NO 107
<211> LENGTH: 77
<212> TYPE: DNA
<213> ORGANISM: Artificial Sequence
<220> FEATURE:
<223> OTHER INFORMATION: Synthetic

<400> SEQUENCE: 107
caaagatgaa ggatgagagt gacttctgcc ttcattatgt tatgtgttca tatcctagtc    60
aataatcaat gtcaacg                                                   77

<210> SEQ ID NO 108
<211> LENGTH: 75
<212> TYPE: DNA
<213> ORGANISM: Artificial Sequence
<220> FEATURE:
<223> OTHER INFORMATION: Synthetic

<400> SEQUENCE: 108
cagtgaatta ttcactttgt cttagttaag taaaaataaa atctgactgt gatcctatta    60
atagtaatca attac                                                     75

<210> SEQ ID NO 109
<211> LENGTH: 76
<212> TYPE: DNA
<213> ORGANISM: Artificial Sequence
<220> FEATURE:
<223> OTHER INFORMATION: Synthetic

<400> SEQUENCE: 109
gaacagacag gtgaatgagc acagaggtca tttgtaaacc gtttgtggtt agcctagtca    60
ataatcaatg tcaacg                                                    76

<210> SEQ ID NO 110
<211> LENGTH: 79
<212> TYPE: DNA
<213> ORGANISM: Artificial Sequence
<220> FEATURE:
<223> OTHER INFORMATION: Synthetic

<400> SEQUENCE: 110

```
cttttttggct tctgtgttta agttattttt cccctaggcc cacaaacaga gtcgatccta    60
ttaatagtaa tcaattacg                                                 79

<210> SEQ ID NO 111
<211> LENGTH: 74
<212> TYPE: DNA
<213> ORGANISM: Artificial Sequence
<220> FEATURE:
<223> OTHER INFORMATION: Synthetic

<400> SEQUENCE: 111
aaccttggaa aaattctgtt gtgtttagaa gcatgtacca atctatcact cctagtcaat    60
aatcaatgtc aacg                                                      74

<210> SEQ ID NO 112
<211> LENGTH: 76
<212> TYPE: DNA
<213> ORGANISM: Artificial Sequence
<220> FEATURE:
<223> OTHER INFORMATION: Synthetic

<400> SEQUENCE: 112
ctattcactg tctgtaggat gaaaaagtta ataacaccct gagaggtttc gatcctatta    60
atagtaatca attacg                                                    76

<210> SEQ ID NO 113
<211> LENGTH: 75
<212> TYPE: DNA
<213> ORGANISM: Artificial Sequence
<220> FEATURE:
<223> OTHER INFORMATION: Synthetic

<400> SEQUENCE: 113
ccttagatta gtttattgta tttttttatca gctactataa ggtttacaca ccctagtcaa    60
taatcaatgt caacg                                                     75

<210> SEQ ID NO 114
<211> LENGTH: 78
<212> TYPE: DNA
<213> ORGANISM: Artificial Sequence
<220> FEATURE:
<223> OTHER INFORMATION: Synthetic

<400> SEQUENCE: 114
caagaccctc aaaattcaaa aatttccttt atcttgctgt agcacctcct gcgatcctat    60
taatagtaat caattacg                                                  78

<210> SEQ ID NO 115
<211> LENGTH: 75
<212> TYPE: DNA
<213> ORGANISM: Artificial Sequence
<220> FEATURE:
<223> OTHER INFORMATION: Synthetic

<400> SEQUENCE: 115
ggaggggata ggaaggggat gaggcctaac aggttgatga tctaggcttt acctagtcaa    60
taatcaatgt caacg                                                     75

<210> SEQ ID NO 116
<211> LENGTH: 77
<212> TYPE: DNA
<213> ORGANISM: Artificial Sequence
```

```
<220> FEATURE:
<223> OTHER INFORMATION: Synthetic

<400> SEQUENCE: 116
ctcaaaaagg agataattcc agcccctcgc cttaaagaat ccctatcaag tgatcctatt      60
aatagtaatc aattacg                                                    77

<210> SEQ ID NO 117
<211> LENGTH: 76
<212> TYPE: DNA
<213> ORGANISM: Artificial Sequence
<220> FEATURE:
<223> OTHER INFORMATION: Synthetic

<400> SEQUENCE: 117
cgcttgaacc tgggaggcag aggttgcagt gagccgagat cacgccgttg gatcctatta     60
atagtaatca attacg                                                     76

<210> SEQ ID NO 118
<211> LENGTH: 78
<212> TYPE: DNA
<213> ORGANISM: Artificial Sequence
<220> FEATURE:
<223> OTHER INFORMATION: Synthetic

<400> SEQUENCE: 118
ttaacttttt catcctacag acagtgaata gtaaagcttt ctgtgaagac atacccctagt    60 caataatcaa tgtcaacg                                                   78

<210> SEQ ID NO 119
<211> LENGTH: 76
<212> TYPE: DNA
<213> ORGANISM: Artificial Sequence
<220> FEATURE:
<223> OTHER INFORMATION: Synthetic

<400> SEQUENCE: 119
aaattatttc ctggtgggca atattagaat atggggaatg tttgcttctg agcctagtca    60
ataatcaatg tcaacg                                                    76
```